(12) United States Patent
Braunschweig et al.

(10) Patent No.: US 11,091,468 B2
(45) Date of Patent: Aug. 17, 2021

(54) CARBOHYDRATE-BINDING SMALL MOLECULES WITH ANTIVIRAL ACTIVITY

(71) Applicants: Research Foundation of the City University of New York, New York, NY (US); Texas Tech University System, Lubbock, TX (US)

(72) Inventors: Adam B. Braunschweig, New York, NY (US); Kalanidhi Palanichamy, Harrison, NJ (US); M. Fernando Bravo, New York, NY (US); Milan A. Shlain, Brooklyn, NY (US); Himanshu Garg, El Paso, TX (US); Anjali Joshi, El Paso, TX (US)

(73) Assignees: Research Foundation of the City University of New York, New York, NY (US); Texas Tech University System, Lubbock, TX (US)

( * ) Notice: Subject to any disclaimer, the term of this patent is extended or adjusted under 35 U.S.C. 154(b) by 0 days.

(21) Appl. No.: 16/519,652

(22) Filed: Jul. 23, 2019

(65) Prior Publication Data
US 2020/0024265 A1    Jan. 23, 2020

Related U.S. Application Data

(60) Provisional application No. 62/701,893, filed on Jul. 23, 2018.

(51) Int. Cl.
| | | |
|---|---|---|
| *C07D 405/14* | (2006.01) | |
| *C07D 401/14* | (2006.01) | |
| *C07C 211/27* | (2006.01) | |
| *C07D 409/14* | (2006.01) | |
| *C07D 403/14* | (2006.01) | |
| *A61P 31/12* | (2006.01) | |
| *A61P 31/14* | (2006.01) | |

(52) U.S. Cl.
CPC .......... *C07D 405/14* (2013.01); *C07C 211/27* (2013.01); *C07D 401/14* (2013.01); *C07D 403/14* (2013.01); *C07D 409/14* (2013.01); *A61P 31/12* (2018.01); *A61P 31/14* (2018.01)

(58) Field of Classification Search
None
See application file for complete search history.

(56) References Cited

U.S. PATENT DOCUMENTS 8,193,157 B2   6/2012   Balzarini et al.
9,296,688 B2   3/2016   Braunschweig et al.

OTHER PUBLICATIONS

Kim et al., "Pathogenesis and Inhibition of Flaviviruses from a Carbohydrate Perspective", 2017, Pharmaceuticals, 10(2), pp. 1-24 (doi:10.3390/ph10020044). (Year: 2017).*
Palanichamy et al., "Anti-Zika Activity of a Library of Synthetic Carbohydrate Receptors", 2019, J. Med. Chem., 62(8), p. 4110-4119. (Year: 2019).*
Bravo et al., "Synthesis and Binding of Mannose-Specific Synthetic Carbohydrate Receptors", 2020, Chem. Eur. J., 2020, 26(51), pp. 11782-11795. (Year: 2020).*
Balzarini, J.; Carbohydrate-binding agents: a potential future cornerstone for the chemotherapy of enveloped viruses?; Antiviral Chemistry & Chemotherapy; Feb. 1, 2007; pp. 1-11; vol. 18; https://doi.rg/10.1177/095632020701800101.
Alen, M. et al.; Broad Antiviral Activity of Carbohydrate-Binding Agents against the Four Serotypes of Dengue Virus in Monocyte-Derived Dendritic Cells; PLOS; Jun. 30, 2011; pp. 1-13; https://doi.org/10.1371/journal.pone.0021658.
Palanichamy, K. et al.; Binding Studies on a Library of Induced-Fit Synthetic Carbohydrate Receptors with Mannoside Selectivity; ChemPubSoc; Aug. 22, 2018; pp. 13971-13982.
Nativi, C. et al.; Pyrrolic Tripodal Receptors Effectively Recognizing Monosaccharides. Affinity Assessment through a Generalized Binding Descriptor; JACS; 2007; pp. 4377-4385; vol. 129.
Nativi, C. et al.; A β-Mannoside-Selective Pyrrolic Tripodal Receptor; Organic Letters; 2007; pp. 2685-4688; vol. 9 No. 23.
Mazik, M. et al.; Isopropylamino and Isobutylamino Groups as Recognition Sites for Carbohydrates: Acyclic Receptors with Enhanced Binding Affinity toward β-Galactosides; J. Org. Chem.; Sep. 9, 2010; pp. 6416-6423; vol. 75.

(Continued)

*Primary Examiner* — My-Chau T. Tran
(74) *Attorney, Agent, or Firm* — Peter J. Mikesell; Schmeiser, Olsen & Watts, LLP

(57) ABSTRACT

Compounds with anti-viral properties are provided that are based on the following structures:

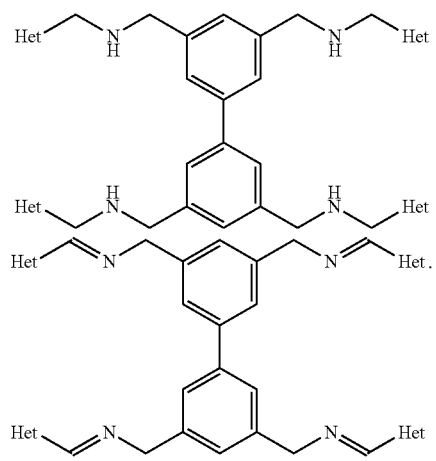

A variety of heteroaromatic groups have been found to be biologically active against the Zika (ZIKV) virus. In some embodiments, a dimeric compound is provided with each monomer linked by a repeating glycol linking group.

18 Claims, 28 Drawing Sheets

(56) References Cited

OTHER PUBLICATIONS

Rosien, J. et al.; Trimethoxybenzene- and trimethylbenzene-based compounds bearing imidazole, indole and pyrrole groups as recognition units: synthesis and evaluation of the binding properties towards carbohydrates; Organic & Biomolecular Chemistry; 2013; pp. 6569-6579; vol. 11.

Mazik, M. et al.; Beilstein Journal of Organic Chemistry; Feb. 2, 2010; pp. 1-10; vol. 6, No. 9.; doi:10.3762/bjoc.6.9.

Rieth, S. et al.; Saccharide receptor achieves concentration dependent mannoside selectivity through two distinct cooperative binding pathways; Chemical Science; 2013; pp. 357-367; vol. 3; DOI: 10.1039/c2sc20873c.

Wang, X, et al.; Development of small-molecule viral inhibitors targeting various stages of the life cycle of emerging and re-emerging viruses; Front. Med.; 2017; pp. 449-461; vol. 11, Issue 4; https://doi.org/10.1007/s11684-017-0589-5.

* cited by examiner

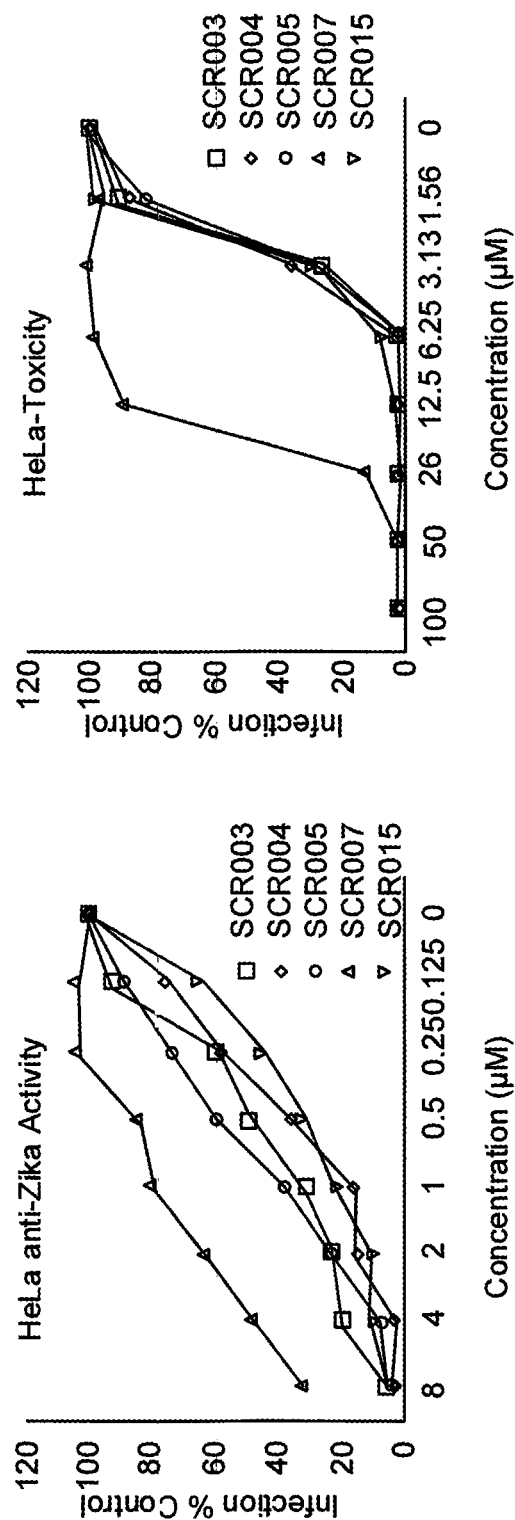

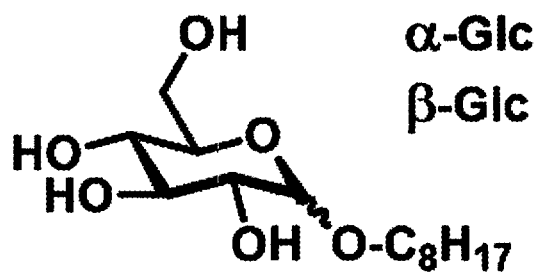
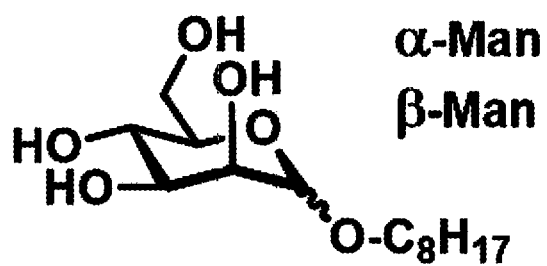
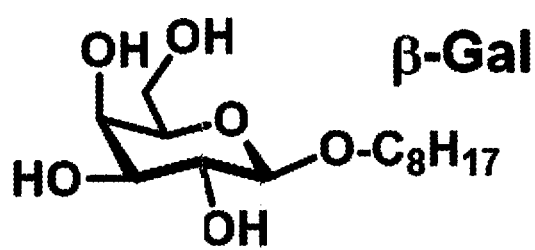
FIG. 12C

| Receptor | β – Glc | | α – Glc | | β – Man | |
|---|---|---|---|---|---|---|
| | $K_a$ (M$^{-1}$) | $\Delta G^{\circ}$ (kcal·mol$^{-1}$) | $K_a$ (M$^{-1}$) | $\Delta G^{\circ}$ (kcal·mol$^{-1}$) | $K_a$ (M$^{-1}$) | $\Delta G^{\circ}$ (kcal·mol$^{-1}$) |
| SCR001 | $1.3 \times 10^3$ | -4.24 | $3.6 \times 10^2$ | -3.48 | $3.6 \times 10^2$ C | -6.21 D |
| SCR017 | $8.4 \times 10^3$ E | -5.35 D | F | F | F | F |
| SCR018 | G | G | F | F | F | F |
| SCR019 | F | F | G | G | $7.4 \times 10^3$ E | -6.63 D |
| SCR020 | F | F | F | F | F | F |
| SCR021 | $3.3 \times 10^4$ E | -6.15 D | G | G | F | F |
| SCR022 | $8.1 \times 10^4$ E | -6.69 D | G | G | F | F |
| SCR023 | F | -7.42 D | $1.2 \times 10^2$ | -2.81 | $2.5 \times 10^2$ | -3.27 |

| | α – Man | | β – Gal | | Dilution | |
|---|---|---|---|---|---|---|
| | $K_a$ (M$^{-1}$) | $\Delta G^{\circ}$ (kcal·mol$^{-1}$) | $K_a$ (M$^{-1}$) | $\Delta G^{\circ}$ (kcal·mol$^{-1}$) | $K_a$ (M$^{-1}$) | $\Delta G^{\circ}$ (kcal·mol$^{-1}$) |
| SCR001 | $1.4 \times 10^3$ | -4.21 | $3.5 \times 10^2$ | -3.47 | $1.4 \times 10^1$ | -1.56 |
| SCR017 | F | F | F | F | F | F |
| SCR018 | $1.1 \times 10^4$ | -5.48 | F | F | F | F |
| SCR019 | $2.9 \times 10^2$ | -3.36 | F | F | F | F |
| SCR020 | $2.8 \times 10^5$ E | -7.42 D | F | F | F | F |
| SCR021 | $4.9 \times 10^2$ | -3.66 | G | G | F | F |
| SCR022 | $2.8 \times 10^2$ | -3.33 | G | G | F | F |
| SCR023 | $3.1 \times 10^2$ | -3.12 | F | F | $8.5 \times 10^3$ | -5.36 |

FIG. 16

| Receptor | β – Glc | | α – Glc | | β – Man | |
|---|---|---|---|---|---|---|
| | $K_a$ ($M^{-1}$) | $\Delta G^\circ$ (kcal·mol$^{-1}$) | $K_a$ ($M^{-1}$) | $\Delta G^\circ$ (kcal·mol$^{-1}$) | $K_a$ ($M^{-1}$) | $\Delta G^\circ$ (kcal·mol$^{-1}$) |
| SCR001 | $1.3 \times 10^3$ | -4.2 | $3.6 \times 10^2$ | -3.5 | $3.6 \times 10^4$ C | -6.1 D |
| SCR002 | $9.6 \times 10^1$ | -2.7 | E | E | $5.4 \times 10^1$ | -2.4 |
| SCR003 | $4.8 \times 10^1$ | -2.3 | E | E | E | E |
| SCR016 | $2.3 \times 10^3$ | -4.6 | $6.8 \times 10^2$ | -3.8 | $5.9 \times 10^2$ | -3.8 |
| SCR004 | $1.7 \times 10^3$ | -4.4 | $2.7 \times 10^3$ | -4.7 | $2.4 \times 10^3$ | -4.6 |
| SCR005 | $1.1 \times 10^2$ | -2.8 | $1.1 \times 10^2$ | -2.8 | $3.7 \times 10^1$ | -2.1 |
| SCR006 | F | F | F | F | F | F |
| SCR012 | $2.6 \times 10^3$ | -4.7 | $8.1 \times 10^3$ | -5.3 | $1.7 \times 10^3$ | -4.4 |

| Receptor | α – Man | | β – Gal | | Dilution | |
|---|---|---|---|---|---|---|
| | $K_a$ ($M^{-1}$) | $\Delta G^\circ$ (kcal·mol$^{-1}$) | $K_a$ ($M^{-1}$) | $\Delta G^\circ$ (kcal·mol$^{-1}$) | $K_a$ ($M^{-1}$) | $\Delta G^\circ$ (kcal·mol$^{-1}$) |
| SCR001 | $1.4 \times 10^3$ | -4.3 | $3.5 \times 10^2$ | -3.5 | $1.4 \times 10^1$ | -1.6 |
| SCR002 | $1.1 \times 10^2$ | -2.7 | E | E | E | E |
| SCR003 | $1.4 \times 10^2$ | -2.9 | E | E | E | E |
| SCR016 | $4.4 \times 10^3$ | -5.0 | $5.5 \times 10^2$ | -3.7 | E | E |
| SCR004 | $3.0 \times 10^3$ | -4.7 | $4.2 \times 10^3$ | -4.9 | $1.9 \times 10^3$ | -4.5 |
| SCR005 | $2.0 \times 10^2$ | -3.1 | $3.0 \times 10^1$ | -2.0 | E | E |
| SCR006 | F | F | F | F | E | E |
| SCR012 | $2.6 \times 10^3$ | -4.6 | $1.8 \times 10^3$ | -4.4 | F | F |

FIG. 21

CARBOHYDRATE-BINDING SMALL MOLECULES WITH ANTIVIRAL ACTIVITY

CROSS-REFERENCE TO RELATED APPLICATIONS

This application claims priority to and is a non-provisional of U.S. Patent Application 62/701,893 (filed Jul. 23, 2018), the entirety of which is incorporated herein by reference.

STATEMENT OF FEDERALLY SPONSORED RESEARCH OR DEVELOPMENT

This invention was made with government support under grant number FA9550-17-1-0356 awarded by the Air Force Office of Scientific Research. The government has certain rights in the invention.

BACKGROUND OF THE INVENTION

The Flaviviridae (FLVs), which is a family of viruses that includes Zika (ZIKV), West Nile, hepatitis C, dengue, yellow fever, and Japanese encephalitis, are an emerging global health threat. ZIKV was first isolated in the Zika forest of Uganda in 1947 from a febrile sentinel rhesus monkey. Although it is mainly transmitted to humans by mosquitoes of *Aedes* genus, sexual, maternal-to-fetal, blood transfusion, and other modes of transmission have also been reported. ZIKV was detected in Asia in the 1980s, and then outbreaks were reported in Micronesia and French Polynesia in 2007 and 2013, respectively. Since its arrival in Brazil in 2014, infecting millions of people, it has rapidly spread throughout the Americas, causing an expanding pandemic. ZIKV infection can cause symptoms such as fever, rash, muscle pain, headache, retro-orbital pain, joint pain, and conjunctivitis, but it is asymptomatic in most cases. Recent studies, however, have shown that ZIKV is also linked to severe neurological disorders such as microcephaly or other severe brain malformations in fetuses and newborn babies and Guillan-Barr syndrome in adults. Further studies revealed that ZIKV also causes severe eye diseases and blindness in newborns and conjunctivitis and uveitis in adults. Because of the severity of these symptoms, the World Health Organization declared ZIKV a global health emergency of international concern in February 2016. Although great strides have been made since 2016 in the search for drugs for the treatment of ZIKV, there is to date no vaccine or antiviral therapy approved specifically to treat ZIKV. Rather, treatment is focused currently on relieving symptoms with analgesics and antipyretics. Thus, there is an urgent need to develop novel agents with anti-ZIKV activity that can prevent or mitigate infection.

To this end, significant recent efforts have been devoted to testing libraries of compounds and repurposing of drugs already approved toward viral targets or cellular targets. Drugs such as BCX4430, brequinar, gemcitabine, sofosbuvir, and finasteride inhibit ZIKV replication by targeting RNA-dependent RNA polymerase. Other classes of agents such as viral protease inhibitors, virucidal agents, antimalarials, antibiotics, immunomodulators, immunosuppressants, fusion inhibitors, antiparasitic, proteasome inhibitors, antidepressant, cyclin-dependent kinase inhibitor, apoptosis-related drugs, and hypolipidemic drugs also possess anti-ZIKV activity. Although several compounds have advanced to phase I clinical trials, without an approved compound to treat the infection, there still remains a pressing need to explore molecules that inhibit ZIKV using alternate, less conventional strategies.

An important part of the ZIKV life cycle, and one that is not widely targeted by antiviral therapies, is the binding of proteins on the viral envelope to cell-surface glycans. After making contact with host cell surface, FLVs enter the host cell through clathrin-mediated endocytosis involving conformational changes of envelope proteins, resulting in membrane fusion and release of the viral genome. A promising therapeutic strategy involves disrupting this process with compounds that can mimic or, alternatively, bind the glycans of the host or of the virus. In FLVs, this docking process involves cellular receptors like glycosaminoglycans (GAGs), neolactotetraosylceramide, Gas6-AXL tyrosine kinase receptor complex, and the dendritic cell-specific intercellular adhesion moleculegrabbing nonintegrin (DC-SIGN), a carbohydrate-binding lectin abundant in immature dendritic cells that interacts with the highly mannosylated N-linked glycan on the FLV envelope protein. Natural and synthetic compounds that inhibit this process by mimicking or targeting glycans of host cells or of viruses have been investigated therapeutically. For example, the highly mannosylated N-glycans of the human immunodeficiency virus (HIV) have a crucial role in transmission of the pathogen into the target cells and also act as a shield to protect the virus from the host immune response. To this end, lectins such as microvirin and cyanovirin interact with the densely mannosylated gp120 of HIV envelope and inhibit viral transmission. However, because of their high molecular weight and peptidic nature, further development of these lectin-based therapeutic agents was unsuccessful. Alternatively, small-molecule-based carbohydrate-binding agents can also disrupt the viral docking process. For example, the antibiotics pradimicin A, benanomicin A, and their analogues that bind terminal D-mannopyranosides exhibit antiviral activity in cell culture with 50% effective concentration against HIV-1 in the micromolar concentration range. Similarly, 1,3,5-triazines bind gp120 of the HIV envelope and inhibit HIV-1. Aminopyrrolic synthetic carbohydrate receptors (SCRs), synthetic molecules that are designed to form supramolecular complexes with carbohydrates, bind gp120 and inhibit HIV-1 infection at micromolar concentrations. With respect to FLVs, bovine lactoferrin, an antimicrobial protein, and basic peptides derived from antimicrobial chemokines, CXCL9 and CXCL12γ, show anti-FLV activity by binding GAGs. In addition, high mannose-based dendrimers achieve anti-FLV activity by competing with the high mannose glycans of the viral envelope protein that interact with DC-SIGN. Similarly, iminosugar-based α-glucosidase inhibitors that permanently modify the viral glycan structure in cytoplasm have also been developed. There are still no reports, however, on SCRs, whose anti-FLV activity derives from binding of glycans on the viral envelope protein or disrupting interactions between hostcell glycans and glycan binding proteins on the viral envelope, and pursuing this strategy could lead to new lead compounds with potent anti-FLV activity.

The discussion above is merely provided for general background information and is not intended to be used as an aid in determining the scope of the claimed subject matter.

SUMMARY

Compounds with anti-viral properties are provided that are based on the following structures:

[Chemical structure]

[Chemical structure]

A variety of heteroaromatic groups have been found to be biologically active against the Zika (ZIKV) virus. In some embodiments, a dimeric compound is provided with each monomer linked by a repeating glycol linking group.

In a first embodiment, a method for treating a human for a Zika (ZIKV) virus infection is provided. The method comprising administering a synthetic carbohydrate receptor (SCR) to the human, wherein the synthetic carbohydrate receptor (SCR) has a structure of:

[Chemical structure]

wherein Het is a heteroaromatic group selected from 2-pyrrole, 3-pyrrole, 2-pyridine, 3-pyridine, 2-indole and 3-indole, 2-thiophene, 2-furan, N-methyl-2-imidazole and 2-phenol.

In a second embodiment, a composition of matter is provided. The composition of matter comprising a synthetic carbohydrate receptor (SCR) with a structure of:

[Chemical structure]

wherein Het is a heteroaromatic group selected from wherein Het is a heteroaromatic group selected from 3-pyrrole, 2-pyridine, 3-pyridine, 2-indole and 3-indole, 2-thiophene, 2-furan, N-methyl-2-imidazole and 2-phenol.

In a third embodiment, a composition of matter is provided. The composition of matter comprising a synthetic carbohydrate receptor (SCR) with a structure of:

[Chemical structure]

wherein Het is 2-pyrrole.

In a fourth embodiment, a composition of matter is provided. The composition of matter comprising a synthetic carbohydrate receptor (SCR) with a structure of:

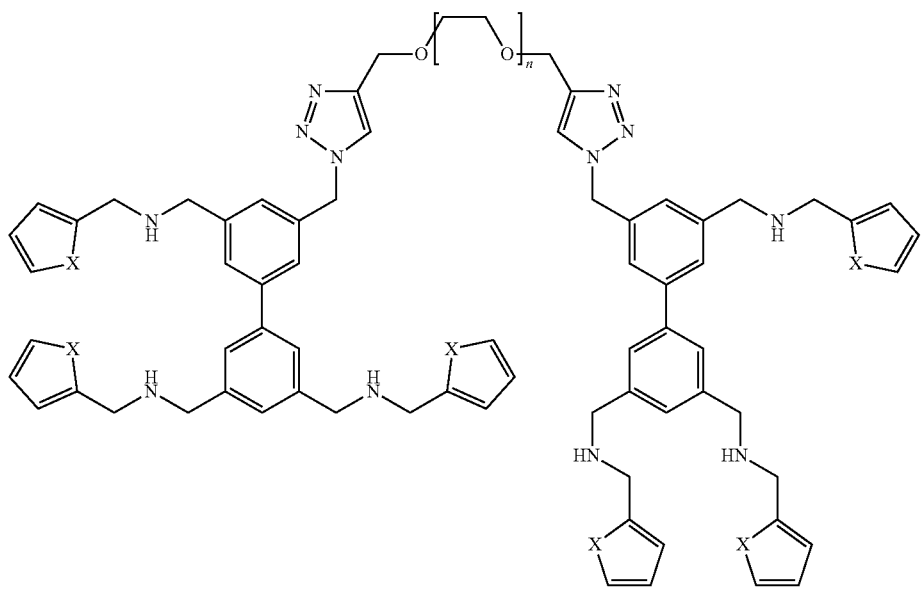

wherein n=1, 2 or 3 and X is N—H or O.

This brief description of the invention is intended only to provide a brief overview of subject matter disclosed herein according to one or more illustrative embodiments, and does not serve as a guide to interpreting the claims or to define or limit the scope of the invention, which is defined only by the appended claims. This brief description is provided to introduce an illustrative selection of concepts in a simplified form that are further described below in the detailed description. This brief description is not intended to identify key features or essential features of the claimed subject matter, nor is it intended to be used as an aid in determining the scope of the claimed subject matter. The claimed subject matter is not limited to implementations that solve any or all disadvantages noted in the background.

BRIEF DESCRIPTION OF THE DRAWINGS

So that the manner in which the features of the invention can be understood, a detailed description of the invention may be had by reference to certain embodiments, some of which are illustrated in the accompanying drawings. It is to be noted, however, that the drawings illustrate only certain embodiments of this invention and are therefore not to be considered limiting of its scope, for the scope of the invention encompasses other equally effective embodiments. The drawings are not necessarily to scale, emphasis generally being placed upon illustrating the features of certain embodiments of the invention. In the drawings, like numerals are used to indicate like parts throughout the various views. Thus, for further understanding of the invention, reference can be made to the following detailed description, read in connection with the drawings in which:

FIG. 8A is a graph showing results of HeLa cells were treated with the indicated SCRs for 30 min at room temperature followed by infection with Zika RVPs. The number of GFP positive cells per well was quantified after imaging of whole wells via the Cytation5 imager;

FIG. 8B is a graph showing Toxicity of SCRs in HeLa cells. HeLa cells were treated with the indicated SCRs and the cells were incubated for 72 h at 37° C. Cellular toxicity was measured using the CellTiter-Glo (Promega) luminescent viability assay. Data are mean of duplicate observations. One representative of three independent experiments is shown;

FIG. 12C depicts C1-Octyloxy pyranosides, whose binding with the receptors have been studied.

FIG. 16 is a data table showing Association ($K_a$) and dimerization ($K_d$) constants and free energy of binding (ΔG°) of SCR017 SCR023 with the five octyloxy pyranosides as determined from $^1H$ NMR titrations in $CD_2Cl_2$ at 298 K. [a]Titrations were performed in triplicate for SCR019.β-Man, and the standard deviations of $K_a$ and ΔG° were $3.2 \times 10^2$ $M^{-1}$ (15% error) and 0.1 kcal $mol^{-1}$, respectively. [b]$K_a$s are based on 1:1 binding models that also consider $K_d$ when appropriate. [c]Cumulative association constant (β=$K_1K_2$ ($M^{-2}$)) involving a 2:1 SCR.glycan binding model where $K_1$ and $K_2$ correspond to 1:1 and 2:1 SCR.glycan association constants, respectively. [d]Sum of free energy of binding associated with $K_1$ and $K_2$. [e]Cumulative association constant (β=$K_1K_2$ ($M^{-2}$)) involving a 1:2 SCR.glycan binding model where $K_1$ and $K_2$ correspond to 1:1 and 1:2 SCR.glycan association constants, respectively. [f]No detectable binding/dimerization above the threshold of $K_a$=$3.0 \times 10^1$ $M^{-1}$. [g]No NMR peak shifts above the threshold of Δδ>0.02 ppm;

FIG. 21 is a table listing association ($K_a$) and dimerization ($K_d$) constants and free energy of binding (ΔG°) of the receptors (SCR001, SCR002, SCR003, SCR004, SCR005, SCR006, SCR008 and SCR012 and SCR016) with the five octyloxy pyranosides as determined from NMR titrations in CD2Cl2 at 298 K[a,b]. [a] Titrations were done in triplicate for SCR012.β-Man, and the standard deviations of $K_a$ and ΔG° were $3.2 \times 10^2$ $M^{-1}$ (15% error) and 0.1 kcal $mol^{-1}$, respectively. [b] Kas are based on 1:1 binding models that also consider $K_d$ when appropriate. [c] Cumulative association constant (β=$K_1K_2$ ($M^{-2}$)) involving a 2:1 receptor-sugar binding model where $K_1$ ($1.2 \times 10^3$ $M^{-1}$) and $K_2$ ($3.0 \times 10^1$ $M^{-2}$) correspond to 1:1 and 2:1 receptor-sugar association constants, respectively. [d] Sum of free energy of binding associated with $K_1$ and $K_2$. [e] No detectable binding/dimerization above the threshold of Ka=$3.0 \times 10^1$ $M^{-1}$. [f] No NMR peak shifts above the threshold of Δδ>0.02 ppm.

DETAILED DESCRIPTION OF THE INVENTION

This disclosure provides a series of small molecule SCRs that preferentially bind mannosides and glucosides. The binding of some of these SCRs with a series of monosaccharides was studied by $^1$H NMR in chloroform and dichloromethane, and their association constants ($K_a$s) toward a series of biologically relevant monosaccharides were reported, with selectivities as high as 103:1 β Man:β Gal. This preference for binding mannosides is driven by cooperative binding modes that arise from the flexible and multivalent structures of the SCRs. As association between glycan binding proteins on the envelope of ZIKV and glycans on the cell surface is an important part of viral entry into the host cell, the SCRs may disrupt this process.

This disclosure describes the ability of small-molecule SCRs to mitigate ZIKV infection in Vero and HeLa cells using a ZIKV reporter virus based infection assay. The capsid-premembrane-envelope (C-prM-E) gene construct of ZIKV is used to generate reporter virus particles (RVPs) that package a GFP reporter expressing WNV replicon. These RVPs infect cells in a manner identical to native ZIKV, with the advantage of providing a rapid GFP readout in a 96-well format. Results of cell viability/cell toxicity, inhibition of ZIKV infection, the $IC_{50}$ values of these compounds, and some mechanistic insights based on time of compound addition are presented herein. Structure-activity relationships and correlations between mannose-binding of the SCRs and anti-ZIKV activity are discussed.

Figure 1:
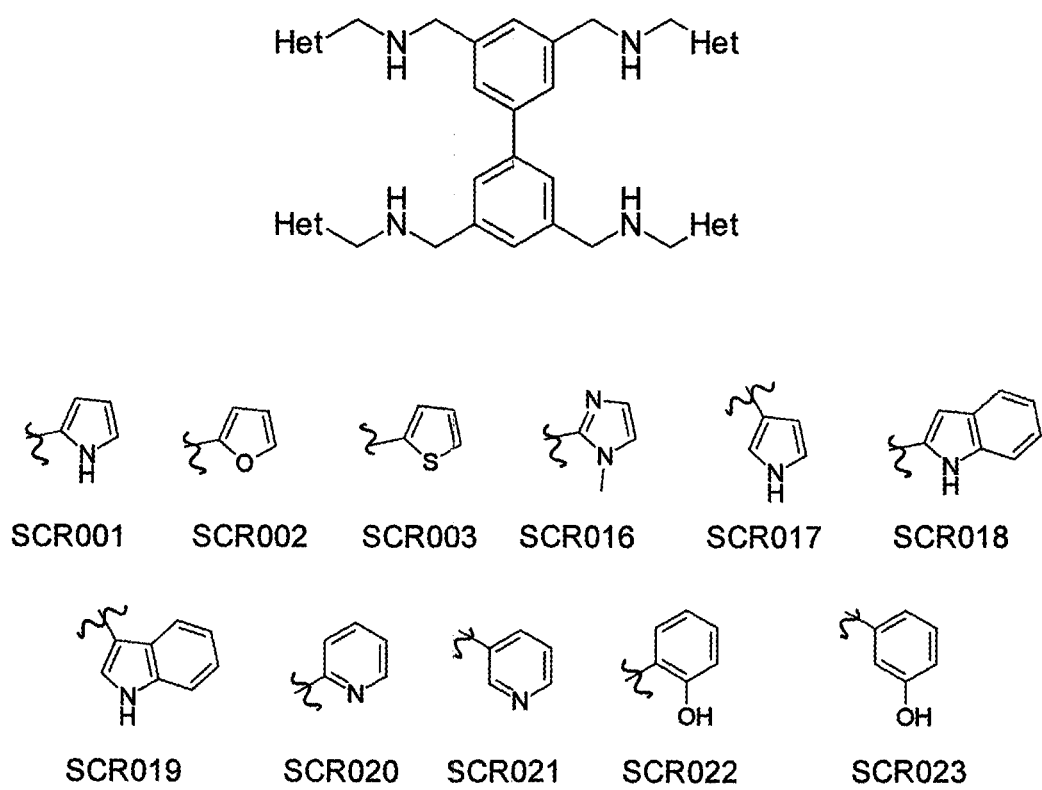
FIG. 1 is a depiction of several SCRs with amine linking groups bound to various heterocycles.
Figure 2:
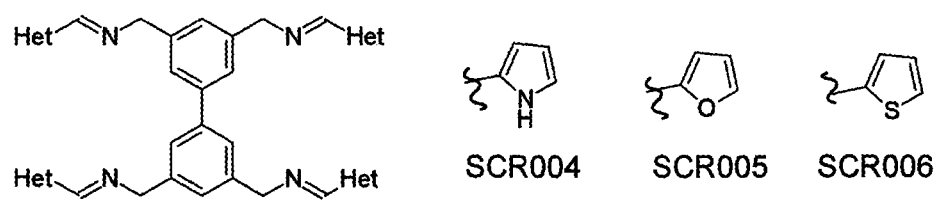
FIG. 2 is a depiction of several SCRs with imine linking groups bound to various heterocycles.
Figure 3:
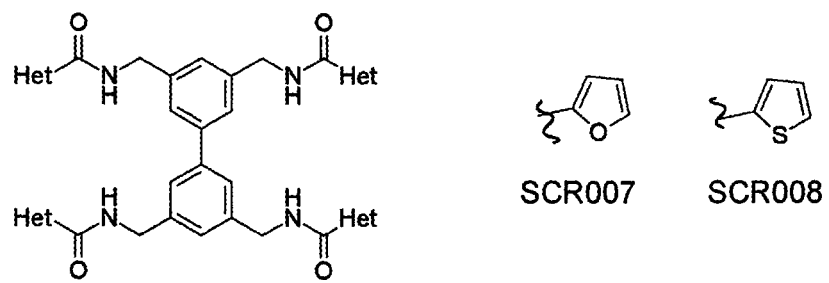
FIG. 3 is a depiction of several SCRs with amide linking groups bound to various heterocycles.
Figure 4:
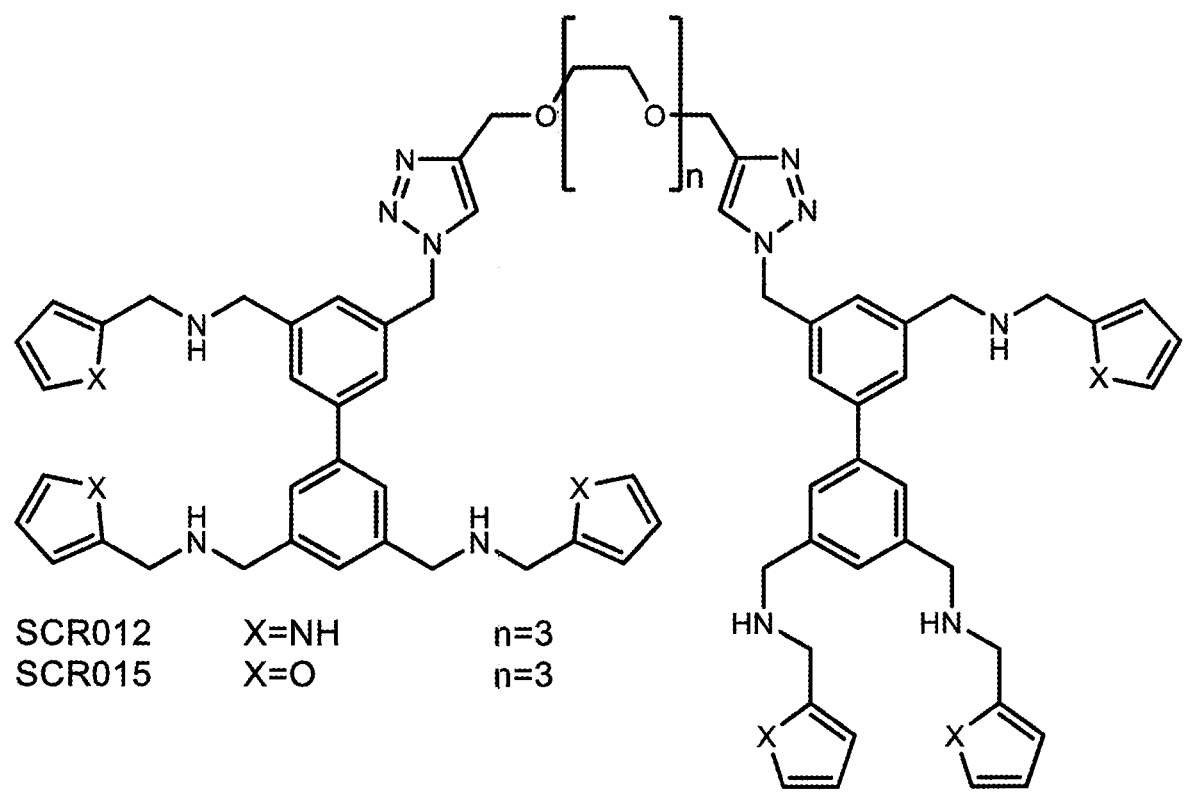
FIG. 4 is a depiction of several dimeric SCRs.
Figure 5A:
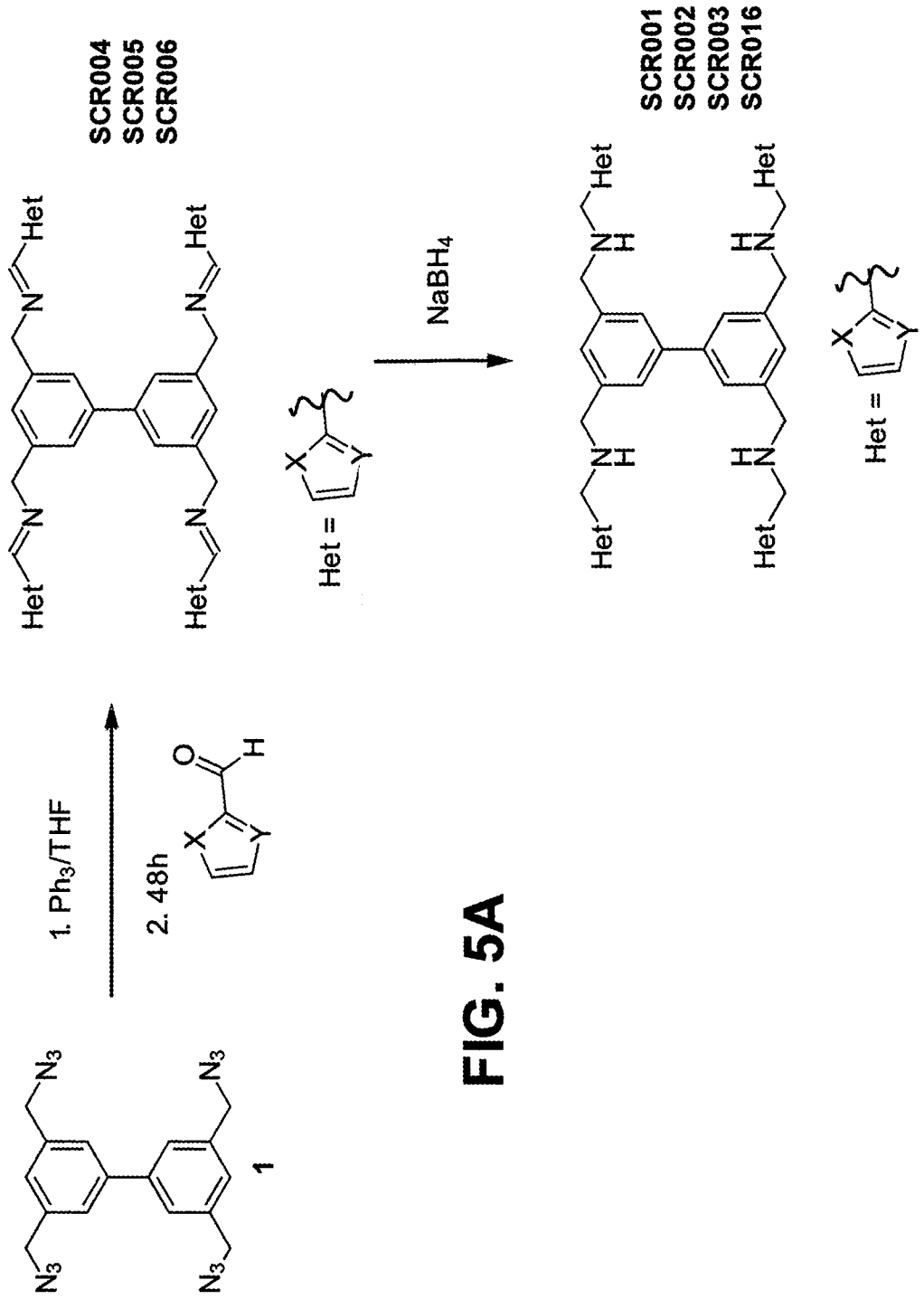
FIG. 5A is a depiction a synthetic scheme for the generation of SCRs with amine and imine linking groups.
Figure 5B:
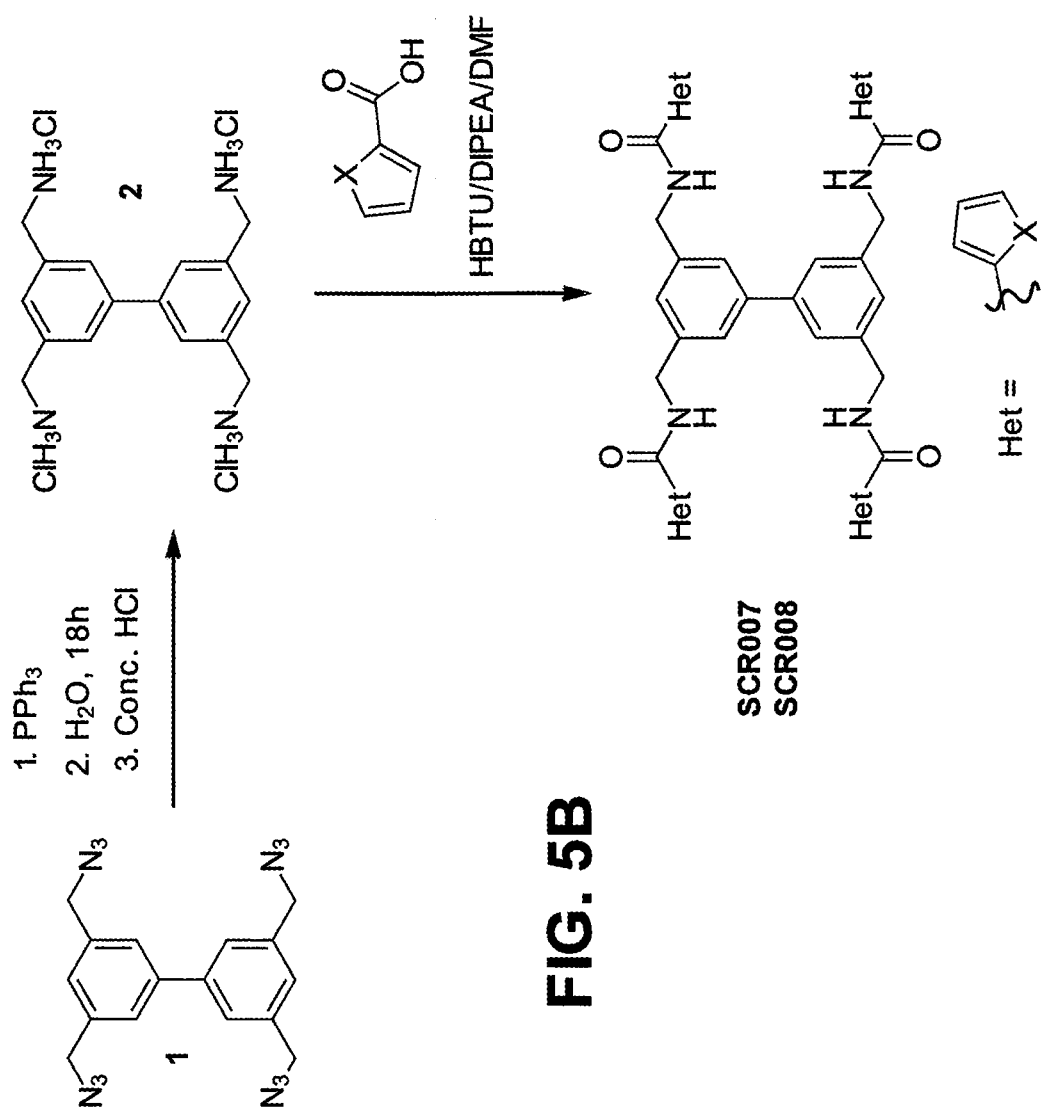
FIG. 5B is a depiction of a synthetic scheme for the generation of SCRs with amide linking groups.
Figure 5C:
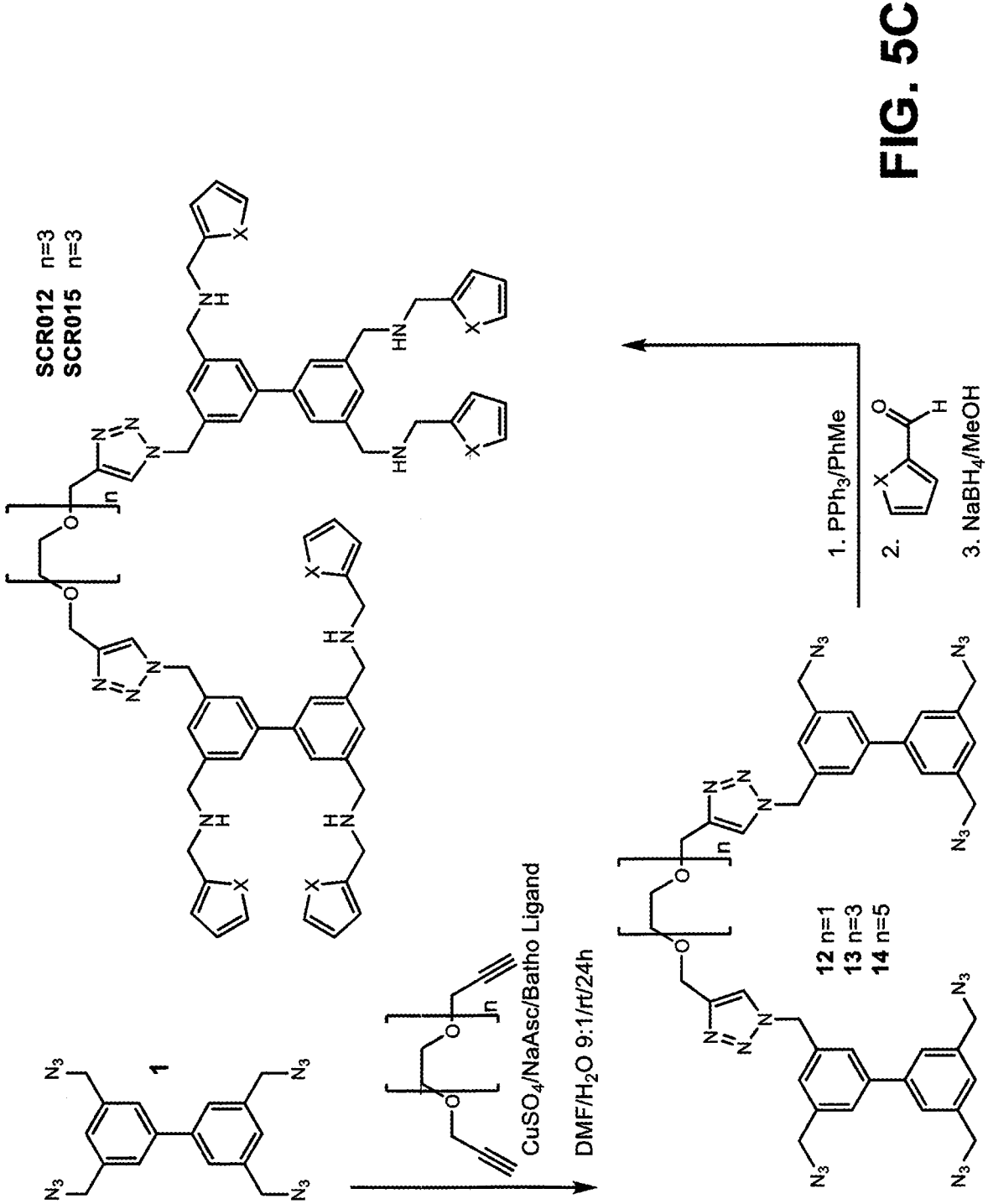
FIG. 5C is a depiction of a synthetic scheme for e generation of dimeric SCRs.

Synthesis of Carbohydrate Receptors. The SCRs studied here (FIG. 1, FIG. 2 and FIG. 3) were based upon the structure of SCR001 (FIG. 1), a mannose-selective SCR, with systematic structural alterations designed to explore relationships between molecular design and anti-ZIKV activity. Compounds SCR002, SCR003 and SCR0016 (FIG. 1) and SCR004, SCR005 and SCR006 (FIG. 2) and SCR007 and SCR008 (FIG. 3) maintain the biphenyl core and vary the heterocycle. Dimeric SCR012 and SCR015 (FIG. 4) were designed to investigate the role of multivalency on binding carbohydrate guests. Referring to FIG. 5A, FIG. 5B and FIG. 5C, compounds 1-2 and 12-14 are intermediates in the syntheses of the receptors and were assayed to investigate the importance of the heterocyclic ring and the linker on anti-ZIKV activity. All of these compounds were synthesized from common intermediate 1. The strategy used to prepare these compounds is modular, scalable, and amenable to formulating large libraries of similar molecules that can be readily synthesized to maximize antiviral activity or to understand relationships between molecular structure and viral inhibition.

Figure 6B:
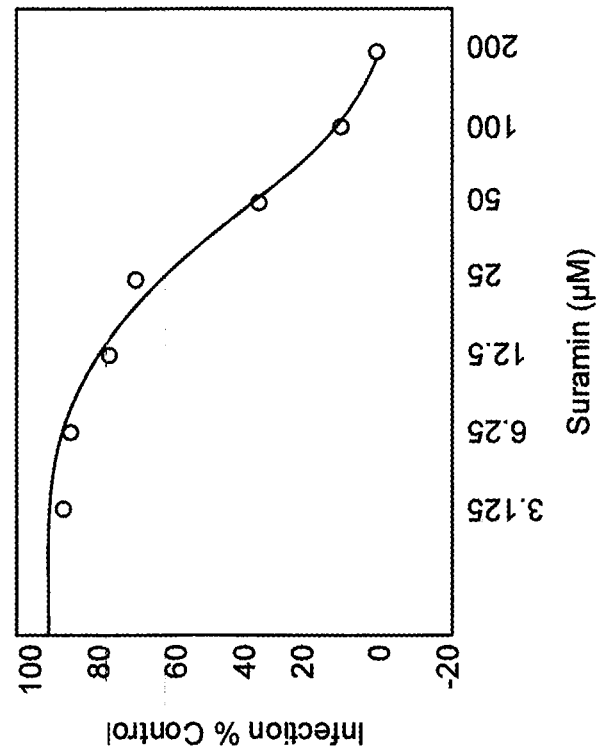
FIG. 6B is a graph depicting Inhibition curves of ZIKV infection in the presence of Suramin.
Figure 6A:
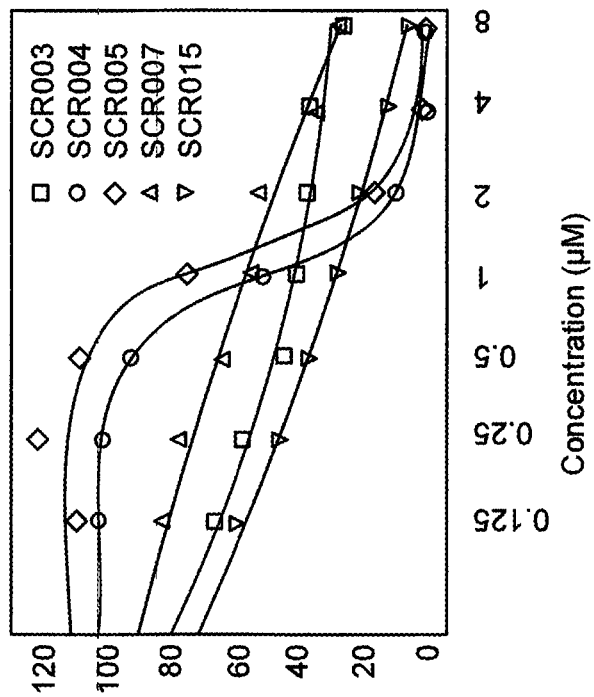
FIG. 6A is a graph depicting inhibition curves of ZIKV infection in the presence of indicated SCRs.
Figures 7A, 7B:
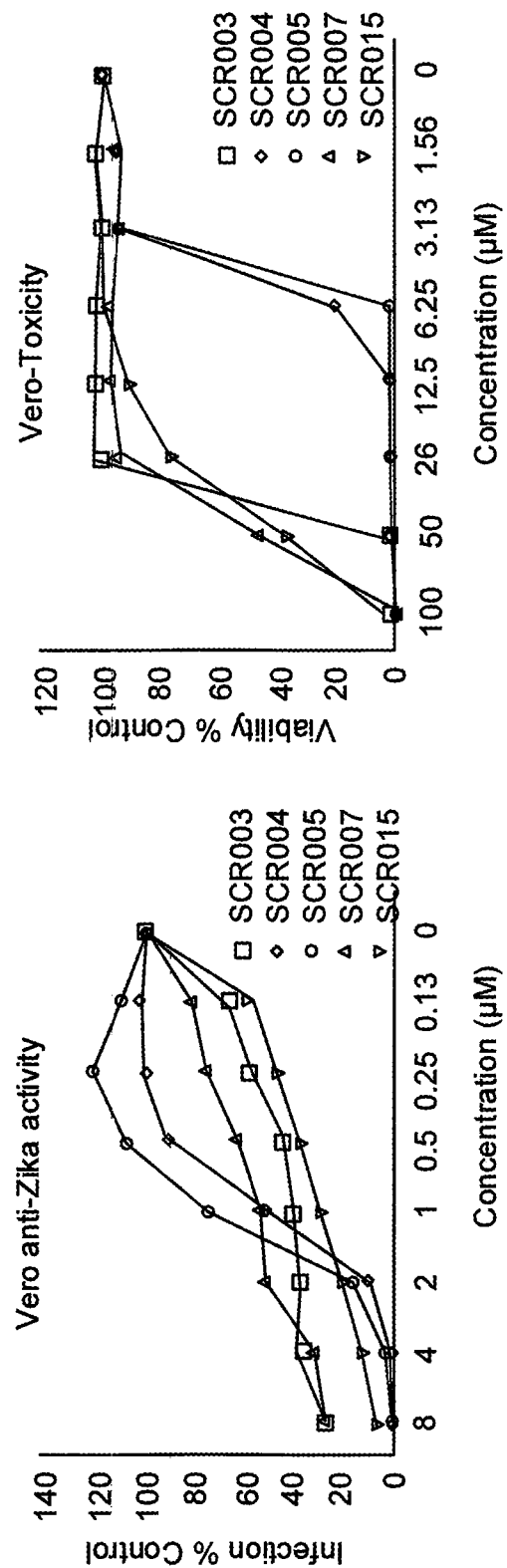
FIG. 7A is a graph showing the results of Vero cells that were treated with the indicated SCRs for 30 min at room temperature followed by infection with Zika RVPs. The number of GFP positive cells per well was quantified after imaging of whole wells via the Cytation5 imager.
FIG. 7B is a graph showing toxicity of SCRs in Vero cells. Vero cells were treated with the indicated SCRs and the cells were incubated for 72 h at 37° C. Cellular toxicity was measured using the CellTiter-Glo (Promega) luminescent viability assay. Data are mean of duplicate observations. One representative of three independent experiment is shown.

Anti-ZIKV Activity of SCRs. To determine the anti-ZIKV activity of the SCRs, Vero cells were preincubated with the compounds for 30 min at room temperature followed by infection with ZIKV GFP RVPs (FIG. 6A and FIG. 6B and FIG. 7A and FIG. 7B). Vero cells were chosen because they are highly permissive to infection by FLVs. The number of GFP-positive cells, which is a measure of virus infection, was determined 72 h postinfection. Compounds were screened for anti-ZIKV activity at 100 μM concentration, and those compounds that showed activity were further assayed in dose-response curves. In a fluorescent microscopy image of a single well of a 96-well plate, the number of GFP-positive cells increases with increasing dilution of SCR012, with the control (complete absence of SCR012) showing maximum infection. This same assay was then used to measure ZIKV infection in the presence of other SCRs. Six of the SCR receptors showed some level of activity against ZIKV infection in Vero cells, with SCR012 being the most potent (Table 1). Suramin, an FDA-approved drug for the treatment of trypanosomiasis, has recently been shown to have activity against several viruses, including ZIKV, by inhibiting different aspects of the virus life cycle, including attachment, fusion, and reverse transcription. As Suramin has been reported to interfere with ZIKV attachment, the same assay was conducted using Suramin for comparison. As demonstrated in FIG. 6B, Suramin showed a dose dependent inhibition of ZIKV infection, although with significantly lower potency than the screened SCRs. These findings establish the anti-ZIKV activity of this class of molecules. Data for selected compounds are shown in FIG. 6A and FIG. 6B (data for all compounds are provided in Supporting Information, FIG. 7A and FIG. 7B), and these data indicate that receptor SCR012 shows the best infection control followed by its monomeric counterpart, SCR001.

TABLE 1

Inhibitory Activity of SCRs against ZIKV Infection in Vero cells

| SCR | $IC_{50}$ (μM) | $TC_{50}$ (μM) | $K_a$ ($M^{-1}$) with α-Man$^a$ | $K_a$ ($M^{-1}$) with β-Man$^a$ |
|---|---|---|---|---|
| 1 | >100 | b | b | b |
| 2 | >100 | b | b | b |
| SCR001 | 0.36 ± 0.15 | b | b | $3.6 \times 10^4$ |
| SCR002 | 1.13 ± 0.23 | 5.43 | $1.4 \times 10^3$ | $5.4 \times 10^1$ |
| SCR003 | 1.31 ± 013 | 4.12 | c | c |
| SCR016 | >100 | b | b | $5.9 \times 10^2$ |
| SCR004 | 1.36 ± 0.27 | 46.11 | b | $2.4 \times 10^3$ |
| SCR005 | >100 | b | b | $3.7 \times 10^1$ |
| SCR006 | >100 | b | b | c |
| SCR007 | not soluble | b | b | b |
| SCR008 | >100 | b | b | b |
| 12 | >100 | b | b | b |
| 13 | >100 | b | b | b |
| 14 | >100 | b | b | b |
| SCR012 | 0.16 ± 05 | 36.2 | $2.6 \times 10^3$ | $1.7 \times 10^3$ |
| SCR015 | 12.37 ± 2.99 | 51.52 | b | b |
| Suramin | 44.02 ± 4.19 | >200 | b | B |

$^a$Association constant ($K_a$) between octyloxy pyranosides and SCRs from NMR titrations in $CD_2Cl_2$ at 298 K.
b Not determined.
c No detectable binding. $IC_{50}$, 50% inhibitory concentration; $TC_{50}$, 50% toxic concentration.

As Vero cells are derived from African green monkeys, the anti-ZIKV activity of SCRs in cells of human origin was also tested. $IC_{50}$ values for the six SCRs that were the strongest inhibitors of ZIKV infection in Vero cells using the same RVP assay. In HeLa, SCR 15 remains the most potent, with a similar $IC_{50}$ value (Table 2). This result confirms that the anti-ZIKV activity of the SCRs is maintained against human cell lines.

TABLE 2

Inhibitory Activity against ZIKV Infection and Toxicity of Select SCRs in HeLa Cells$^a$

| SCR | $IC_{50}$ (μM) | $TC_{50}$ (μM) |
|---|---|---|
| 3 | 0.45 ± 0.06 | 2.43 |
| 4 | 0.35 ± 0.09 | 2.51 |
| 5 | 0.56 ± 0.08 | 2.47 |
| 7 | 3.06 ± 0.59 | 17.59 |

TABLE 2-continued

Inhibitory Activity against ZIKV Infection
and Toxicity of Select SCRs in HeLa Cells[a]

| SCR | IC$_{50}$ (μM) | TC$_{50}$ (μM) |
|---|---|---|
| 15 | 0.24 ± 0.02 | 2.48 |
| 16 | 1.37 ± 0.18 | 2.22 |

[a]IC$_{50}$, 50% inhibitory concentration; TC$_{50}$, 50% toxic concentration.

Cytotoxicity and Cell Viability Study. For a compound to have therapeutic potential, it should have a high efficacy with minimum toxicity. To this end, the cytotoxic activity of the screened compounds was assessed in Vero cells. For this, Vero cells were incubated with different concentrations of the SCRs for 72 h (Table 1 and FIG. 7B). Cell viability was determined by measuring intracellular ATP levels using Cell Titer Glo assay. Cell viability curves were fit using Sigma plot and 50% toxic concentration (TC$_{50}$) of each compound was determined. Changes in cell morphology were also assessed via microscopy. As demonstrated in Table 1, the TC$_{50}$ values for all compounds that showed anti-ZIKV activity were several-fold higher than their anti-ZIKV IC$_{50}$, suggesting the potential for therapeutic exploration. For the most potent ZIKV inhibitor, SCR012, the TC$_{50}$ of 36.2 μM was greater than 220-fold higher than the IC$_{50}$ of 0.16 μM. For comparison, Suramin, which also demonstrated anti-ZIKV activity, had an IC$_{50}$ that was much higher than the SCRs. Cytotoxicity was also assessed in a cell line of human origin HeLa cells for the most active subset of SCRs. As demonstrated in Table 2 and FIG. 8A and FIG. 8B, the TC$_{50}$ values of the SCRs tested were several-fold higher than the IC50 value.

Figure 9A:
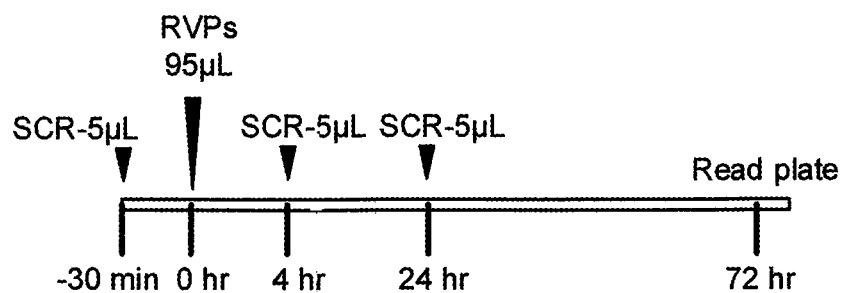
FIG. 9A shows a Schematic of time-of addition experiments. Cells were treated with SCRs either 30 min prior to infection or 4 and 24 h post ZIKV RVP infection. Plates were read 72 h post infection.
Figure 9B:
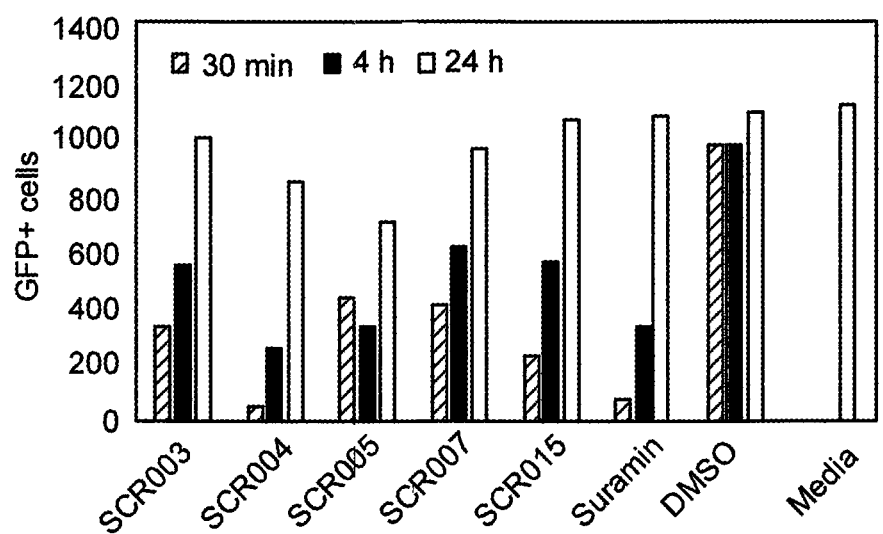
FIG. 9B shows the results of Vero cells were treated with the indicated compounds or DMSO control as indicated in part (A) above. The number of GFP positive cells was determined 72 h post infection.

Time-of-Addition Study. To gain insight into the mechanism via which the synthetic carbohydrate receptors inhibit ZIKV infection in the Vero cells, time-of-addition experiments were carried out. The compounds were added to the Vero cells either 30 min prior to infection or at 4 or 24 h postinfection. Plates were incubated for 72 h, and degree of infection was determined by the number of GFP+ cells. Suramin was also studied for comparison. As seen in FIG. 9A and FIG. 9B, the SCRs were most effective when added −30 min (prior to infection) and were less effective at 4 h and least effective at 24 h postinfection. These results were similar to those obtained with Suramin, a known inhibitor of virus attachment and infection, suggesting that (similar to Suramin) the SCRs act upon the virus by inhibiting early stages in the virus life cycle, most likely by preventing virus attachment and/or viral entry. These data are consistent, although not conclusive, with a proposed mechanism of activity, where the SCRs operate on the virus by binding glycans involved with viral docking. While these studies provide mechanistic insights regarding SCR mediated inhibition of ZIKV infection, inhibition of replicating ZIKV by the SCR supports the idea that the compounds are active in targeting multiple round virus replication as well.

Figure 10:
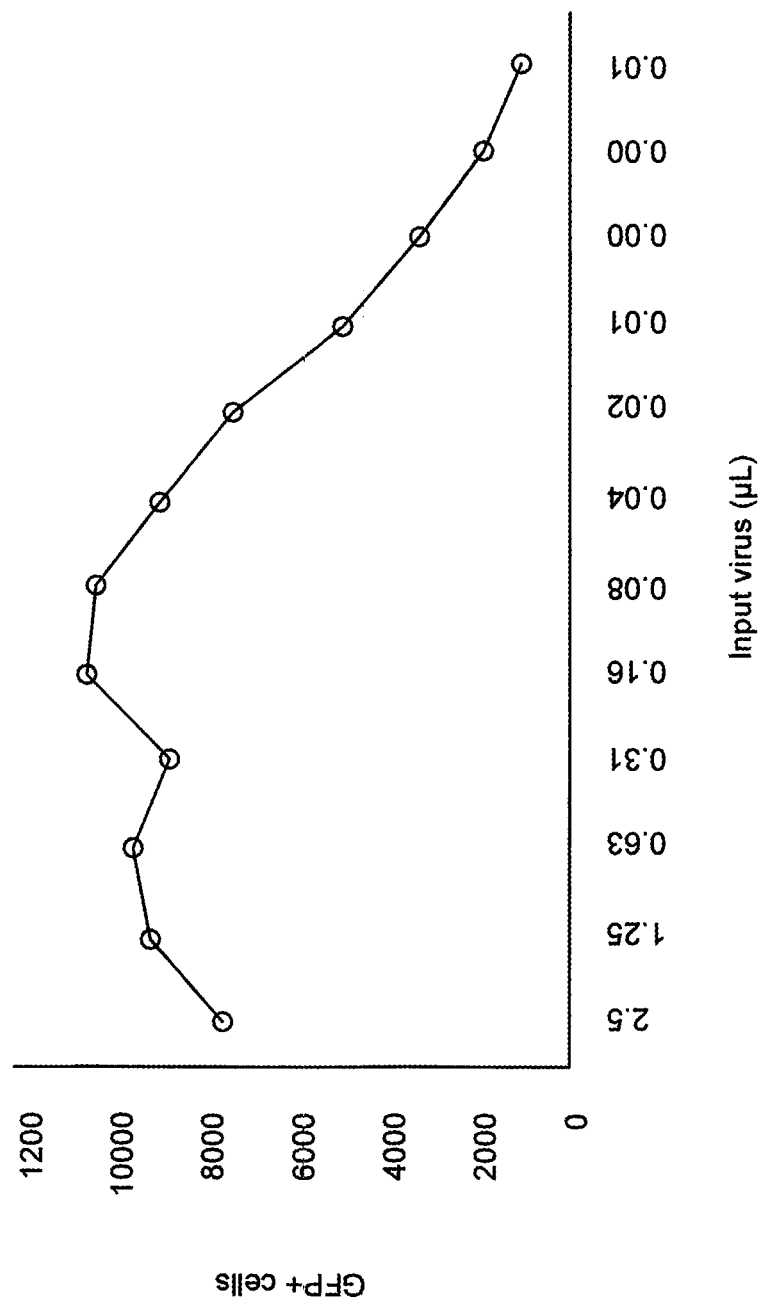
FIG. 10 depicts a graph showing the results of Vero cells were infected with serial dilutions of the virus stocks and cells were fixed 48 hrs post infection. Subsequently, cells were stained using 4G2 antibody. Images for the whole wells were acquired on Cytation 5 imaging reader and number of GFP+ cells per well-quantified using Gen5 Software.
Figure 11A:
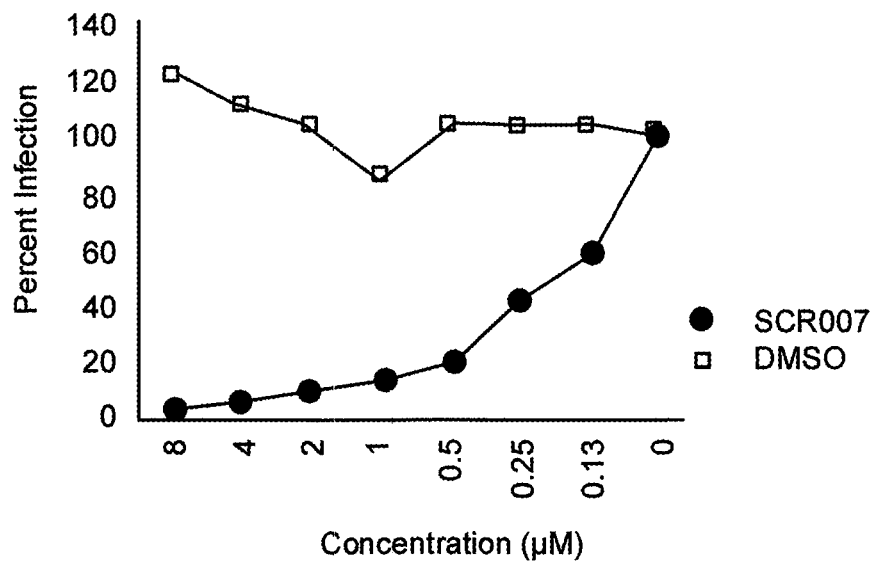
FIG. 11A depicts a graph showing results of Anti-ZIKV activity of SCR012, DMSO (control), against infectious ZIKV/Vero cells.
Figure 11B:
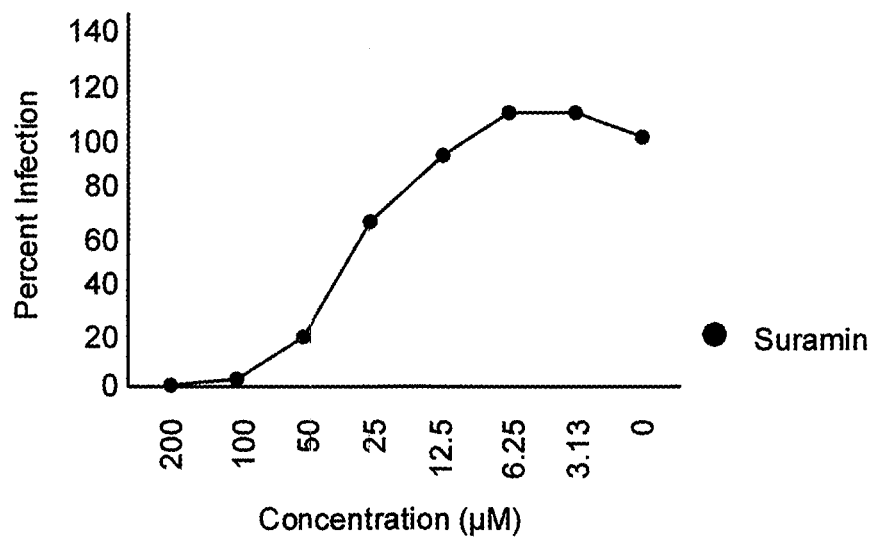
FIG. 11B depicts a graph showing results of Anti-ZIKV activity of Suramin against infectious ZIKV/Vero cells. Suramin for 30 min at room temperature, followed by infection with ZIKV. Cells were fixed and stained for ZIKV protein expression using the 4G2 antibody. Images of wells were acquired and number of GFP positive cells quantified. Data are mean±SD of triplicate observations. Data from one representative experiment are shown.

Inhibition of Infectious Virus with SCRs. As RVPs are only capable of initiating a single round of infection, the anti-ZIKV activity of a potent SCR012 was tested, using infectious Zika virus isolate PRVABC-59 as well as Suramin and DMSO as controls. Vero cells were preincubated with the compounds or DMSO followed by infection with a predetermined amount of ZIKV based on titration data (FIG. 10). Cells were then fixed and stained for ZIKV protein expression using the anti-FLV group antigen antibody 4G2. As shown in FIG. 11A and FIG. 11B, there is excellent inhibition of infectious ZIKV with SCR012 and to a lesser extent with Suramin (FIG. 11B). As expected, there was no inhibition seen with the DMSO control (FIG. 11A). Moreover, fluorescent microscopy analysis showed characteristic perinuclear staining pattern for ZIKV Envelope in DMSO treated but not SCR012 (8 μM) or Suramin (200 μM) treated cells. This suggests that the SCRs are not only capable of inhibiting RVPs but also infectious virus in multiple round infection assays.

Figure 12A:
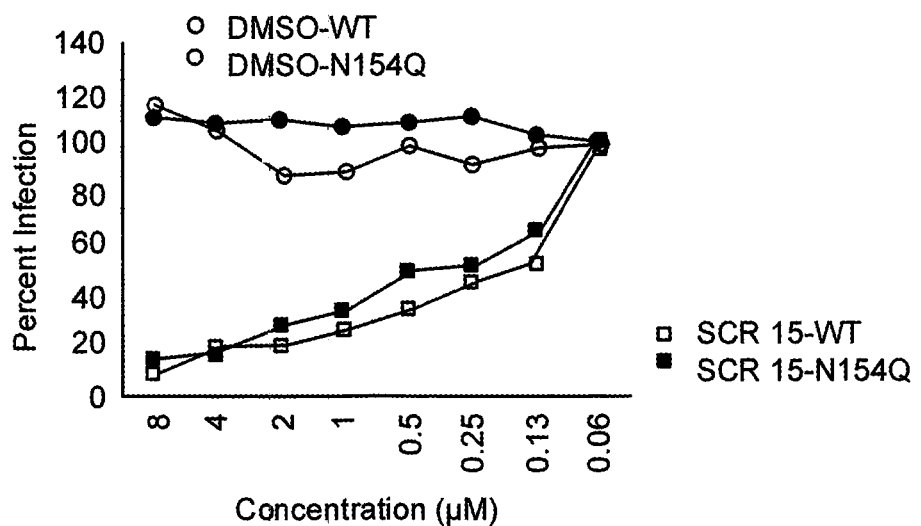
FIG. 12A depicts percent infection when Vero cells were treated with SCR012, DMSO control. Images of wells were acquired 72 h post infection and number of GFP positive cells quantified. Data are mean±SD of triplicate observations. Data from one representative experiment is shown. Abolishing the ZIKV Env glycosylation site N154 does not affect the inhibition mediated by SCRs.
Figure 12B:
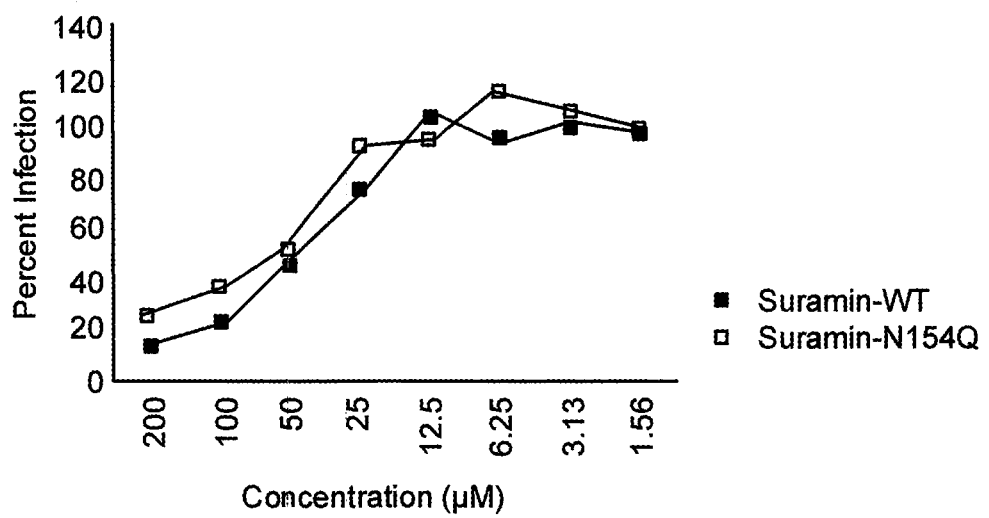
FIG. 12B depicts percent infection when Vero cells were treated with Suramin.

SCRs Do Not Affect the N154 Glycosylation Site of ZIKV Env. On the basis of this data, the SCRs were anticipated to be binding to N-mannosylated regions of Zika E protein. One such glycosylation site, N154, has been shown to be important for ZIKV cell surface binding and infection. To understand whether this site was involved in the antiviral activity of SCRs, the N154Q mutant was generated and analyzed inhibition mediated by SCR012. Interestingly, the N154Q mutant was inhibited with both SCR012 and Suramin, similar to WT RVPs (FIG. 12A and FIG. 12B). This suggests that glycosylation sites other than N154Q may be important for ZIKV attachment in Vero cells or that SCR012 may disrupt other virus-carbohydrate interactions. These results are strikingly similar to Suramin (control compound) suggesting that the mechanism of inhibition by SCRs may be similar to other entry inhibitors like Suramin. In support of this, it was shown for a related flavivirus, WNV that the presence of a single N-linked glycosylation sites on the prM or E protein was sufficient for virus tropism under certain conditions and in certain cell types.

Structure-Activity Analysis. In Vero cells, the best inhibitory activity corresponded to SCR012 and its monomer SCR001, respectively, indicating that the pyrrolic heterocycles and secondary amine groups are important for anti-ZIKV activity. Further, the improved activity of SCR012 compared to SCR001 (approximately double) shows the importance of multivalency for antiviral activity: SCR012 has approximately double the number of aminopyrrolic groups compared to SCR001. The synthetic intermediates did not show activity against ZIKV as anticipated, confirming the necessity of both the biaryl core and the pendant π-electron rich heterocycles. Receptors SCR002, SCR003 AND SCR004 which lack either a secondary amine group or a pyrrole ring, are less potent in Vero cells, although SCR002 is more potent than SCR001 in HeLa cells. However, furan-based multivalent receptor SCR015 shows activity far lower than that of its monomer SCR002, the reasons for which are not well understood. Imine- and amide-based receptors SCR005, SCR006, SCR007 AND SCR008 were not effective against ZIKV. These data indicate that both the aminopyrrolic groups and secondary amine linkers contribute to high ZIKV inhibition.

There appears to be a correlation between anti-ZIKV binding and the binding affinities of the SCRs for mannosides and glucosides (Table 1). While SCR001, SCR016 AND SCR012 are the strongest carbohydrate binders, SCR012 exhibits the best inhibitory activity. This result suggests that carbohydrate binding may play a role in the anti-ZIKV activity of the SCRs, but stronger inhibition of SCR012 may suggest that the effects of multivalency are magnified in the dense cellular environment compared to in solution. SCR016, which also binds α-mannosides strongly in solution but does not show any anti-Zika activity, further suggests the importance of pyrroles in cellular environments and that other glycans, besides mannosides, may be involved in viral entry. Other cell-surface glycans, such as GAGs, which are densely decorated with N-acetyl glucosamines, have a role in ZIKV infection and may also be involved in the anti-ZIKV activity of these compounds, so these studies are inconclusive with respect to the mechanism of inhibition, and clearly indicate that further research is needed to confirm the origin of anti-ZIKV activity.

Both SCR001 and SCR012 are active at submicromolar concentrations, which is comparable to the best anti-ZIKV agents known, and significantly more potent than Suramin. The $TC_{50}$ values are significantly greater than the $IC_{50}$ values, suggesting that these compounds merit further therapeutic exploration. On the basis of the importance of pyrrolic heterocycles, secondary amine groups, and multivalency on the potency of SCRs, this disclosure proposes that the anti-ZIKV activity can be enhanced by increasing multivalency by incorporating more pyrrolic heterocycles and secondary amine groups in future inhibitors. Time-of-addition studies imply a mode of action whereby the SCRs inhibit attachment of the virus to the host cell. Structure-activity analysis suggests that anti-Zika activity may correlate to glycan binding ability, and further studies are needed to confirm the mode of inhibition. These results confirm that SCRs have the potential to become powerful therapeutic agents in the battle against ZIKV, and they may act by a mechanism that has not yet been explored widely despite its therapeutic potential. Given the proposed mode of action of these SCRs, involving disrupting glycan-protein binding on the cell surface, it is worth evaluating SCRs as probes for studying virus-host interactions.

EXPERIMENTAL

Synthetic Procedures. General. All solvents, reagents, and starting materials were purchased from commercial sources and used without further purification unless otherwise noted. All solvents were dried using a JC Meyer solvent purification system. Aqueous solutions were prepared from nanopure water from a Milli-Q plus system, with a resistivity over 18 MΩ cm$^{-1}$. Chromatography purifications were performed using silica gel (60 Å, 70-230 mesh). Thin-layer chromatography (TLC) was carried out using aluminum sheets precoated with silica gel 60 (EMD 40-60 mm, 230-400 mesh with 254 nm dye). TLC plates were visualized by UV light and using charring solution (prepared by dropwise addition of conc.$H_2SO_4$ (5 mL) to a solution of $H_3PMo_{12}O_{40}$ (1 g) and $Ce(SO_4)_2$ (2 g) in water (95 mL)), alkaline $KMnO_4$ solution (prepared by dissolving $KMnO_4$ (2 g) and $NaHCO_3$ (4 g) in water (100 mL)), and heat as developing agents. All reactions were carried out under an inert atmosphere of Ar using standard Schlenk techniques unless otherwise noted. Reaction flasks were dried in an oven at 100° C. for 12 h. Compounds 1, 2, SCR001, SCR002, SCR003, SCR016, SCR004, SCR005, SCR006, SCR007, SCR008, 13, SCR012, 1,2-bis(prop-2-yn-1-yloxy)ethane, and 3,6,9,12,15,18-hexaoxaicosa-1,19-diyne were synthesized according to published literature procedures. Deuterated solvents were purchased from Cambridge Isotope Laboratories Inc. and used as received. NMR spectra were obtained on a Bruker AVANCE 300 MHz spectrometer. All chemical shifts are reported in δ units (ppm) using the solvent residual signal as an internal standard. The following abbreviations are used for signal multiplicities: s, singlet; br s, broad singlet; d, doublet; t, triplet; q, quartet; m, multiplet; dd, doublet of doublets. High-resolution electrospray ionization mass spectra were obtained on Agilent Q-TOF system. The purity data of all the compounds screened for anti-Zika activity were determined by the quantitative nuclear magnetic resonance (qNMR) method and were found to be >95% pure, except for compound SCR004, which could only be purified to 93%.

Synthesis of 1,2-Bis((1-((3',5,5'-tris(azidomethyl)-[1,1'-biphenyl]-3-yl)methyl)-1H-1,2,3-triazol-4-yl)methoxy)ethane (12). 1,2-Bis-(prop-2-yn-1-yloxy)ethane (200 mg, 1.5 mmol) and 1 (2.7 g, 7.2 mmol) were dissolved in 135 mL of anhydrous DMF. Then 15 mL of $H_2O$ was added, followed by sodium ascorbate (1.2 g, 6.0 mmol), $CuSO_4$ (49 mg, 0.30 mmol), and bathocuproinedisulfonic acid disodium salt (200 mg, 0.38 mmol). The mixture was stirred at room temperature under Ar for 24 h. The reaction mixture was concentrated under reduced pressure, triturated with $CHCl_3$, passed through a silica column, and eluted with $CHCl_3$ to remove $4N_3$. Then the column was flushed with 10% $MeOH/CHCl_3$, and the fractions were concentrated to give the crude, which was further purified by column chromatography ($SiO_2$, 1-1.5% MeOH in $CHCl_3$) to provide 12 (310 mg, 24%) as a pale-yellow oil. $^1H$ NMR (300 MHz, $CDCl_3$) δ=7.59 (s, 2H), 7.51 (s, 2H), 7.48 (s, 2H), 7.45 (s, 4H), 7.29 (s, 2H), 7.23 (s, 2H), 5.58 (s, 4H), 4.65 (s, 4H), 4.44 (s, 8H), 4.42 (s, 4H), 3.68 (s, 4H). $^{13}C$ NMR (75 MHz, $CDCl_3$) δ=145.08, 141.76, 141.09, 137.38, 137.06, 136.16, 127.22, 127.18, 127.01, 126.84, 126.76, 122.74, 69.75, 64.65, 54.41, 54.28, 53.80. HRMS (ESI): m/z calcd for $C_{40}H_{39}N_{24}O_2$ [M+H]$^+$ 887.3682, found 887.3688.

Synthesis of 1,18-Bis(1-((3',5,5'-tris(azidomethyl)-[1,1'-biphenyl]-3-yl)methyl)-1H-1,2,3-triazol-4-yl)-2,5,8,11,14,17-hexaoxaoctadecane (14). 3,6,9,12,15,18-Hexaoxaicosa-1,19-diyne (310 mg, 1.0 mmol) and 1 (1.87 g, 5.0 mmol) were dissolved in 90 mL of anhydrous DMF. Then 10 mL of $H_2O$ was added, followed by sodium ascorbate (825 mg, 4.17 mmol), $CuSO_4$ (34 mg, 0.21 mmol), and bathocuproinedisulfonic acid disodium salt (140 mg, 0.26 mmol). The mixture was stirred at room temperature under Ar for 24 h. The reaction mixture was concentrated under reduced pressure, triturated with $CHCl_3$, passed through a silica column, and eluted with $CHCl_3$ to remove $4N_3$. Then the column was flushed with 10% $MeOH/CHCl_3$, and the fractions were concentrated to give the crude, which was further purified by column chromatography ($SiO_2$, 1 to 3% MeOH in $CHCl_3$) to provide 14 (425 mg, 40%) as a pale-yellow oil. III NMR (300 MHz, $CDCl_3$) δ=7.62 (s, 2H), 7.51 (s, 2H), 7.48 (s, 2H), 7.46 (s, 4H), 7.29 (s, 2H), 7.23 (s, 2H), 5.60 (s, 4H), 4.66 (s, 4H), 4.44 (s, 8H), 4.42 (s, 4H), 3.71-3.54 (m, 20H). $^{13}C$ NMR (75 MHz, $CDCl_3$) δ=141.76, 141.12, 137.37, 137.06, 136.22, 127.20, 127.17, 126.98, 126.82, 126.76, 122.81, 70.51, 70.47, 70.29, 69.82, 64.70, 54.42, 54.30, 53.81. HRMS (ESI): m/z calcd for $C_{48}H_{54}N_{24}O_6$[M+H]$^+$ 1063.4731, found 1063.4737.

Synthesis of SCR015. $PPh_3$ (1.0 g, 3.9 mmol) was added to a stirring solution of 13 (500 mg, 0.51 mmol) in THF (30 mL) at room temperature and refluxed under Ar atmosphere for 1 h before the addition of furan-2-carbaldehyde (370 mg, 3.85 mmol) at room temperature. The reaction mixture was refluxed for an additional 48 h, cooled to room temperature, and concentrated under reduced pressure. The resulting residue was dissolved in MeOH (30 mL), and $NaBH_4$ (291 mg, 7.69 mmol) was added portionwise at room temperature. After stirring for 16 h, the reaction mixture was poured into ice, and the MeOH was evaporated. The residue was acidified with 3 N HCl at room temperature and washed with $CH_2Cl_2$ (3×40 mL). The aqueous layer was basified with 3N NaOH and extracted with $CH_2Cl_2$ (3×40 mL). The combined organic layers were dried over to anhydrous $Na_2SO_4$, filtered, and concentrated under reduced pressure to provide SCR015 (610 mg, 92%) as a brown gum. 1H NMR (700

MHz, CD$_2$Cl$_2$) δ=7.54 (s, 2H), 7.51 (s, 2H), 7.45-7.38 (m, 6H), 7.36 (s, 6H), 7.28 (s, 2H), 7.22 (s, 2H), 6.36-6.26 (m, 6H), 6.23-6.11 (m, 6H), 5.52 (s, 4H), 4.63 (s, 4H), 3.90-3.72 (m, 24H), 3.68-3.45 (m, 12H). $^{13}$C NMR (75 MHz, CD$_2$Cl$_2$) δ=153.75, 153.61, 145.59, 142.18, 141.92, 141.87, 141.61, 140.80, 140.54, 135.20, 127.53, 127.49, 126.94, 125.84, 122.56, 110.16, 107.22, 107.14, 70.50, 70.47, 69.74, 64.70, 54.14, 52.81, 52.52, 45.58, 45.52. HRMS (ESI): m/z calcd for C$_{74}$H$_{83}$N$_{12}$O$_{10}$ [M+H]$^+$ 1299.6350, found 1299.6341.

Biological Studies. Zika Reporter Virus Particles. The codon optimized version of ZIKV C-prM-E construct was synthesized using the complete ZIKV sequence available from the current outbreak in the Americas (accession number KU312312.1). The C-prM-E variant lacking the Eglycosylation site N154Q was constructed by site directed mutagenesis using forward primer 5'-ageggcat-gatcgtccaggacaccggccacgag-3' and reverse primer 5'-ctcgtggccggtgtcctggacgatcatgccgct-3' using the Quick Change II XL site directed mutagenesis kit (Stratagene). The entire C-PrM-E region was sequenced to verify the presence of the mutations and authenticity of insert. ZIKV RVPs were generated using the protocol described below. 293T cells stably expressing the Zika virus CprME (293T-CPrME-F6) were transfected with the plasmid containing the subgenomic GFP expressing replicon derived from lineage II strain of WNV. For generation of N154Q RVPs, 293T cells were transfected with plasmids C-PrME-N154Q and subgenomic GFP replicon at a ratio of 1:1. Transfections were performed using the Turbofect transfection reagent (ThermoFisher) strictly following the manufacturer's recommendations. The RVPs were harvested 48 h post-transfection, aliquoted, and stored for future use.

Titration of RVPs. Vero cells were plated in 96-well, clear-bottom black plates at 5000 cells per well. Serial 2-fold dilutions of RVPS were prepared in DMEM-10 medium and added to Vero cells starting with the highest dose of 50 µL/well. For each RVP dilution, infections were conducted in duplicates/triplicates and cells incubated with RVPs for 72 h. Thereafter, the plates were fixed with 4% formalin/PBS and images of whole wells acquired using the Cytation 5 imaging system (BioTek). The number of GFP+ cells were counted using the Gen5 imaging software which provides a read out of the number of GFP-positive cells per well. The optimal virus dose for infection experiments was then determined from the titration curves.

Inhibition of Zika Infection Using Synthetic Carbohydrate Receptors. Vero and HeLa cells were obtained from ATCC, and cultured in DMEM supplemented with 10% FBS and penicillin, streptomycin, and glutamine. Cells were plated in 96-well, clearbottom black plates at 5000 cells per well. Stock solutions of the compounds were made in DMSO at 10 mM concentration. Further dilutions of the compounds were made in cell culture media. Different compounds were added at the indicated concentrations in duplicates/triplicates and cells incubated with the compounds for 30 min at room temperature. Thereafter, a predetermined amount of Zika RVPs that yields up to 1000 GFP+ cells per well was added to the plates. Cells treated with the same amount (in µL) of DMSO as the input volume of the compounds and infected with Zika RVPs were used as normalization control for determination of 100% infection. Plates were incubated for 72 h at 37° C., after which images acquired using the Cytation5 imaging system (BioTek). The experiment was repeated three times, and inhibition curves were generated for each experiment using the Sigma plot software and 50% inhibitory concentration (IC50) value for each compound were determined.

Inhibition Studies with Infectious ZIKV, PRVABC59. The ZIKV isolate PRVABC59 derived from a human serum specimen from Puerto Rico in December 2015 was obtained from ATCC and propagated in Vero cells following the manufacturer's recommendations. The virus stocks were titrated in Vero cells using fluorescent microscopy. Briefly, Vero cells were infected with serial dilutions of the virus stocks and cells fixed with 4% formaldehyde/PBS 48 h post infection. Subsequently cells were stained using 4G2 antibody (MAB10216, Millipore) followed by Alexa 488 conjugated secondary antibody (Invitrogen). Images for the whole wells were acquired on a Cytation 5 imaging reader, and the number of GFP+ cells per well quantified using Gen5 Software. For subsequent experiments, a predetermined amount of virus that yields ~2000-3000 GFP+ cells per well was used.

For compound inhibition studies with infectious virus, Vero cells were plated in 96-well, clear-bottom black plates at 7500 cells per well. Cells were incubated with different concentrations of the SCRs for 30 min at room temperature as indicated above. Cells were then infected with a predetermined amount of ZIKV PRVABC59 isolate that yields 2000-3000 GFP+ cells per well determined from titration curves above. Thereafter, cells were fixed and number of infected cells determined via 4G2 antibody staining followed by Cytation5 imaging as above. The experiment was conducted in triplicate wells, and the entire experiment was repeated.

Determination of Cellular Toxicity. Vero or HeLa cells were plated in 96-well clear bottom white plates at 5000 cells per well. Different compounds were added at the indicated concentrations in duplicates, and the cells were incubated for 72 h at 37° C. Cellular toxicity was measured using the CellTiter-Glo (Promega) luminescent viability assay that is based on quantitation of the ATP in cells, an indicator of metabolically active cells. Data was normalized to cells treated with DMSO as being 100% viable. Toxicity curves were generated using the Sigma plot software by fitting curves using Sigmoidal logistic 4 Parameter nonlinear regression and TC50 concentrations determined for the compounds from the curves.

Time-of-Addition Experiments. ZIKV virus RVP inhibition assays in Vero cells were conducted as described above, with slight modification. Cells were infected with a predetermined amount of ZIKV RVPs in a volume of 95 µL, and the compounds were added either 30 min prior to infection or 4 or 24 h postinfection in a volume of 5 µL. The plates were fixed 72 h post infection, and the number of GFP+ cells per well were determined using the Cytation5 imaging system.

Additional SCRs

Several of the disclosed SCRs showed improved selectivity relative to SCR001. SCR017 (3-pyrrole) prefers β-Glc, while SCR021 (3-pyridine) and SCR022 (2-phenol) prefer β-Glc. Similarly, SCR018 (2-indole) and SCR020 (2-pyridine) uniquely bind α-Man, while SCR019 (3-indole) prefers β-Man. In some cases, higher stoichiometry equilibria, such as 1:2 or 2:1 SCR.glycan complexes that occur with positive cooperativity, drive the binding preferences. These binding results reveal the central role of the CH . . . π interactions in determining the affinity towards different glycans. Considering the biological role of cell-surface glycans, the binding of these SCRs to different monosaccharides could be exploited for developing applications that need specific glycan targeting agents.

In the biochemical context, selectivity refers to the ratio between the binding affinities ($K_a$s) of a receptors to different ligands, and selectivity, rather than specificity, is a more relevant criteria in glycan binding since even natural lectins are promiscuous and will bind many glycans weakly. An approach that has been adopted widely in modulating SCR affinity is to vary the heterocyclic units that form C—H . . . $\pi$ and H-bonding interactions with the glycan guests. Subtle differences in heterocycle composition and linkage position have been shown to have profound consequences on selectivity. For example, prior studies have explored extensively the effect of varying heterocyclic motifs of certain acyclic tripodal SCRs on the binding affinity and selectivity towards different carbohydrates. These studies found that certain compounds with three 2-amino-4,6-dimethyl-pyridine groups showed cumulative $K_a$s to β-Glc of $6.4\times10^7$ $M^{-2}$. When one of three 2-amino-4,6-dimethyl-pyridine groups of this SCR was replaced by an amino-crown ether, the selectivity for β-Glc over α-Glc was >$5\times10^6$ in $CDCl_3$. When two of three 2-amino-4,6-dimethyl-pyridine groups of this SCR were substituted with amino group containing either 5-imidazole (Mazik, Beilstein Journal of Organic Chemistry 2010, 6, No. 9), 3-indole or isobutyl (Mazik, J. Org. Chem., 2010, 75, 6416-6423) groups, the selectivity changed to β-Gal with cumulative $K_1$s of $10^7$ to $10^9$ $M^{-2}$ in $CDCl_3$. Similarly, a tripodal SCR that possesses three 2-indolyl-amino groups bound β-Gal preferentially with selectivity as high as $2.4\times10^3$:1 β-Gal:α-Gal and $2.0\times10^3$:1 β-Gal:β-Glc in $CDCl_3$. (Rosien, Org. Biomol. Chem., 2013, 11, 6569) However, the corresponding 3-indole derivative bound only β-Glc with a K. of $6.5\times10^2$ $M^{-1}$ in $CDCl_3$, confirming the impact of the linkage position on selectivity. (Rosien, Org. Biomol. Chem., 2013, 11, 6569) Similarly, other studies have systematically investigated the effect of different heterocycles on binding affinity and selectivity of other tripodal SCRs towards different glycans. For example, an SCR that has three primary amine groups with no heterocycle showed binding to β-Glc with the intrinsic median binding concentration ($BC^0_{50}$) of 3690 μM in $CDCl_3$, (Nativi, J. Am. Chem. Soc. 2007, 129, 4377-4385) whereas the 2-pyrrole amine-based SCR showed selectivity towards β-GlcNAc ($BC^0_{50}$=18 μM) in $CDCl_3$ as 44:1 β-GlcNAc:α-Gal and 2:1 β-GlcNAc:α/β-Man. (Nativi, J. Am. Chem. Soc. 2007, 129, 4377-4385) Attaching an acetal group to the pyrroles resulted in an SCR with the highest affinity for β-Man, with $BC^0_{50}$ of <1 μM in $CDCl_3$. (Nativi, Org. Lett., Vol. 9, No. 23, 2007) Thus, the need to further explore carbohydrate-binding selectivity is still of interest from both a fundamental perspective and for developing SCRs for biomedical applications. The approach of varying the heterocycle and point of attachment to the biaryl core was adopted to build a library of tetrapodal SCRs to investigate how the heterocycles appended by secondary amine linkages affect $K_a$ and selectivity towards a series of glycan guests. Binding of these seven SCRs with five octyloxy pyranosides was explored by $^1H$ NMR titrations, electrospray ionization (ESI) mass spectrometry, and molecular modelling, revealing three new SCRs that bind mannosides specifically as a result of multivalent cooperative binding. This study shows that the preferential binding of tetrapodal SCRs with a biaryl core for mannosides can be enhanced by the judicious choice of heterocycle, which could lead to SCR-based drug delivery agents, therapeutics, and sensors.

SCRs SCR017SCR023 (FIG. 1) were synthesized from common intermediate 1 in yields ranging from 34% to quantitative using the disclosed standard three-step one-pot protocol, which involves a Staudinger amination of tetraazide 1 to give the corresponding iminophosphorane intermediate, subsequent aza-Wittig reaction with the appropriate aryl/heteroaryl aldehyde, followed by reduction of the resulting imine with sodium borohydride. These SCRs vary from SCR001 in either the heterocycle or position of heterocycle attachment, while maintaining the secondary amine group and the biaryl core, which should be maintained to bind glycans in $CD_2Cl2$ and to inhibit ZIKV infection. The heterocycles include 2- or 3-pyrrole, 2- or 3-pyridine, 2- or 3-indole, and 2- or 3-phenol. The SCRs were characterized by $^1H$ NMR, $^{13}C$ NMR, and high-resolution mass spectrometry, and all spectroscopic data were consistent with the proposed structures. Binding between the seven SCRs and the five octyloxy glycans (FIG. 12C) is described below, which was studied by $^1H$ NMR titrations, ESI mass spectrometry, and molecular modelling. This disclosure illustrates the data and analysis using the examples of SCR019.β-Man and SCR020.α-Man.

Binding Studies by Mass Spectrometry

Figure 13B:
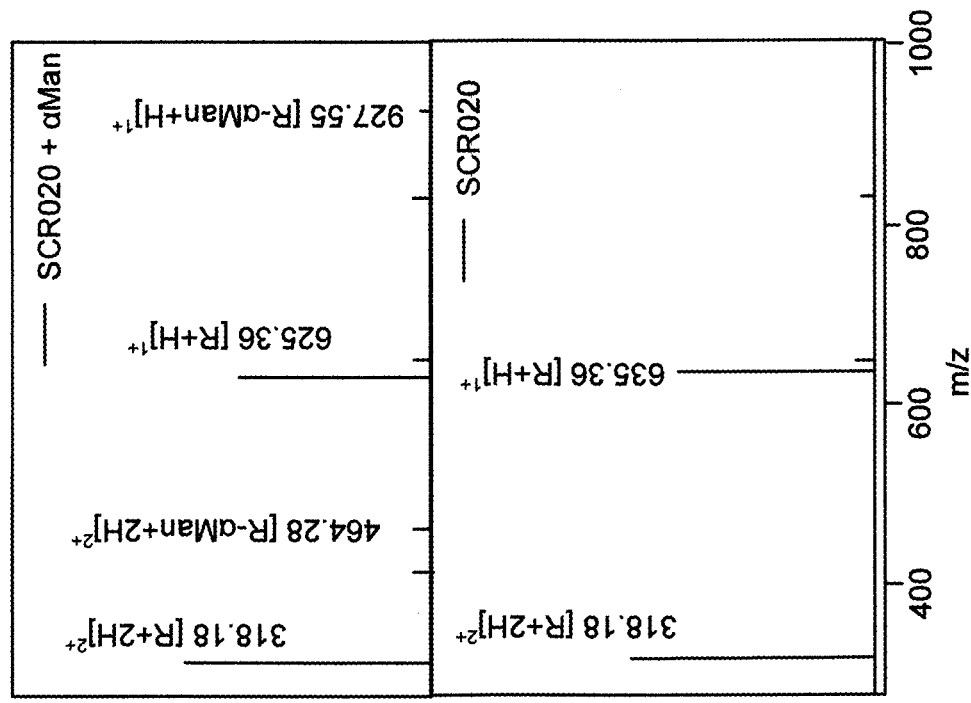
FIG. 13B is a ESI mass spectrum of a 1:1 mixture (0.5 μM, 40%:60% v/v $CH_2Cl_2$:$CH_3CN$) of SCR020 and α-Man. Bottom: ESI mass spectrum of SCR020 alone (1.0 μM, 40%:60% v/v $CH_2Cl_2$:$CH_3CN$), where R=Receptor. Peaks were assigned using Compass Data Analysis Software (Bruker)
Figure 13A:
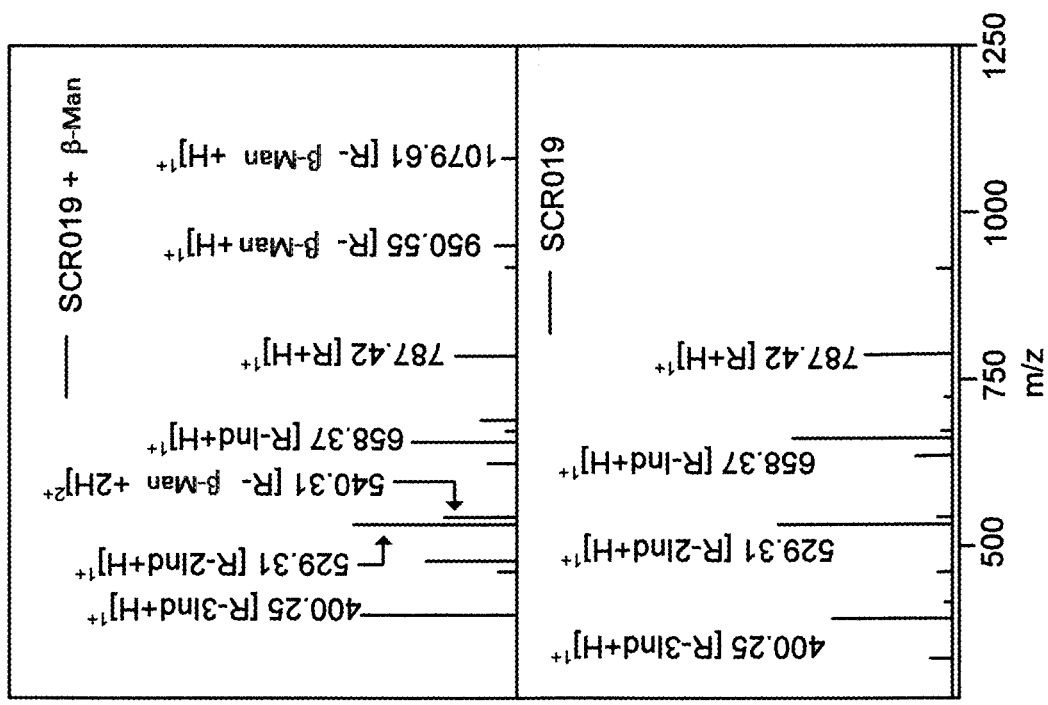
FIG. 13A depicts ESI mass spectrum of a 1:1 mixture (0.5 μM, 40%:60% v/v $CH_2Cl_2$:$CH_3CN$) of SCR019 and β-Man. Bottom: ESI mass spectrum of SCR019 alone (1.0 μM, 40%:60% v/v $CH_2Cl_2$:$CH_3CN$)

Binding of the SCRs to the glycans was first studied by positive ion ESI mass spectrometry because the presence of ions corresponding to the SCR.glycan complex confirms supramolecular association. As fragmentation peaks of the SCRs taken in the absence of glycan are necessary to interpret the mass spectra of the SCR.glycan complexes, solutions containing only the SCRs were subjected to mass spectrometry analysis. 1 μM solutions of SCRs, were prepared by diluting 1 mM of the SCRs stock solutions in $CH_2Cl_2$ with 40% $CH_2Cl_2$ in $CH_3CN$. These solutions were then injected via direct infusion into the spectrometer with a syringe pump. The fragmentation patterns showed ions corresponding to the loss of heteroaryl arms via cleavage of the CN bond, which is a favored cleavage point for electron-rich heterocycles because of the stability of the resulting benzylic anions. Consistent with this, the ESI mass spectrum of SCR019 shows the $[M+H]^{1+}$ molecular ion in addition to $[M+H]^{n+}$ ions corresponding to loss of either one or more 3-indolebenzylic groups (FIG. 13A, bottom). In the case of SCR020.α-Man, which has electron poor pyridine heterocycles, $[M+H]^{1+}$ and $[M+2H]^{2+}$ fragment ions were observed (FIG. 13B, bottom), but ions corresponding to the cleavage of the CN bond were not prominent, likely because this fragement would not be stabilized in electron poor heterocycles. Similar fragment ions were observed in the case of all other SCRs containing electron poor heterocyclic arms). After understanding the fragmentation of SCRs, the mass spectrometry of the SCR.glycan complexes was studied. 1 μM solutions of glycans in 40% $CH_2Cl_2$ in $CH_3CN$ were prepared, and they were mixed one-to-one with the 1 μM solution of SCRs in 40% $CH_2Cl_2$ in $CH_3CN$. The mixture was then injected into the spectrometer via direct infusion with a syringe pump. Simulation of the expected masses and the isotopic distributions of the complexes, the individual components, and their fragmentation patterns was performed with Compass Data Analysis software (Bruker) to identify peaks corresponding to supramolecular association between the SCRs and the glycans. In the case of SCR019.β-Man (FIG. 13A, top), the ions corresponding to [SCR019.β-Man+H]$^{1+}$, [SCR019.β-Man+2H]$^{2+}$ and the ion [SCR019-Ind.β-Man+H]$^{1+}$, resulting from loss of one indole-benzyl group, were observed. The [SCR019+H]$^{1+}$ ion and 1+ ions of SCR019, with the loss of one or more indole-benzyl groups, were also observed. In the case of SCR020.α-Man (FIG. 13B, top), [SCR020.α-Man+H]$^{1+}$ and [SCR020.α-Man+2H]$^{2+}$ were observed in addition to 1+ and 2+ molecular ions of SCR020. Analysis of the mass spectra of all other SCR.glycan combinations displayed similar ions indicating supramolecular complexation. These studies were repeated for all SCR.glycan mixtures, and revealed that all SCRs bind all glycans assayed to some extent, forming 1:1 SCR.glycan complexes. It should be noted, however, that these MS experiments reveal little about strength of association, and other analytical techniques are required to determine binding affinity ($K_a$) and selectivity of the SCRs towards the different glycans.

Determination of Kas by NMR Titrations

Figure 14A:
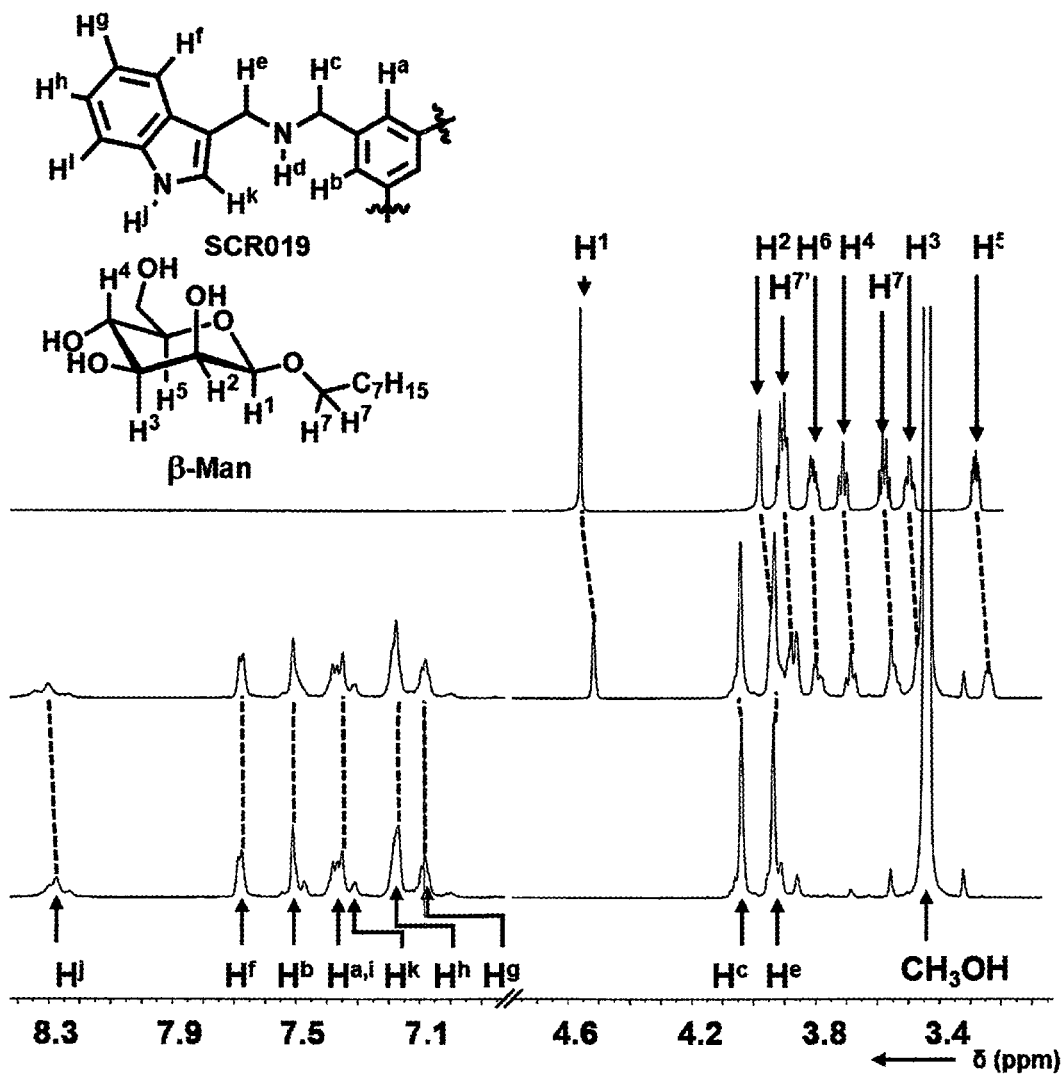
FIG. 14A shows a $^1H$ NMR (800 MHz, 1% $CH_3OH$ in $CD_2Cl_2$, 298 K) of β-Man (16 mM, top), a 2:1 ratio of β-Man:SCR019 (middle), and SCR019 (1 mM, bottom). Dashed lines track the shifts of peaks upon mixing of SCR019 and β-Man.

The supramolecular association between the C1-octyloxy glycans and the SCRs were determined by NMR titrations at 298 K in $CD_2Cl_2$, since this technique is widely used for host-guest binding processes with association constants ranging from 1 to $10^5$ $M^{-1}$. For SCR017, SCR019 and SCR023, 0.5% $CD_3OD$, 1% $CH_3OH$, and 4% $CD_3OD$, respectively, were added to the titration to increase the solubility of the SCRs. Prior to titration, dilution experiments were performed for all SCRs at a concentration range of 1 mM 25 µM to determine if they undergo dimerization, and if the observed change in chemical shift ($\Delta\delta$) was >0.02 ppm, the data were fit to a dimerization model to determine the dimerization constant, $K_d$. Dimerization was observed only for SCR001, and SCR023. All other SCRs did not undergo dimerization at the concentration range studied. Following the dilution experiments, the $^1$H NMR titrations were performed by adding a 6.25 µL aliquots of 16 mM solution of glycans to a 5004 (1 mM) solution of the SCRs, and the additions were continued until a 30:1 glycan:SCR ratio was obtained. As illustrative examples, the $^1$H NMR spectra of SCR019.β-Man and SCR020.α-Man are discussed here, while the $^1$H NMR titrations for the other complexes are provided in the Supporting Information. These combinations are representative examples of Mannoside selectivity, SCR019 is selective for Mannosides with a preference for the β-anomer, whereas SCR020.α-Man possessed the highest $K_a$ measured with tetrapodal receptors. FIG. 14A shows the $^1$H NMR of β-Man (top), SCR019 (bottom), and a 2:1 ratio of SCR019 and β-Man (middle) in 1% $CH_3OH$ in $CD_2Cl_2$ at 298 K. For β-Man, the largest shift upon association was for the peak corresponding to the $H^4$ proton, with $\Delta\delta=0.13$ ppm downfield, and the second largest shift was for the peak corresponding to $H^6$, with $\Delta\delta=0.11$ ppm downfield. The peak shifts are attributed to the change in chemical environment as a result of reversible supramolecular association between glycan and SCR that is occurring in the fast exchange regime. When involved in C–H . . . π interactions with aryl rings of SCRs protons shift upfield, so these results suggest that these hydrogens do not form C—H . . . π interactions with SCR019. In contrast, the peaks corresponding to $H^1$ and $H^5$ of β-Man shift downfield 0.03 and 0.04 ppm, respectively, upon association, suggesting the formation of C-H . . . π interactions with the aromatic rings of SCR019. Significant shifts were also observed for the SCR protons upon complexation. The largest shift was 0.20 ppm downfield for the peak corresponding to the indole N—H proton, indicating their participation in H-bonding with the glycans. The peak representing aromatic proton $H^k$ shifted downfield 0.06 ppm, and the peak corresponding to $H^f$ shifted 0.02 ppm upfield.

Figure 15A:
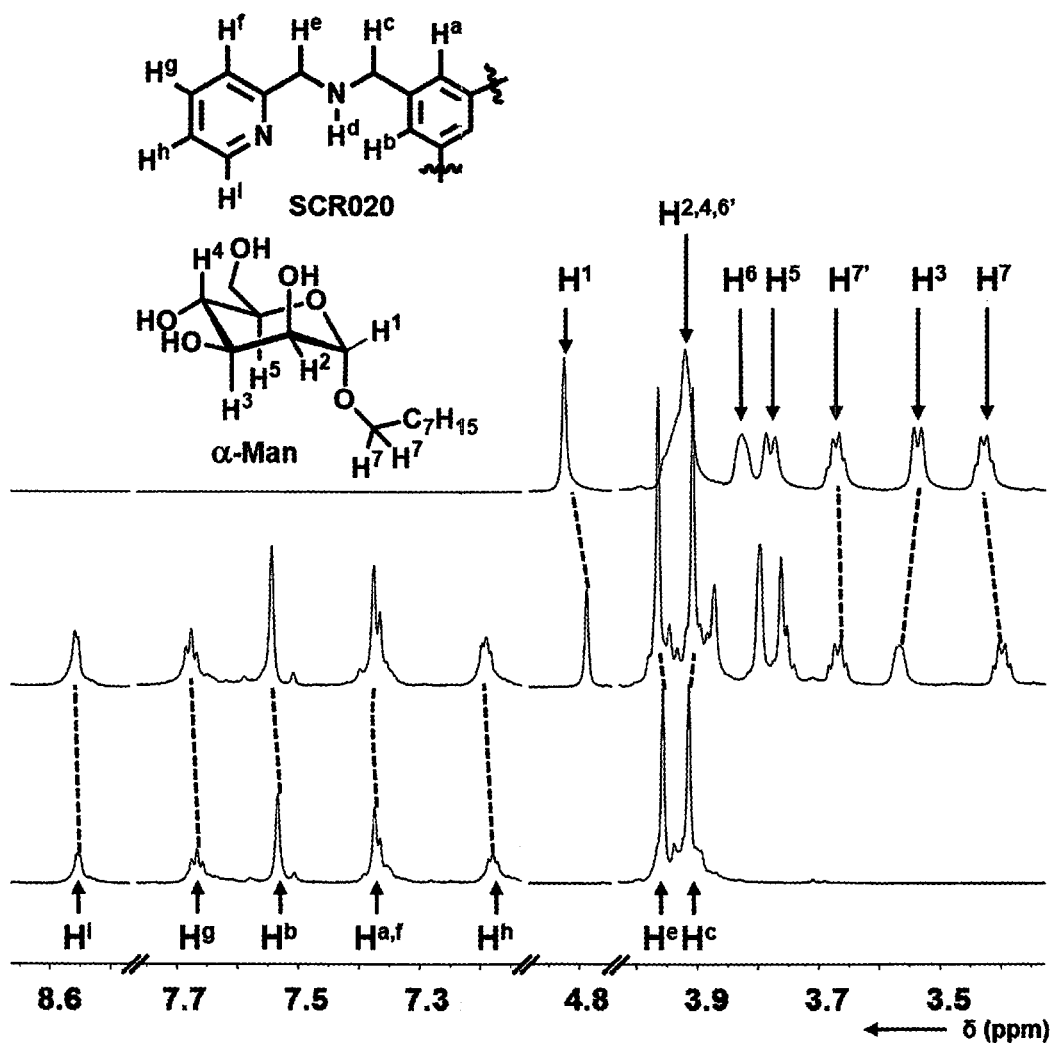
FIG. 15A shows $^1H$ NMR (800 MHz, $CD_2Cl_2$, 298 K) of α-Man (16 mM, top), a 2:1 ratio of α-Man:SCR020 (middle) and SCR020 (1 mM, bottom). Dashed lines track the shifts of peaks upon mixing of SCR020 and α-Man.

FIG. 15A shows the $^1$H NMR spectra of α-Man (top), SCR020 (bottom), and a 2:1 ratio of α-Man:SCR020 (middle) in $CD_2Cl_2$ at 298 K. The titrations were performed as described above, and significant shifts ($\Delta\delta$>0.02 ppm) were observed for both glycan and SCR peaks. Although $\Delta\delta$>0.02 ppm may seem small, the shifts are significant for such noncovalent interactions between SCRs and glycans. The largest shift for α-Man upon complexation was found for $H^3$ with 0.06 ppm upfield shift as a result of probable CH it interactions with the SCR. The other significant shift was found for the peak corresponding to $H^1$ with $\Delta\delta=0.03$ ppm downfield as observed for the peaks corresponding to $H^4$ and $H^6$ of β-Man in the case of SCR019.β-Man. Similarly, downfield shifts of $\Delta\delta=0.03$ ppm were observed for the peaks corresponding to the aromatic protons $H^b$, $H^e$, $H^g$ and $H^h$ of the SCR host. Titrations were repeated for all SCR.glycan combinations, and they are presented in the Supporting Information. Among all SCR.glycan complexes, the largest shift for CH proton of a glycan was $\Delta\delta=0.15$ ppm downfield for the peak corresponding to $H^6$ of α-Man in SCR017α-Man complex, and the largest shift for the aromatic proton was $\Delta\delta=0.17$ ppm downfield for $H^f$ of the 3-pyrrole ring of the SCR017.α-Man titration. Similarly, the largest shift for the N—H proton of pyrrole or indole heterocycle was $\Delta\delta=0.74$ ppm downfield for N—H proton of 2-indole in the case of SCR018.β-Gal complex. The shifts are within the typical range for the protons of glycan and SCR upon complexation ($\Delta\delta=0.02$-1 ppm), are strong evidence for SCR.glycan complex formation, and provide some insight on the binding geometry. $^1$H NMR of most of the titrations presented significant shifts for SCR and glycan peaks upon mixing, indicating supramolecular association. It should be noted also that the spectra of several of the SCR.glycan combinations (e.g. SCR018.β-Glc, SCR019α-Glc, SCR021.α-Glc, SCR022.α-Glc, SCR021.β-Gal, SCR022.β-Gal) did not show peak shifting upon mixing, indicating that no substantial binding was occurring. This result is significant because these data suggest that the SCRs reported here are selective—i.e. they do not bind all sugars—which is a significant and important departure from all previously studied tetrapodal SCRs, which are generally promiscuous binders.

Figure 15B:
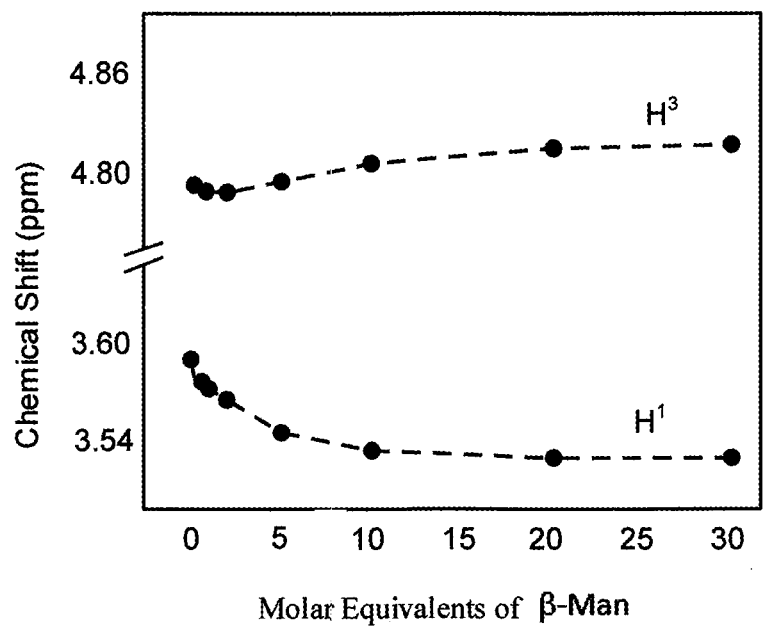
FIG. 15B shows the shift of the NMR peaks corresponding to protons $H^1$, $H^4$, $H^5$ and $H^6$ of α-Man at 298 K, with bullets and lines representing the experimental data and the fit from a 1:2 SCR.glycan binding model, respectively.
Figure 15C:
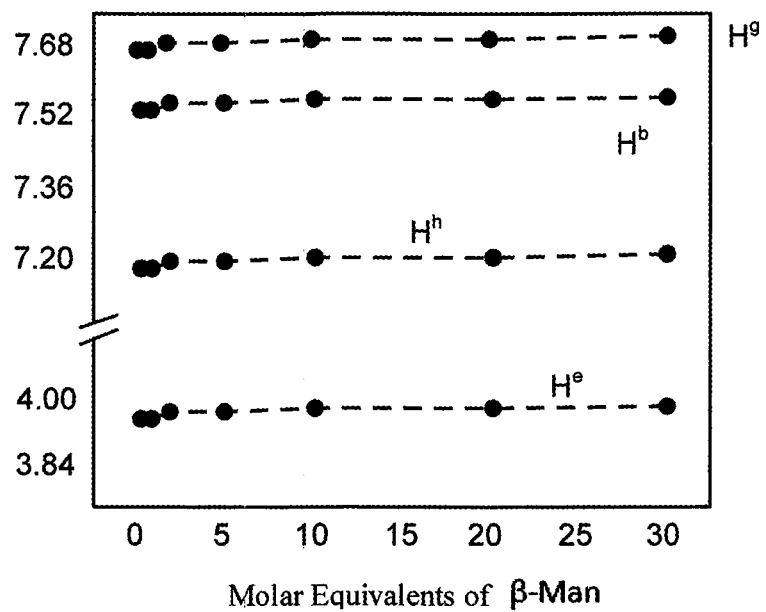
FIG. 15C shows the shifts of the NMR peak of the $H^a$, $H^b$, $H^f$ and $H^k$ protons of SCR020 upon addition of α-Man in $CD_2Cl_2$ at 298 K, with bullets and lines representing the experimental data and the fit from a 1:2 SCR.glycan binding model, respectively.

FIG. 15B shows the shift of the NMR peaks corresponding to protons $H^1$, $H^4$, $H^5$ and $H^6$ of α-Man at 298 K, with bullets and lines representing the experimental data and the fit from a 1:2 SCR.glycan binding model, respectively. FIG. 15C shows the shifts of the NMR peak of the $H^a$, $H^b$, $H^f$, and $H^k$ protons of SCR020 upon addition of α-Man in $CD_2Cl_2$ at 298 K, with bullets and lines representing the experimental data and the fit from a 1:2 SCR.glycan binding model, respectively.

Figure 14B:
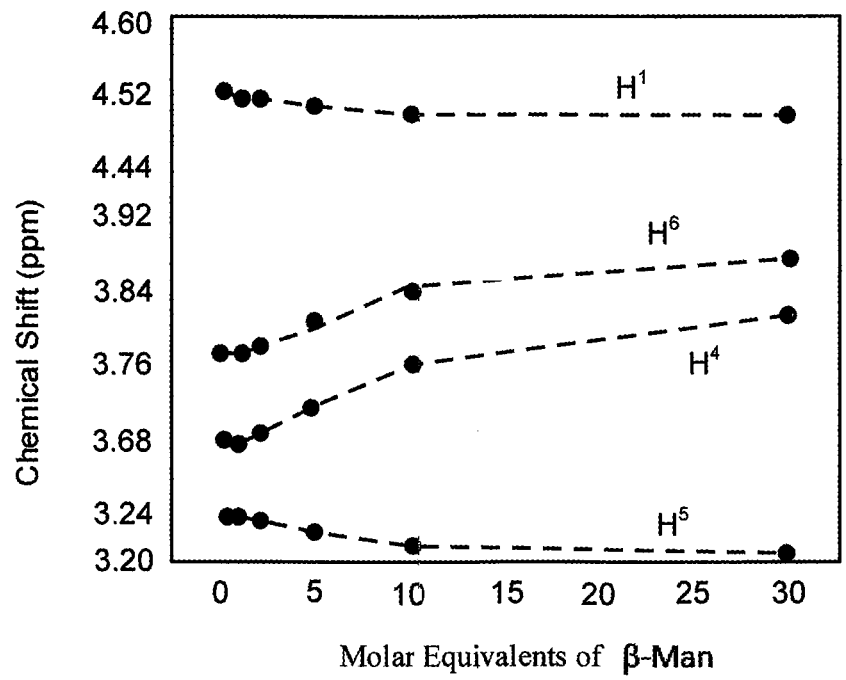
FIG. 14B shows the shift of the NMR peaks for protons $H^1$, $H^4$, $H^5$ and $H^6$ of β-Man at 298 K, with bullets and lines representing the experimental data and the fit from a 1:2 SCR.glycan binding model, respectively.
Figure 14C:
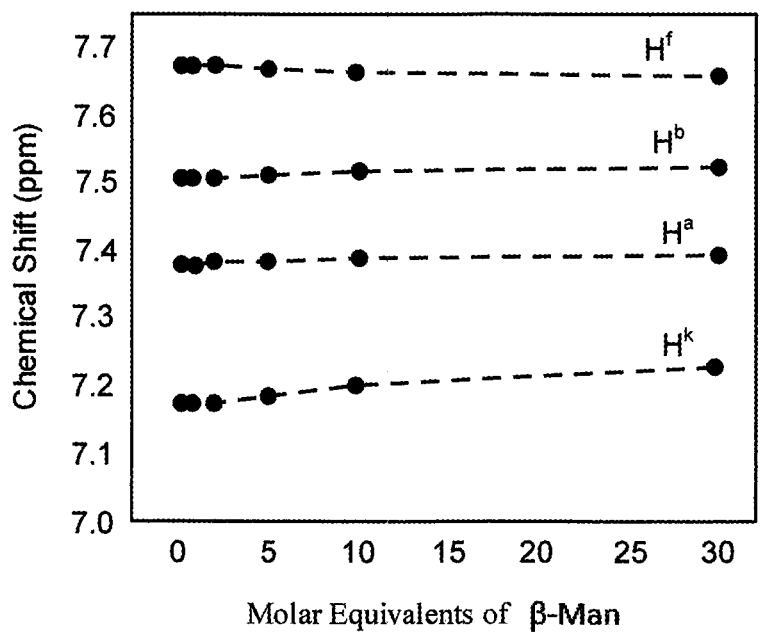
FIG. 14C shows the shifts of the NMR peak of the $H^a$, $H^b$, $H^f$, and $H^k$ protons of SCR019 upon addition of β-Man in $CD_2Cl_2$ at 298 K, with bullets and lines representing the experimental data and the fit from a 1:2 SCR.glycan binding model, respectively.

These NMR titrations were used to quantify the $K_a$s for the supramolecular binding between the glycans and the SCRs. To determine the $K_a$s, $^1$H NMR chemical shifts were fit to binding models that considered the different possible equilibria that can occur. For example, the SCRs can dimerize, and that SCR001 can form 1:1, 2:1, and 1:2 complexes with certain β-Man in $CDCl_3$ and $CD_2Cl_2$, and all these equilibria were considered when fitting the binding data. The $K_a$s and $\Delta G°$ for all SCR.glycan complexes and $K_d$ for all SCRs were determined by minimizing the sum of squared residuals between the experimental data and the modelled fit (FIG. 16). Although binding studies by ESI mass spectrometry showed that all SCRs bind all glycans assayed, $K_a$s less than a threshold of $3.0 \times 10^1$ $M^{-1}$ are reported as "no detectable binding", and NMR peak shifts less than the threshold of $\Delta\delta=0.02$ ppm are also considered as "no binding" in an effort to avoid overestimation of $K_a$s, and no $K_a$ is reported unless 2 peaks in the $^1$H NMR spectra have M>0.02 ppm. To maximize the accuracy of the fit, NMR peak shift data of only clearly resolved peaks of glycans and SCRs that shifted a $\Delta\delta$>0.02 ppm were fit simultaneously to an appropriate binding model, and the model that had the lowest error with the titration data was selected as the correct equilibrium. For example, the NMR peak shift data for the association of SCR019 with β-Man (FIG. 14B and FIG. 14C) were best fit with a 1:2 SCR.glycan binding model with $K_1$, $K_2$ and $\beta$ of 2.3 $M^{-1}$, 3.2×10$^4$ $M^{-1}$ and 7.4×10$^4$ $M^{-2}$ where $K_1$, $K_2$ and $\beta$ correspond to 1:1 and 1:2 SCR.glycan association constants and cumulative association constant ($K_1 \times K_2$ $M^{-2}$), respectively. The fact that $K_2$ is much higher than the negligible $K_1$ indicates the high stability of the 1:2 SCR.mannoside complex SCR019:$\beta$-Mane over 1:1 complex SCR019:$\beta$-Man as a result of positive cooperativity occurring between SCR019 and $\beta$-Man. Fitting of NMR peak shift data revealed that similar multiple equilibria with 1:1 and 1:2 SCR.glycan complexes occur in the association of SCR017 (3-pyrrole) with $\beta$-Glc ($K_1$=1.2 $M^{-1}$, $K_2$=6.8×10$^3$ $M^{-1}$, $\beta$=8.4×10$^3$ $M^{-2}$), SCR020 (2-pyridine) with $\alpha$-Man ($K_1$=2.6×10$^2$ $M^{-1}$, $K_2$=1.1×10$^3$ $M^{-1}$, $\beta$=2.8×10$^5$ $M^{-2}$) and SCR021 (3-pyridine) with $\beta$-Glc ($K_1$=2.7 $M^{-1}$, $K_2$=1.2×10$^4$ $M^{-1}$, $\beta$=3.3×10$^4$ $M^{-2}$ (see Supporting Information). On the other hand, the association of SCR022 (2-phenol) with $\beta$-Glc showed formation of 1:1 and 2:1 SCR.glycan complexes in $CD_2Cl_2$ ($K_1$=1.2×10$^2$ $M^{-1}$, $K_2$=6.9×10$^2$ $M^{-1}$, $\beta$=8.1×10$^4$ $M^{-2}$ (see Supporting Information). In all these cases, $K_2/K_1$ ratio was >1, indicating the formation of higher stoichiometric complex with positive cooperativity. For the all other SCR.glycan systems, the best fit of the NMR peak shift data was obtained with a 1:1 SCR.glycan model.

Figure 17A:
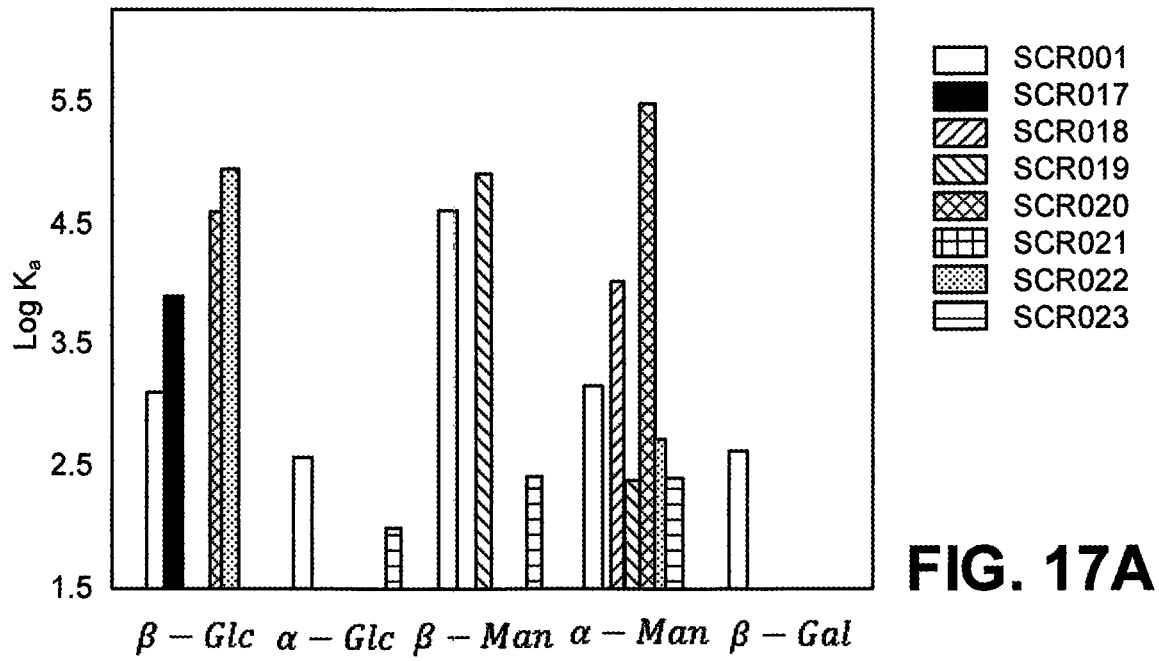
FIG. 17A is a graph depicting Affinities (Log ($K_a$)) values of the receptors towards different glycans.
Figure 17B:
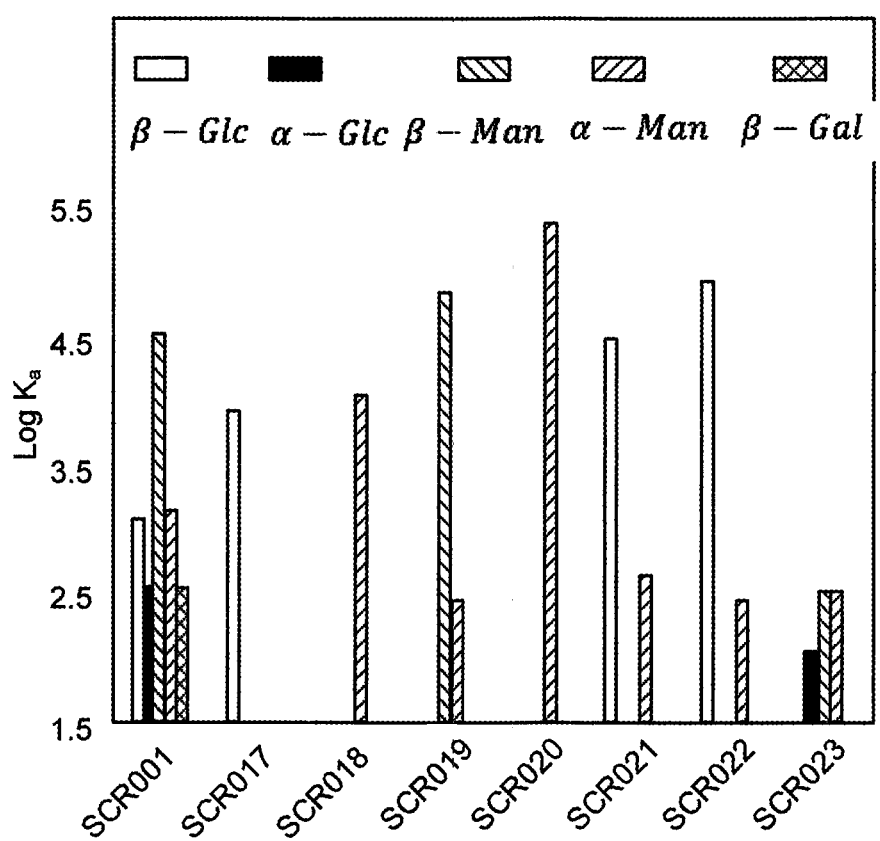
FIG. 17B is a graph depicting Affinities of the glycans towards different SCRs. In both graphs, the baseline is set to log $K_a$ of 1.5 ($K_a$=$3.0 \times 10^1$ $M^{-1}$) as a threshold below which binding cannot be reported accurately.

In contrast to SCR001 (2-pyrrole) that showed promiscuous binding to all glycans assayed, the SCRs SCR017-SCR023 are either selective or specific to certain glycan(s) (FIG. 17A). For example, SCR017 (3-pyrrole), which varies from SCR001 in the position of attachment of the heterocycle to the spacer, is specific for $\beta$-Glc ($\beta$=8.4×10$^3$ $M^{-2}$) with 7-fold high affinity towards $\beta$-Glc. In terms of selectivity of SCRs to glycans (FIG. 17A), SCR017 (3-pyrrole) is specific for $\beta$-Glc. Similarly, the affinity of SCR021 (3-pyridine) $\beta$-Glc is 67 times higher than its affinity for $\alpha$-Man. Likewise SCR022 (2-phenol) is 290 times more selective towards $\beta$-Glc than to $\alpha$-Man. SCR018 (2-indole) and SCR020 (2-pyridine) are specific for $\alpha$-Man, and do not show considerable binding towards any of the other glycans assayed. Lastly, SCR019 (3-indole) has a 250-fold greater affinity for $\beta$-Man than to $\alpha$-Man. On the other hand, the affinity of glycans to different SCRs is also interesting to consider (FIG. 17B). For example, $\beta$-Glc binds SCR001, SCR017, SCR021 and SCR022 with selectivity as high as 62:1 SCR022:SCR001, while $\alpha$-Glc shows binding with only SCR001. $\beta$-Man binds SCR001 with SCR019 a selectivity of 2:1 SCR019:SCR001. However, $\alpha$-Man binds all SCRs except SCR017 with preference for SCR020 with selectivity as high as 200:1 SCR020:SCR001, whereas $\beta$-Gal shows binding to only SCR001.

Interestingly, when comparing SCRs which differ only in the point of attachment of the heterocyclic arm, substantial changes in selectivity and affinity are observed. For instance, a 36 fold selectivity for $\alpha$-Man is achieved from SCR019 (3-indole) ($K_a$ of 2.9×10$^2$ $M^{-1}$) compared to SCR018 (2-indole) ($K_a$ of 1.1×10$^4$ $M^{-1}$). Similarly, for $\alpha$-Man, the pyridine heterocyclic receptors SCR020 (2-pyridine) ($\beta$ of 2.8×10$^5 M^{-2}$) and SCR021 (2-pyridine) ($K_a$ of 4.9×10$^2 M^{-1}$), undergo a change in affinity of 570 times. Likewise, SCR018 (2-indole) is specific for $\alpha$-Man forming a 1:1 SCR.glycan complex with $K_a$ of 1.1×10$^4$ $M^{-1}$. On the other hand, the isomer SCR019 (3-indole) is selective towards $\beta$-Man ($\beta$ of 7.4×10$^4$ $M^{-2}$), with weaker 1:1 binding with $\alpha$-Man ($K_a$=2.9×10$^2$ $M^{-1}$). Similarly, SCR020 (2-pyridine) is also specific for $\alpha$-Man, with the strongest affinity among all SCRs reported in the current study, with $\beta$ of 2.8×10$^5$ $M^{-2}$. However, its isomer SCR021 (3-pyridine) binds $\beta$-Glc preferentially, with $\beta$3.3×10$^4$ $M^{-2}$, although it also makes a weaker 1:1 binding with $\alpha$-Man ($K_a$ of 4.9×10$^2$ $M^{-1}$). Likewise, SCR022 (2-phenol) preferentially binds $\beta$-Glc ($\beta$=8.1×10$^4$ $M^{-2}$). In addition, a 1:1 weaker binding was also seen for SCR022 with $\alpha$-Man with $K_a$ of 2.8×10$^2$ $M^{-1}$. In contrast, SCR023 binds weakly to $\alpha$-Man ($K_a$ of 1.5×10$^2$ $M^{-1}$), $\beta$-Man ($K_a$ of 2.5×10$^2$ $M^{-1}$) and $\alpha$-Glc ($K_a$ of 3.1×10$^2$ $M^{-1}$). Thus, the binding studies reveal the importance and influence of varying the heterocyclic recognition and their position of attachment on the selectivities and specificities of these tetrapodal SCRs towards different glycans.

New SCRs were synthesized by varying the heterocycle with either pyrrole, indole, pyridine or phenol, and by varying their position of attachment. These SCRs were synthesized by the disclosed standard three-step protocol in 34% to quantitative yield. Binding studies with a set of C1-octyloxy pyranosides were performed by ESI mass spectrometry and NMR titrations in $CD_2Cl_2$ at 298 K. Mass spectrometry revealed that all SCRs bind all glycans assayed. NMR titrations showed complexation-induced shifts for both glycan and SCR peaks, and the NMR shift data were fit to an appropriate binding model to determine the $K_a$s. In some cases, multiple cooperative binding pathways were observed with $K_2/K_1$>1 because of positive cooperativity. The SCRs of the present study show either specificity or selectivity to different glycans. The 3-pyrrole-based SCR017 is specific for $\beta$-Glc with 7-fold higher affinity over the 2-pyrrole-based SCR001. The 2-indole-based SCR018 is specific for $\alpha$-Man with 10-fold stronger affinity than SCR001, whereas the 3-indole-based SCR019 showed 2-fold high preference for $\beta$-Man compared to SCR001. Similar to SCR018, the 2-pyridine-based SCR020 is also specific for $\alpha$-Man but with 200-fold higher affinity for $\alpha$-Man than SCR001. However, the 3-pyridine-based SCR021 bound $\beta$-Glc selectively with 25-fold higher affinity compared to SCR001. Similarly, the 2-phenol-based SCR022 preferentially bound $\beta$-Glc with 62-fold higher affinity compared to that of SCR001. Thus, the selectivity chart reveals the impact of varying the heterocycles and their position of attachment on binding affinity and selectivity.

Altogether, SCRs have shown interesting applications. A notable example is the prevention of ZIKV infectious activity in vitro. These applications will be further explored with the SCRs reported in this study.

Experimental—New Scrs

General Procedure. SCRs were synthesized following the procedure described below unless otherwise noted. $PPh_3$ (5 mmol, 5 eq) was added to a stirring solution of 1 (1 mmol, 1 eq) in THF (5 mL) at room temperature. The reaction was refluxed under Ar atmosphere for 1 h before the addition of the heteroarylaldehyde (5 mmol, 5 eq) at room temperature. The reaction mixture was refluxed for additional 48 h, cooled to room temperature, and concentrated under reduced pressure. The residue was dissolved in MeOH (5 mL), and $NaBH_4$ (10 mmol, 10 eq), was added in portions at room temperature under Ar atmosphere followed by stirring for 16 h. The reaction mixture was concentrated under reduced pressure, treated with $CHCl_3$ (30 mL) and $H_2O$ (30 mL), and the organic layer was separated. The aqueous layer was extracted with $CHCl_3$ (3×30 mL), and the combined organic layers were dried over anhydrous $Na_2SO_4$, filtered and concentrated under reduced pressure to give the crude product, which was purified by column chromatography ($SiO_2$, $CHCl_3$:MeOH:$NH_3$ (aq)) to give the pure product.

Synthesis of 1,1',1'',1'''-([1,1'-biphenyl]-3,3',5,5'-tetrayl)tetrakis(N-((1H-pyrrol-3-yl)methyl)methanamine) (SCR017). Following the General Procedure, SCR017 was synthesized from 1 and 1H-pyrrole-3-carbaldehyde and purified by column chromatography (SiO$_2$, 9:1:0.5 CHCl$_3$:MeOH:NH$_3$ (aq)) to provide a pale yellow solid (393 mg, 67%). $^1$H NMR (300 MHz, CD$_2$Cl$_2$) δ 7.48 (s, 4H), 7.31 (s, 2H), 6.76 (d, J=2.3 Hz, 8H), 6.21 (t, J=2.15, 4H), 3.88 (s, 8H), 3.74 (s, 8H); $^{13}$C NMR (75 MHz, CD$_2$Cl$_2$) δ=140.93, 127.23, 125.58, 122.09, 117.68, 116.03, 108.25, 108.21, 52.93, 45.65; HRMS (ESI): m/z calcd for C$_{36}$H$_{42}$N$_8$ [M+H]$^+$: 587.3605, found 587.3606.

Synthesis of 1,1',1'',1'''-([1,1'-biphenyl]-3,3',5,5'-tetrayl)tetrakis(N-((1H-indol-2-yl)methyl)methanamine) (SCR18). Following the General Procedure, SCR018 was synthesized from 1 and 1H-indole-2-2-carbaldehyde and purified by column chromatography (SiO$_2$, 9:1:0.5 CHCl$_3$:MeOH:NH$_3$ (aq)) to provide a pale yellow solid (661 mg. 84%). $^1$H NMR (300 MHz, DMSO) δ 10.83 (s, 4H), 7.61 (d, J=7.7 Hz, 4H), 7.52 (d, J=8.0 Hz, 4H), 7.37-7.27 (m, 6H), 7.24 (s, 4H), 7.04 (t, J=7.0, 4H), 6.92 (t, J=6.9, 4H), 3.88 (s, 8H), 3.81 (s, 4H); $^{13}$C NMR (75 MHz, CD$_2$Cl$_2$) δ 141.47, 141.03, 137.95, 136.57, 128.85, 127.63, 126.14, 121.74, 120.38, 119.88, 111.16, 100.76, 77.96, 46.61; HRMS (ESI): m/z calcd for C$_{52}$H$_{50}$N$_8$[M+H]$^+$: 787.4231, found 787.4230.

Synthesis of 1,1',1'',1'''-([1,1'-biphenyl]-3,3',5,5'-tetrayl)tetrakis(N-((1H-indol-3-yl)methyl)methanamine) (SCR019). Following the General Procedure, SCR019 was synthesized from 1 and 1H-indole-3-carbaldehyde and purified by column chromatography (SiO$_2$, 9:1:0.5 CHCl$_3$:MeOH:NH$_3$ (aq)) to provide a pale yellow solid (763 mg, 97%). $^1$H NMR (300 MHz, DMSO) δ 10.83 (s, 4H), 7.61 (d, J=7.7 Hz, 4H), 7.52 (d, J=8.0 Hz, 4H), 7.37-7.27 (m, 6H), 7.24 (s, 4H), 7.04 (t, J=7.0, 4H), 6.92 (t, J=6.9, 4H), 3.88 (s, 8H), 3.81 (s, 4H); $^{13}$C NMR (75 MHz, CD$_2$Cl$_2$) δ 141.52, 141.01, 136.79, 127.84, 127.41, 126.24, 123.68, 122.08, 119.49, 118.83, 113.84, 111.68, 78.05, 43.98; HRMS (ESI): m/z calcd for C$_{52}$H$_{50}$N$_8$ [M+H]$^+$: 787.4231, found 787.4227.

Synthesis of 1,1',1'',1'''-([1,1'-biphenyl]-3,3',5,5'-tetrayl)tetrakis(N-(pyridin-2-ylmethyl)methanamine) (SCR020). Following the General Procedure, SCR020 was synthesized from 1 and picolinaldehyde and purified by column chromatography (SiO$_2$, 9:1:0.5 CHCl$_3$:MeOH:NH$_3$ (aq)) to provide a pale yellow gum (628 mg, quant.). $^1$H NMR (300 MHz, CDCl$_3$) δ 8.50 (s, 4H), 7.56 (t, J=7.6 Hz, 4H), 7.47 (s, 4H), 7.33-7.23 (m, 6H), 7.08 (t, J=7.1 Hz, 4H), 3.91 (s, 8H), 3.85 (s, 4H), 2.53 (br s, 4H); $^{13}$C NMR (75 MHz, CDCl$_3$) δ 159.67, 149.24, 141.33, 140.71, 136.41, 127.14, 125.89, 122.37, 121.91, 54.56, 53.52; HRMS (ESI): m/z calcd for C$_{40}$H$_{42}$N$_8$ [M+H]$^+$: 635.3605, found 635.3607.

Synthesis of 1,1',1'',1'''-([1,1'-biphenyl]-3,3',5,5'-tetrayl)tetrakis(N-(pyridin-3-ylmethyl)methanamine) (SCR021). Following the General Procedure, SCR021 was synthesized from 1 and nicotinaldehyde and purified by column chromatography (SiO$_2$, 9:1:0.5 CHCl$_3$:MeOH:NH$_3$ (aq)) to provide a pale yellow gum (628 mg, quant.). $^1$H NMR (300 MHz, CDCl$_3$) δ 8.61 (s, 4H), 8.52 (d, J=3.2 Hz, 4H), 7.73 (d, J=7.8 Hz, 4H), 7.48 (s, 4H), 7.36-7.22 (m, 6H), 4.07-3.61 (m, 16H), 1.88 (br s, 4H); $^{13}$C NMR (75 MHz, CDCl$_3$) δ 149.80, 148.57, 141.46, 140.74, 135.86, 135.53, 127.00, 125.88, 123.42, 53.24, 50.66; HRMS (ESI): m/z calcd for C$_{40}$H$_{42}$N$_8$ [M+H]$^+$: 635.3605, found 635.3603.

Synthesis of 2,2',2'',2'''-((([1,1'-biphenyl]-3,3',5,5'-tetrayl)tetrakis(methylene))tetrakis(azanediyl))tetrakis(methylene))tetraphenol (SCR022). Following the General Procedure, SCR022 was synthesized from 1 and 2-hydroxybenzaldehyde and purified by column chromatography (SiO$_2$, 9:1:0.5 CHCl$_3$:MeOH:NH$_3$ (aq)) to provide a yellow solid (660 mg, 95%). $^1$H NMR (300 MHz, CDCl$_3$) δ 7.46 (s, 4H), 7.26-7.16 (m, 6H), 7.04 (d, J=7.5 Hz, 4H), 6.92-6.76 (m, 8H), 4.08 (s, 8H), 3.91 (s, 8H); $^{13}$C NMR (75 MHz, CDCl$_3$) δ 158.07, 141.53, 139.56, 128.93, 128.65, 127.66, 126.55, 122.17, 119.25, 116.43, 52.51, 52.00; HRMS (ESI): m/z calcd for C$_{44}$H$_{46}$N$_4$O$_4$ [M+H]$^+$: 695.3592, found 695.3586.

Synthesis of 3,3',3'',3'''-((([1,1'-biphenyl]-3,3',5,5'-tetrayltetrakis(methylene))tetrakis(azanediyl))tetrakis(methylene))tetraphenol (SCR023). Following the General Procedure, SCR023 was synthesized from 1 and 3-hydroxybenzaldehyde and purified by column chromatography (SiO$_2$, 8:2:2 CHCl$_3$:MeOH:NH$_3$ (aq)) to provide a white solid. $^1$H NMR (800 MHz, CD$_2$Cl$_2$) δ 7.52 (s, 4H), 7.27 (s, 2H), 7.18 (t, J=7.6 Hz, 4H), 6.85 (s, 4H), 6.81 (d, J=7.1 Hz, 4H), 6.74 (d, J=7.4 Hz, 4H), 3.83 (s, 8H), 3.77 (s, 8H); $^{13}$C NMR (75 MHz, CDCl$_3$) δ=157.16, 141.01, 140.74, 140.14, 129.56, 127.77, 126.01, 119.65, 115.06, 114.34, 52.60, 52.49; HRMS (ESI): m/z calcd for C$_{44}$H$_{46}$N$_4$O$_4$ [M+H]$^+$: 695.3592, found 695.3586.

ESI Mass Spectrometry Analysis of Receptor-Glycan Binding Methods. A Bruker ultra-high resolution maXis-II/ETD ESI-q-TOF system was used to study receptor-glycan complex formation. The samples of the SCRs and the glycans were prepared in 1 mM in CH$_2$Cl$_2$, diluted to 1 μM with 40% CH$_2$Cl$_2$ in MeCN. The samples of SCR+glycan for complex mass screening were prepared using the aforementioned diluted solutions and mixed in a one-to-one fashion. All samples were analyzed via direct infusion into the spectrometer with a syringe pump. Theoretical isotopic distributions were calculated using the Chemistry tool in Bruker's Compass DataAnalysis software.

NMR Titrations and Peak Shift Fittings $^1$H NMR titrations were performed in CD$_2$Cl$_2$, unless otherwise noted, at a field strength of either 600, 700 or 800 MHz at 298 K. The experimental temperatures were verified through calibration with a 100% methanol standard. The addition of pyranoside to a SCR CD$_2$Cl$_2$ solution or vice versa resulted in the perturbation of the chemical shifts (δ) corresponding to resonances of both SCR and pyranoside. This is the result of an exchange process involving SCR (H) and pyranoside (G) equilibria products interchanging fast on the NMR timescale, resulting in the averaging of chemical shis of protons in differing chemical environments. Accordingly, equilibrium constants (K) can be quantified by first defining a model that includes the correct set of equilibria, calculating the hypothetical concentrations of equilibrium species and the corresponding chemical shifts, and finally fitting the resulting data to the experimental results. For the 2:1 association between SCR022 and β-Man, fitting was carried out. Similarly, for the 1:2 association between SCR017 and β-Glc, SCR021 and β-Glc, SCR019 and β-Man, SCR020 and α-Man.

Additional Binding Study

The following section focuses on eight SCRs with five distinct octyloxy pyranosides, which were measured by mass spectrometry and by $^1$H NMR titrations in CD$_2$Cl$_2$ at 298 K, providing binding affinities that vary from ~10$^1$-10$^4$ M$^{-1}$. Although receptors are promiscuous, SCR001 shows selectivity for β-Man at a ratio of 103:1 β-Man:β-Gal, receptors SCR002, SCR003, SCR016 and SCR005 have preference for α-Man, SCR004 is selective for β-Gal, and SCR012 prefers α-Glc. A variety of 1D and 2D NMR, and computational techniques were used to determine the thermodynamic binding parameters (ΔH° and ΔS°) and the structure of the host-guest complex, revealing that dimeric receptor SCR012 binds β-Man with increased enthalpy, but a larger entropic penalty than SCR001. The first-principles modelling suggests that SCR012.β-Man forms an inclusion-type complex where the glycan engages both monomeric subunits of SCR012 through H-bonding and C—H . . . π interactions. Like natural glycan binding proteins, these receptors bind pyranosides by accessing multivalent and cooperative interactions, and these studies suggest a new approach towards biomimetic synthetic carbohydrate receptors, where conformational flexibility and promiscuity are incorporated into design.

The surface of every eukaryotic cell is coated with a layer of glycolipids, glycoproteins, and glycopolymers—termed the glycocalyx—and binding events involving these oligosaccharides mediate a wide variety of biological events, including cell-cell communication, immunological response, cell-pathogen interactions, and disease progression. Cell-surface glycosylation patterns are unique and accessible identifiers of cell-type. For example, α-mannose is overexpressed on the surface of human lung, and prostate cancer cells, whereas β-galactose is abundant on human testicular, brain, and white blood cancer cells. So synthetic molecules that recognize with some preference specific mono- and oligosaccharides in the glycocalyx could be used for disease detection, drug delivery, therapeutics or even for understanding how information is transmitted in biological networks. Although mannose and galactose are abundant on cell-surface glycans, their epimer, glucose, is almost entirely absent from cell surfaces because it occurs in such high concentration in the blood and cytoplasm, and, as such, for sugar-binding molecules to migrate from the circulatory system, they must bind non-glucosides. Despite the medicinal and biological significance of targeting the glycocalyx, cell surface glycans are generally considered as "undruggable targets" because highly specific glycan receptors are confined to natural lectins and antibodies, which have potential toxicology and immunological limitations. In this context, small molecule receptors are of interest but their design is extremely challenging as selectivity is needed for complex molecules that differ sometimes by only the orientation of a single stereocenter.

Despite these difficulties, a significant number of synthetic carbohydrate receptors—including some that bind in water—have been developed. These fall primarily into two classes: those that bind through the formation of boronate esters and rigid scaffolds that bind entirely through noncovalent contacts. The latter include rationally-designed, small molecules as well as peptide- and aptamer-based hosts, and some discovered through dynamic libraries. The boronates bind monosaccharides possessing syn-diols with binding affinities ($K_a$s) in water ranging between $10^3$-$10^4$ M$^{-1}$, and particularly noteworthy examples are the chiral diboronic acid receptors that bind D-Fructose and D-Glucose with $K_a$s of ~$10^4$ M$^{-1}$ and others for pattern-based saccharide sensing. The noncovalent, small molecule receptors, in contrast, organize polar and nonpolar domains around a rigid scaffold, and examples include calixarenes and oligoaromatic receptors, cyclodextrins, porphyrin conjugates, pod and receptors, encapsulating receptors, peptide-based receptors and the temple receptors developed by Davis that bind primarily all-equatorial glycans in organic solvents with $K^a$~$3.0\times10^5$ M$^{-1}$ and in aqueous solvents with $K_a$s as high as $1.2\times10^4$ M$^{-1}$. The applications for these glucoside-binding receptors are manifold, including the monitoring of blood glucose, the early detection of disease biomarkers such as sialyl Lewis X antigen and TF antigen, and the site-specific imaging of cancer cells, which is still dominated by glucose and sialic acid binders. However, for applications including cell-surface targeting, carbohydrate-based nanotechnology, or characterizing the structure of complex oligosaccharides, there remains a need to continue developing synthetic carbohydrate receptors that associate to non-glucosides or other all-equatorial glycans.

Generally, the synthetic receptors that bind through noncovalent interactions are designed by following a principle of preorganization wherein binding affinity increases in rigid receptors because the entropic penalty of reorganization is minimized. This design strategy is consistent with Fisher's "lock-and-key" model of protein binding, which assumes that both enzyme and substrate have rigid conformations that lead to an ideal fit with relatively high $K_a$s. Glycan binding proteins—like lectins or the periplasmic binding proteins—are examples of the more nuanced "induced-fit" model, where enzyme flexibility and substrate influence dictate the structure of the enzyme-substrate complex. Typically, glycan binding proteins are characterized by promiscuity—they will often bind several monosaccharides with weak 1:1 binding but achieve affinity enhancement of up to $10^6$ M$^{-1}$ and increased selectivity by accessing cooperative and multivalent binding pathways, a phenomena termed the "cluster-glycoside effect". Most synthetic carbohydrate receptor designs do not consider these aspects of natural systems. Thus, developing synthetic carbohydrate receptors that associate with non-glucosidic monosaccharides may require approaches towards receptor design that reconsider the role of preorganization and the meanings of selectivity and specificity in the unique context of carbohydrate recognition.

The previous section of this disclosure provides a highly flexible synthetic tetrapodal carbohydrate receptor SCR001 that possesses four aminopyrroles organized around biaryl core that binds α-mannosides preferentially in chloroform through H-bonding and C—H . . . π interactions in concert with multivalent and cooperative equilibria. This receptor is one of only very few synthetic receptors so far reported that are selective for mannose. Like natural glycan binding proteins, this receptor is promiscuous and forms 1:1 complexes in CHCl$_3$ with all monosaccharides assayed, and selectivity as high as 16.8:1 α-Man: α-Gal and 1.5:1 α-Man: β-Glc is achieved as a result of 2:1 and 1:2 receptor:substrate complexes. This receptor demonstrates the potential of flexible scaffolds for addressing the unmet challenge of creating synthetic carbohydrate receptors that possess non-glucosidic selectivities. Studies using an anthracene-based receptor, have subsequently confirmed the value of incorporating conformational flexibility in receptor design as a route to increasing binding affinity. Building upon this result, they subsequently reported a pyrene-based synthetic carbohydrate receptor that binds some axially substituted pyranosides in water, whose negatively charged variant forms 1:2 host:guest complexes with aminosugars, with $K_1$ of ~$3.0\times10^3$ M$^{-1}$ for D-mannosamine. In turn, a positively charged variant binds α-sialyl units with $K^1$ of ~$1.3\times10^3$ M$^{-1}$. These studies show the promise of flexible molecules as selective carbohydrate receptors, and that there remains a need to continue exploring how changes in synthetic carbohydrate receptor structure can access the binding modes common in nature—particularly cooperativity and multivalency. This disclosure does so by exploring how receptor structure affects $K_a$ and selectivity in a library of flexible synthetic carbohydrate receptors based upon the structure of SCR001, and these data guides the rational design of additional carbohydrate receptors.

This disclosure describes how variations in the structures of flexible carbohydrate receptors affect their $K_a$s and selectivities towards a series of carbohydrate guests. To this end, a library of receptors was prepared based upon the biaryl core of tetrapodal synthetic receptor SCR001, and these synthetic carbohydrate receptors differ from SCR001 in the nature of the heterocycle, the bond between the heterocycle and the biaryl core, and whether the receptor is dimeric.

Subsequently, their binding to a small library of glycans functionalized with solubilizing octyloxy groups at the anomeric (C1) carbon was studied in $CH_2Cl_2$ by mass spectrometry and in $CD_2Cl_2$ by NMR spectroscopy, where the latter was used to quantify $K_a$s. Finally, variable temperature (VT) NMR titrations, Nuclear Overhauser Effect (NOE) 2D NMR spectroscopy, and molecular modeling were used to interrogate the thermodynamic and structural details of the association between SCR012 and β-Man. The data from the host:guest system composed of SCR012 and β-Man is used as an illustrative example to describe how each of the different analyses were performed, and the data from the other thirty-nine host:guest pairs are provided in the Supporting Information, with results summarized below. Because SCR007 and SCR008 were not soluble in $CH_2Cl_2$, their binding with the monosaccharides was not studied.

Synthesis of the receptors. Inspired by the initial results with SCR001, the receptor structures were varied, while maintaining the overall flexibility of the scaffold by building upon the freely rotating biphenyl core. It was reasoned that receptors with different H-bond donors and acceptors may differ in their specificities to the carbohydrate guests as a result of differences in noncovalent bonding with the sugars. The structural variations explored here consist of changing the heterocycles to include furan, thiophene, and N-methyl imidazole groups with amine, imine and amide linkages of the heterocycle to the and increasing provide the respective imine intermediate, which when treated with $NaBH_4$ provided tetrapodal receptor SCR001 in 80% yield. In the same manner, receptors SCR002, SCR003 and SCR016 were synthesized from intermediate 1 by using the respective heterocyclic aldehyde in yields ranging from 40-95%. From 1, the imine-based receptors SCR004, SCR005 and SCR006 (FIG. 2) were synthesized but isolated in poor yields (17-32%), presumably because of hydrolysis during purification by column chromatography on silica gel. The amide-based receptors SCR007 and SCR008 were synthesized via HBTU-mediated coupling of the corresponding heterocyclic carboxylic acid with the tetraamine 2 (FIG. 5B), which was obtained from 1 through a Staudinger amination in quantitative yield. For the synthesis of dimeric receptor SCR012, two units of SCR001 were linked with the alkyne-terminated triethylene glycol chain via a CuI-catalyzed azide-alkyne Huisgen reaction (azide:alkyne 5:1) in the presence of $CuSO_4$, sodium ascorbate and bathocuproinedisulfonic acid disodium salt (Batho) to provide receptor valency by linking two biaryl cores with an oligoethylene glycol chain, the latter inspired from the finding that SCR001 binds β-Glc and α-Man in a 2:1 host:guest stoichiometry (S. Rieth, M. R. Miner, C. M. Chang, B. Hurlocker, A. B. Braunschweig, Chem. Sci. 2013, 4, 357-367.). All receptors were synthesized from the common tetraazide intermediate 1. The amine-based receptors SCR001, SCR002, SCR003 and SCR016 were prepared from intermediate 1 in a one-pot procedure involving three reactions occurring on each of the four azide sites. To form SCR001, a Staudinger amination of tetraazide 1 to the corresponding iminophosphorane was followed by an aza-Wittig reaction with four-fold excess of 1H-pyrrole-2-carbaldehyde to the hexaazide 13 in 39% yield. Hexaazide 13 was converted into dimeric receptor SCR012 by following the three-step amine-forming protocol, where eighteen bond-forming steps proceed in one-pot and in 50% overall yield. Importantly, by using different diynes and heterocyclic precursors, this synthetic strategy can be easily diversified to create expanded libraries of carbohydrate receptors beyond those described herein.

Figure 18:
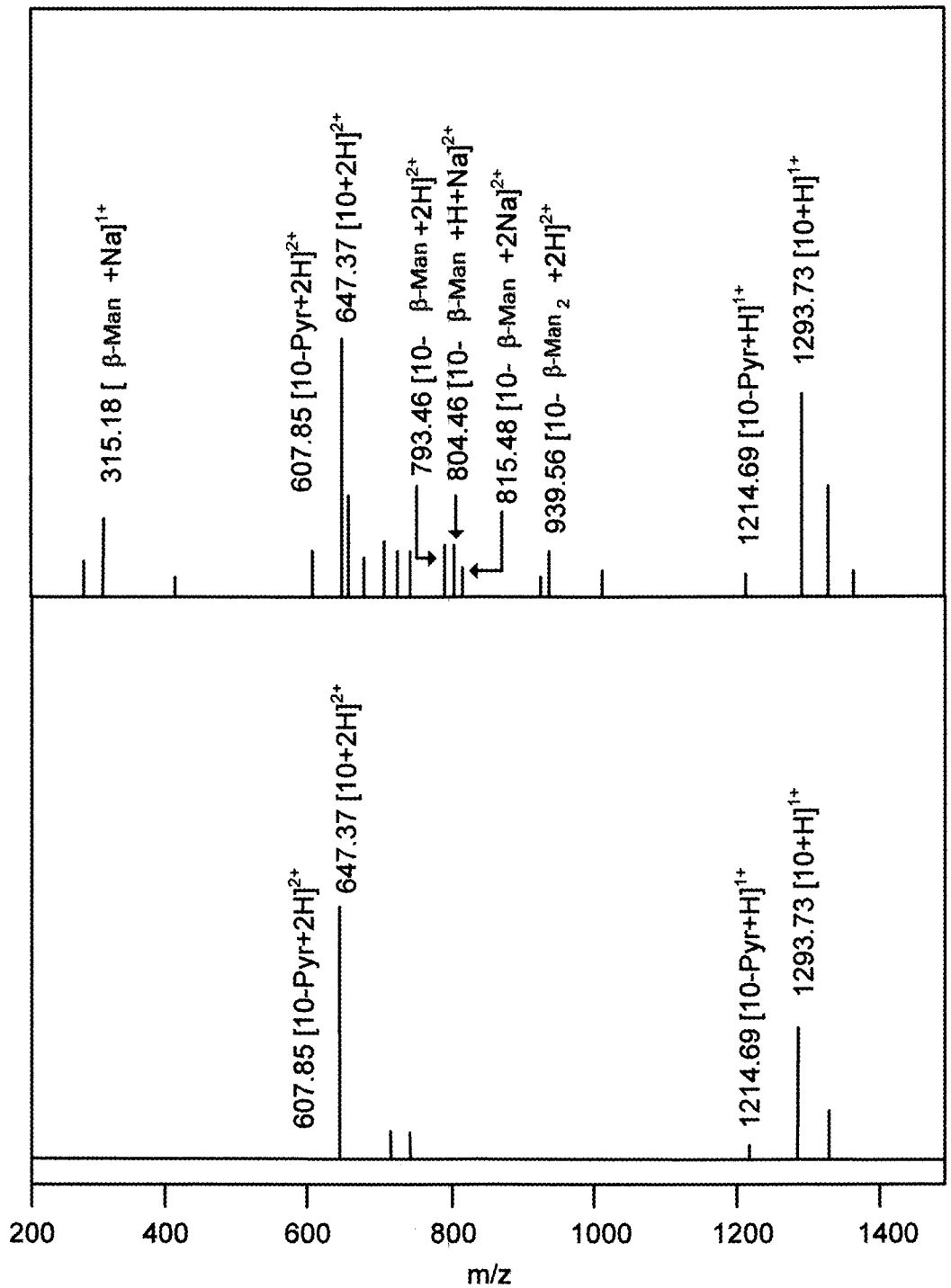
FIG. 18 depict two ESI mass spectra. Top: ESI mass spectrum of a 1:1 mixture (0.5 μM, 40%:60% v/v $CH_2Cl_2$:$CH_3CN$) of SCR012 and β-Man. Bottom: ESI mass spectrum of SCR012 alone (1.0 μM, 40%:60% v/v $CH_2Cl_2$:$CH_3CN$). Peaks were assigned using Compass Data Analysis Software (Bruker)

Mass spectrometry binding studies. Binding between glycans and the synthetic receptors was first investigated by electrospray ionization (ESI) mass spectrometry. Initially, solutions containing the receptors alone were subjected to mass spectrometry because understanding the fragmentation patterns of the receptors is necessary to interpret the mass spectra of the host-guest complexes. To this end, 1 mM solutions of receptors were prepared in $CH_2Cl_2$, diluted to 1 μM with 40% $CH_2Cl_2$ in $CH_3CN$, and then injected via direct infusion into the spectrometer with a syringe pump. The receptors had a distinct fragmentation pattern, where ions corresponding to the cleavage of each heterocyclic arm were prevalent because of the stability of the benzylic anions that are generated upon breaking of the NC bond. For example, the positive mode ESI-MS spectrum of SCR012 possesses $[M+H]1^+$ peaks corresponding to the molecular ion as well as $1^+$ ions corresponding to the loss of one 2-methyl pyrrole group in addition to $2^+$ peaks corresponding to the molecular ion and loss of one 2-methyl pyrrole group (FIG. 18). In addition, ionization conditions could be found so that peaks corresponding to the loss of all six pyrrole groups were observed. In the case of other receptors SCR001, SCR002, SCR003, SCR004, SCR005, SCR006 and SCR016, the positive ESI-MS spectrum possess $[M+H]^{1+}$ and $1^+$ ions or $2^+$ ions corresponding to the loss of one or more heterocyclic groups.

To study the binding of the glycans with the receptors, 1 mM solution of octyloxy glycans were prepared in $CH_2Cl_2$ and diluted to 1 μM with 40% $CH_2Cl_2$ in $CH_3CN$. These diluted glycan solutions were mixed in one-to-one fashion with 1 μM of receptor solution prepared as mentioned above, to create a mixture that was introduced into the spectrometer via direct infusion with a syringe pump. These same solutions were prepared for all forty receptor:glycan combinations. Compass Data Analysis software (Bruker) was used to simulate the expected masses and isotopic distributions of the complexes and individual components to assign the ions observed in the spectra. For the SCR012.β-Man mixture, various ions corresponding to the host-guest complex were observed (FIG. 18). The most prominent receptor-glycan ions corresponded to the $[SCR012.β\text{-}Man+2H]^{2+}$ complex, and the isotopic distributions of the peaks further confirm the formation of the SCR012.β-Man complex. In addition, ions corresponding to $[SCR012.β\text{-}Man+H+Na]^{2+}$, $[SCR012.β\text{-}Man+2Na]^{2+}$ and $[SCR012.β\text{-}Man2+2H]^{2+}$ were also seen in addition to $[SCR012+2H]^{2+}$ and $[SCR012\text{-}Pyr+2H]^{2+}$. Various other ions were common in the ESI spectra of SCR012.glycan when other carbohydrates were added to the solutions of SCR012, with the relative intensities of the ions dependent on the particular host:guest combination. While these same $[SCR012.glycan+21\text{-}1]^{2+}$ ions were observed in the case of SCR012.α-Man and SCR012.β-Glc complexes, $[SCR012.glycan+3H]^{3+}$ ions were found to be prominent in the ESI-MS spectrum of SCR012.α-Glc and SCR012.β-Gal solutions. These ESI experiments were repeated for all receptors that had solubility in $CH_2Cl_2$ with all five glycans. The positive mode ESI-MS spectra revealed the presence of a 1:1 receptor-glycan complex in all forty receptor:glycan mixtures. These mass spectrometry experiments confirm the stability of the host:guest complexes in the gas phase, and demonstrate that—like natural glycan-binding proteins—the synthetic receptors studied here are promiscuous, and that all receptors bind to all glycans to some degree.

NMR titrations and determination of Kas. To confirm host:guest association and determine quantitatively how the receptor structures affect Kas and selectivities, binding was studied by performing NMR titrations at 298 K in $CD_2Cl_2$. NMR is widely used to study host-guest binding, and in particular for complexes whose $K_a$s range from $1$-$10^5$ $M^{-1}$, which is a typical range for synthetic carbohydrate receptors. Also, synthetic carbohydrate receptor binding is commonly studied in non-aqueous solvents because $K_a$s are generally higher than they would be in aqueous solvents, so changes in $K_a$s as a result of structural variations are amplified and more easily understood. Here $CD_2Cl_2$ was chosen as the solvent because it does not compete for H-bonds between the glycans and the receptors. SCR001 undergoes dimerization with a $K_d$=13.0 $M^{-1}$ in $CDCl_3$ at 298 K. So prior to performing the receptor:glycan titrations, dilutions were performed at a concentration range of 12.5 mM-65.6 µM with receptors SCR001, SCR002, SCR003, SCR004, SCR005, SCR006, SCR016 and SCR012, and, when peak shifts occurred, they were fit to a dimerization model to determine $K_d$. Dimerization was only observed in receptor SCR001 and SCR004 in the receptor concentration range at which the host-guest association was studied (0.2-8.8 mM).

Figure 19A:
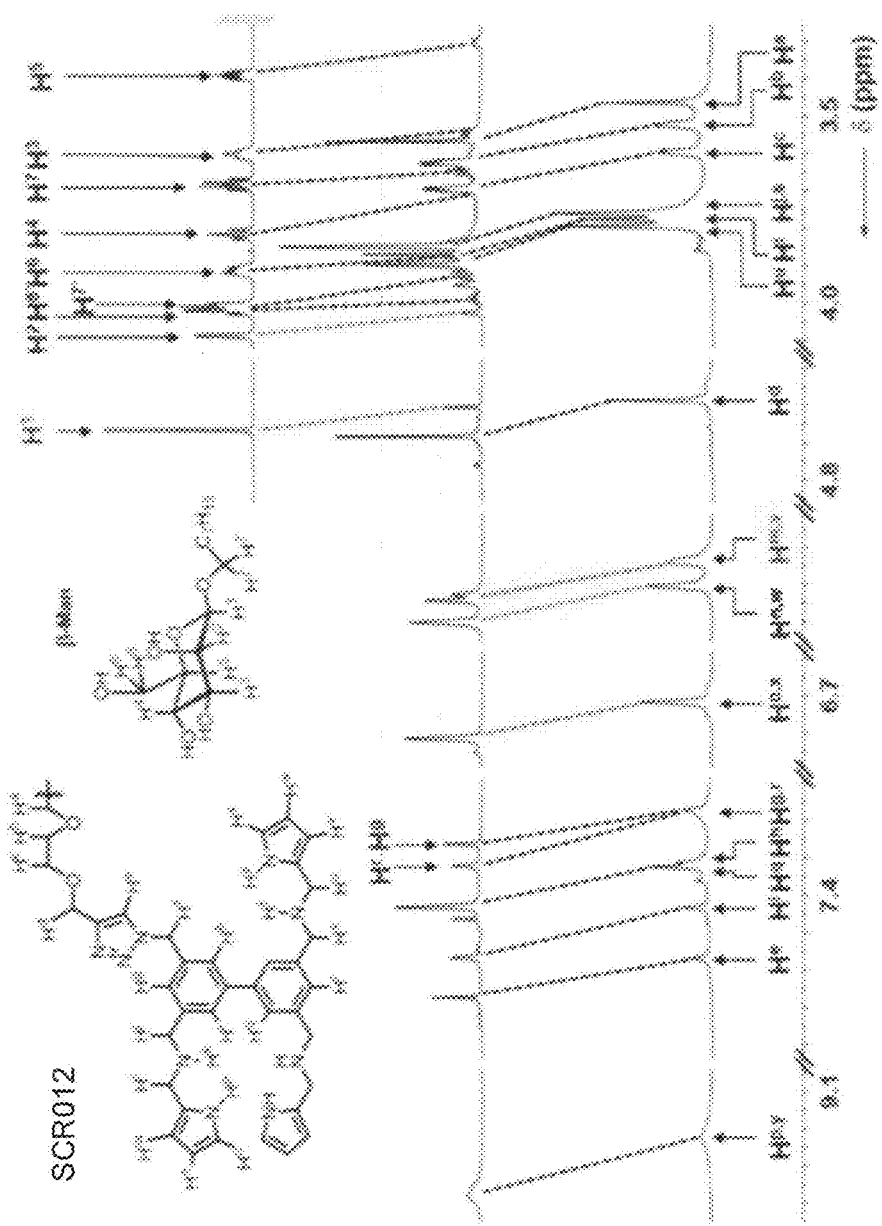
FIG. 19A is a $^1H$ NMR (700 MHz, $CD_2Cl_2$, 298 K) of β-Man (1 mM, top), a 2:1 ratio of SCR012 and β-Man (middle) and SCR012 (0.5 mM, bottom). Dashed lines track the shifts of peaks upon mixing of SCR012 and β-Man.

To quantify $K_a$s, $^1$H NMR titrations were subsequently performed by adding aliquots of receptor solutions (12.5 mM) to 1 mM glycan solutions in $CD_2Cl_2$. The receptor:glycan concentrations were varied from 1:5 to 30:1, with the glycan concentration kept at ~1 mM. All spectra obtained from these titrations are presented in the Supporting Information, and, as an example, the spectra of SCR012, β-Man, and a 2:1 mixture of SCR012,:β-Man are shown in FIG. 19A. The peaks in the $^1$H NMR spectra of SCR012, and the octyloxy glycans were assigned with the assistance of $^1$H—$^1$H DQF COSY and $^1$H—$^1$H NOESY NMR spectra (see Supporting Information). Upon association, distinct shifts occurred in the peaks corresponding to all the identifiable protons of both receptor and glycan, which indicates complexation-induced changes in chemical environments. In combination with mass spectrometry data as well as studies on the upfield by 0.09 and 0.08 ppm, respectively. Upfield chemical shifts of 0.15-1.72 ppm and 0.01-1.76 ppm, respectively, for the CH protons of sugars have been observed upon complexation in organic media. Upfield shifts of 0.2-0.3 ppm have also been reported for the same. The glycan and receptor peak shifts that occur with the receptors are consistent with these reports. These upfield shifts upon complexation suggest that shielding of these protons is likely the result of C—H . . . π interactions. Shifts are also seen for the peaks corresponding to the host protons, with the largest downfield shifts of 0.11 ppm observed for the pyrrole N—H protons, suggesting that H-bonding has a role in the complexation. A change in chemical shift of 0.70-0.96 ppm has been reported for the pyrrole N—H peak of the receptors upon complexation. The relatively low shift for the peaks corresponding to the pyrrole N—H protons in SCR012 upon complexation compared to those of others' more preorganized receptors can be accounted for by considering that the N—H protons in SCR012 are already involved in H-bonding prior to binding of SCR001, these changes in δ were attributed to the supramolecular association between the receptors and the various octyloxy glycans. In the spectra in FIG. 19A, the largest shift of the β-Man proton peaks correspond to the $H^5$ peak, which shifts 0.13 ppm upfield. Similarly, the signals assigned to $H^1$ and $H^2$ of β-Man shifted complexation that is allowed by the flexibility of the structure, so changes in the chemical environment of this proton are less dramatic. This supposition is supported by the molecular modelling of SCR012, which shows internal H-bonding involving the pyrroles. Chemical shift changes of 0.01-0.04 ppm were observed for the aromatic protons of SCR012, while a Δδ of 0.01-0.80 ppm for aromatic and heteroaromatic protons is typical. Complexation of SCR012 and β-Man also caused a downfield shift of about 0.25-0.30 ppm for the peaks corresponding to the secondary amines N—$H^k$ and N—$H^t$ of SCR012, however, these signals were found to overlap with peaks of the octyloxy side chain of β-Man at lower equivalents of SCR012 and were therefore difficult to track and determine their M. These same titrations were repeated on all other receptor-glycan combinations. In the complexes of receptors SCR001, SCR0016, SCR004, SCR005 and SCR012 with all octyloxy glycans, and in titrations of SCR002.β-Glc, SCR002.α-Man, SCR002.β-Man, SCR003.β-Glc and SCR003.α-Man, significant peak-shifting (Δδ>0.02 ppm) was observed, whereas in the other receptor-sugar titrations, the changes in chemical shift were <0.02 ppm. The maximum complexation-induced Δδ was 0.65 ppm for the peak corresponding to H3 proton of SCR004.β-Gal complex.

Determining $K_a$ from NMR peak shift data requires choosing an appropriate model that accounts for all the equilibria present and fitting the peak shifts to these models to extract $K_a$s. For the association between SCR001 and β-Man in $CDCl_3$, multiple equilibria, including 1:1, 1:2, and 2:1 β-Man:SCR001, should occur. With the exception of the binding between SCR001 and β-Man, no evidence of these higher order complexes was found from the peak fitting, which is consistent with the results from ESI-MS spectra. So a 1:1 binding model was considered to fit the titration data with the exception of the SCR001:β-Man system, where a SCR001$_2$:β-Man equilibrium was also considered. In the case of SCR001:β-Man system, the titration data did not fit well when only a 1:1 binding model was considered. Thus, the data were best fit with a 2:1 receptor-sugar binding model, and the requirement of considering a 2:1 binding was further supported by the Van't Hoff plot (vide infra), which did not fit the data well when only 1:1 binding was considered. To quantify $K_a$s, the shifts (Δδ) in the positions of glycan and receptor peaks that could be clearly resolved were plotted, and they were fit to the appropriate binding between SCR012 and β-Man were performed in triplicate, and the error in $K_a$ was 15%. These data show that both binding strength and the receptor selectivity for different glycans—defined here as the ratio of $K_a$s—are dependent sensitively on the receptor structures. Binding results reveal that receptors SCR001. SCR016, SCR004, SCR005 and SCR012 are promiscuous and form 1:1 complexes with all monosaccharides examined, while SCR002 had measurable binding with only β-Glc, β-Man and α-Man, and SCR003 only had measurable binding with β-Glc, and α-Man. Receptor SCR006 did not have quantifiable binding (Δδ<0.02 ppm) with any of the glycans.

Figure 19B:
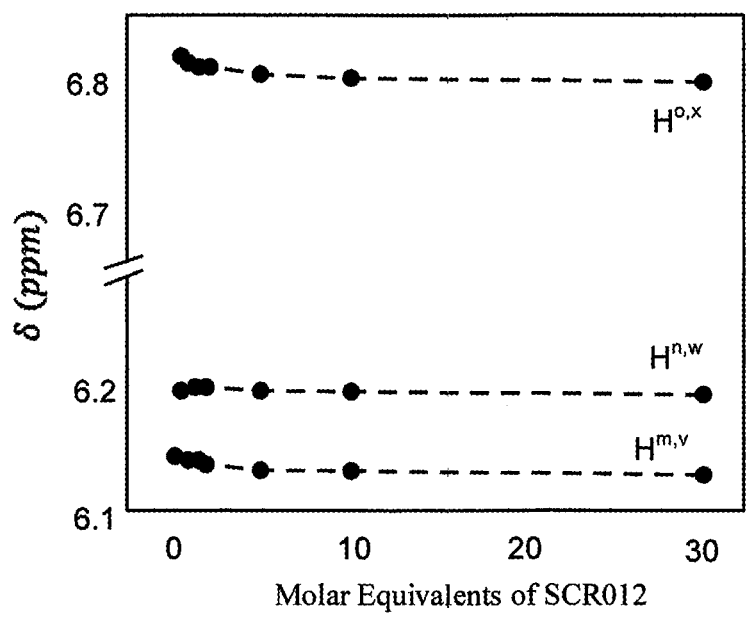
FIG. 19B shows the shifts of the NMR peak of the $H^{m,v}$, $H^{n,w}$, and $H^{o,x}$ protons of SCR012 upon addition to β-Man in $CD_2Cl_2$ at 298 K, with bullets and lines representing the experimental data and the fit from a 1:1 binding model, respectively.
Figure 19C:
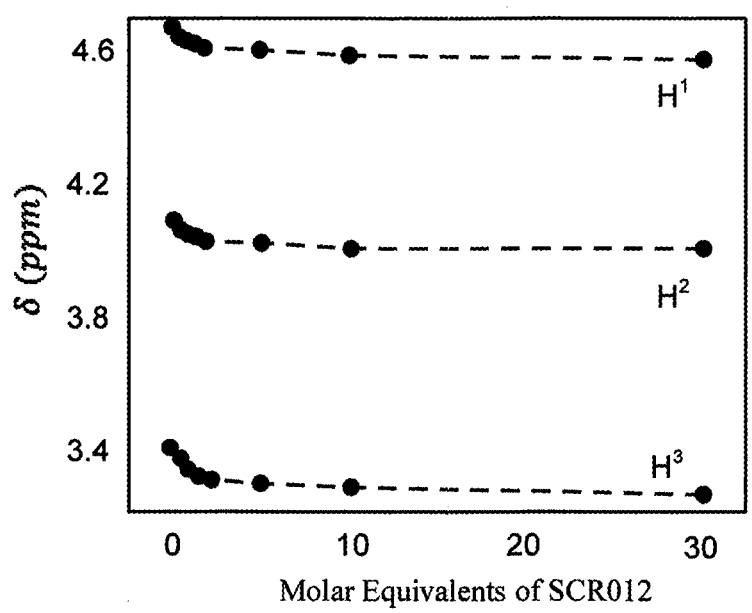
FIG. 19C shows the shift of the NMR peaks for protons $H^5$, $H^2$ and $H^1$ of β-Man at 298 K, with bullets and lines representing the experimental data and the fit from a 1:1 binding model, respectively.
Figure 20A:
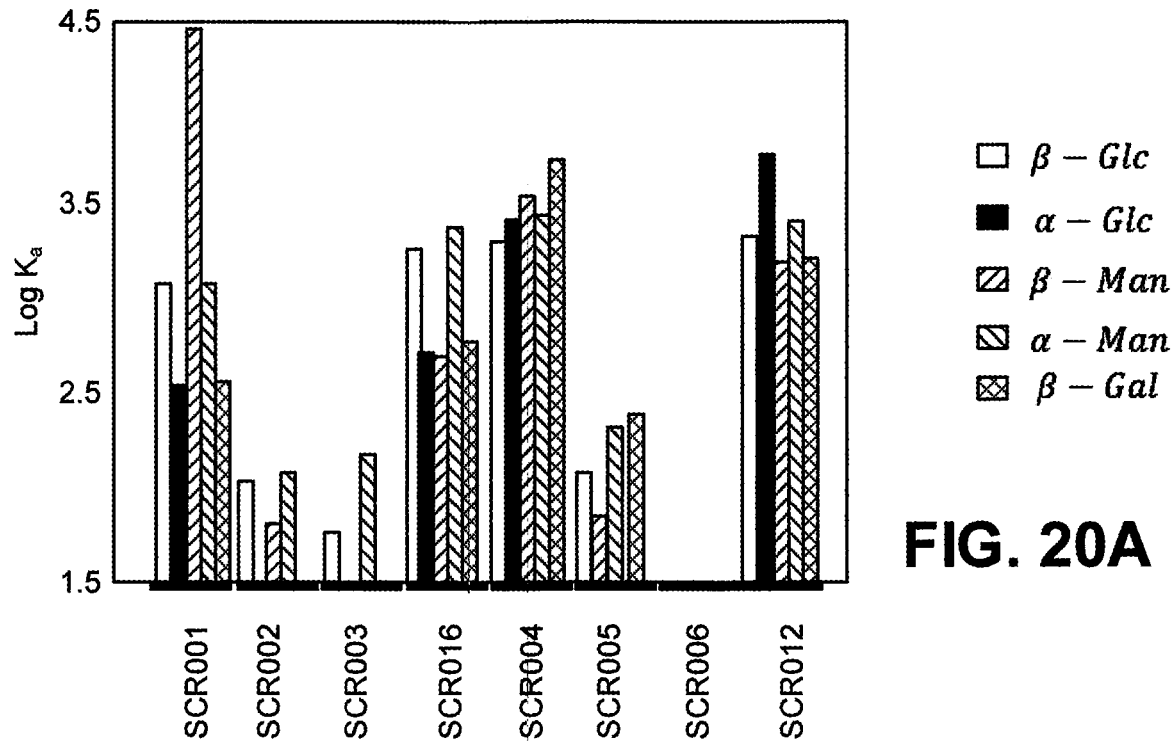
FIG. 20A is a graph depicting relative affinities of the receptors towards different glycans.
Figure 20B:
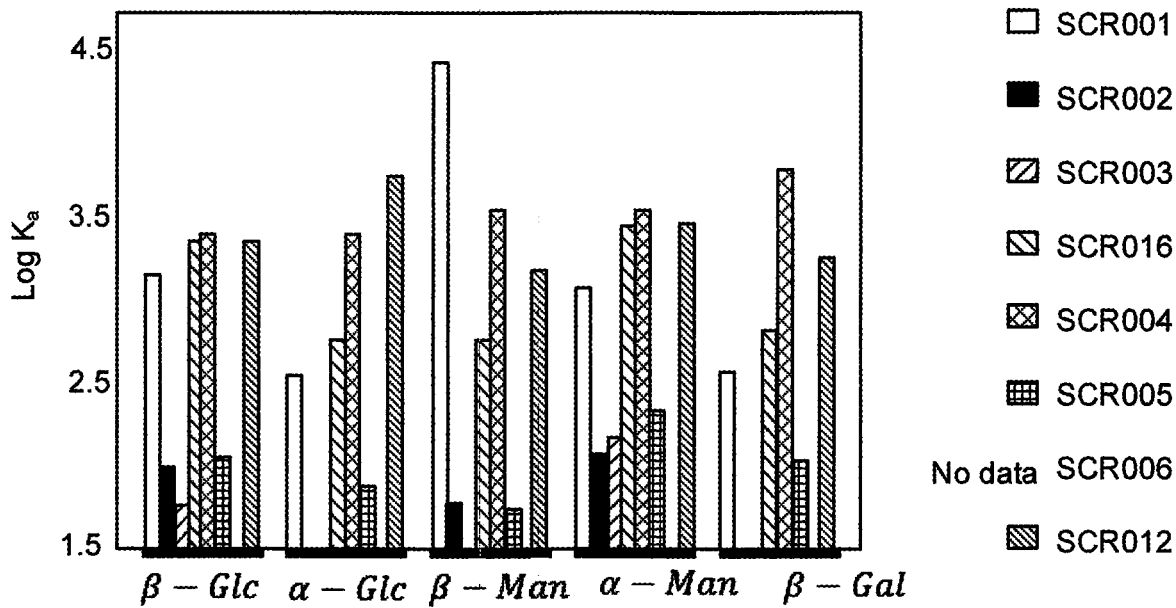
FIG. 20B is a graph depicting relative affinities of the glycans towards different receptors. In both graphs, the baseline is set to log $K_a$ of 1.5 ($K_a$=$3.0 \times 10^1$ $M^{-1}$) as a threshold below which binding is not reported.

Analysis of the data revealed that receptors with pyrrole and imidazole heterocycles bind to all five glycans tested (FIG. 20A and FIG. 20B). Furan and thiophene-based receptors showed either weak, negligible, or no binding. The promiscuous and strong binding of pyrrole-based receptors underscore the importance of H-bond donors for supramolecular association with the glycan guests. This hypothesis is supported by the downfield shifts of the NMR model, and $K_a$s were determined by minimizing the sum of squared residuals between the experimental data and the modelled fit. A threshold was set wherein at least two peaks in each titration must have Δδ>0.02 ppm to fit the data and to avoid overestimation of $K_a$s. Although binding between SCR006 and the sugars was observed in the mass spectrometry data, as the change in the chemical shift for receptor SCR006 with all sugars was <0.02 ppm, the attempted fits of the titration data were not satisfactory, and, as such, a $K_a$ was not reported. All host and guest peaks that shifted above the threshold of Δδ>0.02 ppm were fit simultaneously to maximize the accuracy of the fit, although it should be noted that many peaks with Δδ>0.02 ppm could not be used to calculate $K_a$s because they overlapped with other peaks in the spectra and could not be tracked accurately. The data and fits of the guest and host protons for the titration of SCR012 into a solution of β-Man are provided in FIG. 19B and FIG. 19C, respectively. The NMR and fits to the other thirty-nine host:guest combinations are provided in the Supporting Information.

The $K_d$ for all receptors, and $K_a$ and $\Delta G°$ values for all glycan-receptor combinations from the fits are presented in FIG. 21. To quantify the error in the NMR measurements, the titrations peaks corresponding to the receptor N—H groups. Generally, receptors with furan or thiophene heterocyclic groups that lack heterocyclic H-bond donors bound the glycans weakly, which may account for their weak binding.

For many applications, selectivity may be more important than $K_a$, and the changes in receptor structure explored here have significant consequences on receptor selectivity (FIG. 20A). Among all the receptors tested, SCR001 has selectivity for β-Man with $K_1$ of $1.2 \times 10^3$ M$^{-1}$ and $K_2$ of $3.0 \times 10^1$ M$^{-1}$, and a cumulative $\Delta G°$ of $-6.1$ kcal mol$^{-1}$. While SCR001 shows selectivity for β-Man as high as 103:1 β-Man:β-Gal, SCR002, SCR003, SCR004, SCR005 and SCR016 show selectivity for α-Man. Receptors SCR016 and SCR004 show selectivity as high as α-Man:β-Gal 8:1 and α-Man:β-Glc 4:1, respectively. Receptor SCR002 prefers α-Man:β-Man at a ratio of 2:1, SCR003 binds α-Man:β-Glc at a ratio of 2.8:1, and SCR005 shows selectivity as high as 4.8:1 α-Man:β-Gal. Dimeric receptor SCR012 prefers α-Glc with selectivity as high as α-Glc:β-Man 4.9:1. A threshold of $3.0 \times 10^1$ M$^{-1}$ was set, below which $K_a$s were not reported, as shown in the cases of SCR002.α-Glc, SCR002.β-Gal, SCR003.α-Glc, SCR003.β-Man and SCR003.β-Gal. Alternatively, selectivity can also be analyzed from the perspective of the glycans (FIG. 20B). β-Man has a selectivity for SCR001 over SCR005 at a ratio of 973:1. β-Glc binds preferentially SCR012:SCR003 at a ratio of 55:1, and α-Glc prefers SCR012:SCR006 at a ratio of 74:1. α-Man and β-Gal are selective towards SCR004. α-Man prefers SCR004:SCR002 at a ratio of 63:1, and for β-Gal the preference is SCR004:SCR005 at 140:1. The $K_a$s provided in FIG. 21 reveal the importance of H-bonding motifs, like N—H groups, in the receptor for strong glycan binding. This could account for the observation that receptor SCR003 with N—H groups in the linker shows moderate binding, whereas SCR001, SCR004, and SCR012, which possess H-bonding donors in the heterocycles, bind the strongest. Further, although receptor SCR0012 has more N—H groups compared to SCR001, entropy plays a major role in attenuating binding. Moreover, further experiments are necessary to understand why furan-functionalized receptors bind the glycans more strongly than the thiophene-functionalized receptors. To summarize, SCR001 is selective for β-Man, receptors SCR002, SCR003, SCR016 and SCR005 are selective for α-Man, SCR004 is selective for β-Gal (receptor SCR004 shows a nominal preference for β-Gal over α-Man, but the difference in these two $K_a$s is close to the reported error of measurements), and SCR012 is selective for α-Glc.

Thermodynamic study on the binding of SCR001 and SCR012 with β-Man. To determine how the dimeric structure affected $\Delta H°$ and $\Delta S°$, variable temperature titrations between SCR012 and β-Man and SCR001 and β-Man were performed. The titrations and determinations of $K_d$ and $K_a$ were repeated at 273, 278, 283, and 288 K following the same procedures described above. These titration data were fit to the same binding model involving $K_d$ and 1:1 equilibria to determine the $K_a$s at each temperature between SCR012 and β-Man. The $K_a$s increase with decreasing temperature, suggesting that the binding is entropically disfavored, which is consistent with the binding of SCR001 with β-Man. The obtained $K_a$s were subjected to a van't Hoff analysis to determine $\Delta H°$ and $\Delta S°$ for the binding of SCR012 to β-Man, and values of $-28.5$ kcal mol$^{-1}$ and $-81.3$ e.u. were determined, respectively. Similarly, the variable temperature titration data of the SCR001 and β-Man system were fit using a model involving $K_d$, 1:1 and 2:1 receptor-sugar equilibria, and the determined $K_a$s also increased with decreasing temperature. A van't Hoff plot was generated from the $K_1$s, and $\Delta G°$ and $\Delta S°$ were determined to be $-21.6$ kcal mol$^{-1}$ and $-58.5$ e.u., respectively. Similarly, a van't Hoff plot generated from the $K_2$s revealed $\Delta H°$ and $\Delta S°$ of $-4.8$ kcal mol$^{-1}$ and $-9.4$ e.u., respectively. To understand how dimerizing the receptor structure affects the thermodynamics of binding, the enthalpy and entropy of the binding of SCR012.β-Man should be compared to the sum of the enthalpy and entropy from both binding events of SCR001:β-Man. In doing so, the decrease in unfavorable $\Delta S°$ for SCR12.β-Man compared to SCR012.β-Man reveals that SCR001 binds β-Man with less entropic penalty compared to SCR012, which likely reflects the substantial reorganizational penalty of the larger, flexible molecule. The increase in $\Delta H°$ for SCR012.β-Man compared to SCR001.β-Man indicates that SCR012 likely forms more noncovalent interactions with β-Man compared to SCR001, which may occur between the glycan and the ethylene glycol chain. These thermodynamic studies suggest that dimerizing the receptor imbues SCR012 with multivalency that manifests as an overall increase in binding enthalpy compared to SCR001.

Figure 22A:
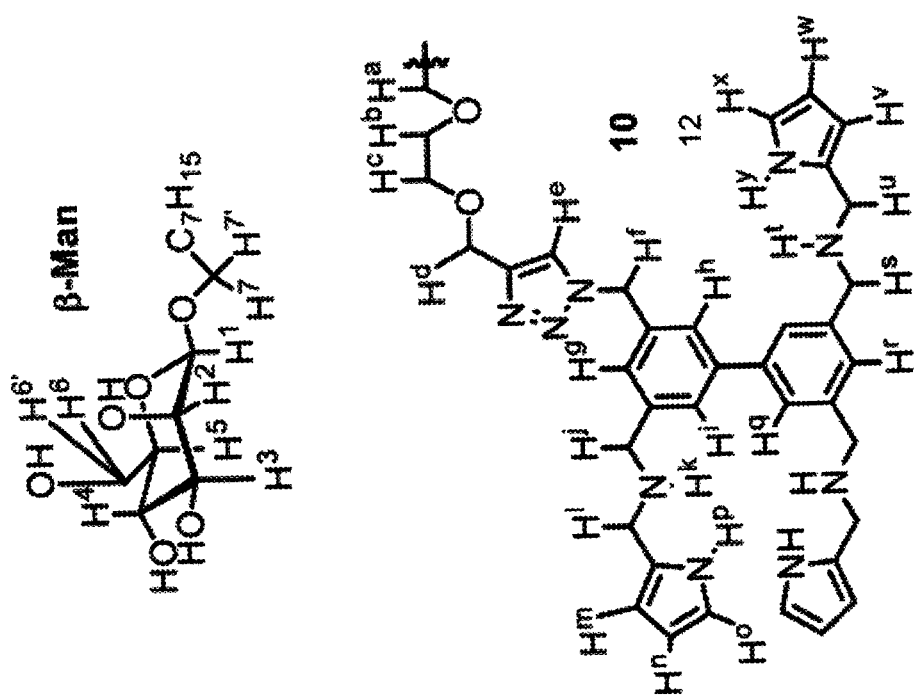
FIG. 22A and FIG. 22B depict a $^1$H—$^1$H 2D NOESY spectrum (700 MHz, $CD_2Cl_2$, 268 K) of a 1:1 mixture of SCR012 (5.6 mM) and β-Man (5.6 mM) showing the intermolecular correlations between host and guest protons.
Figure 22B:
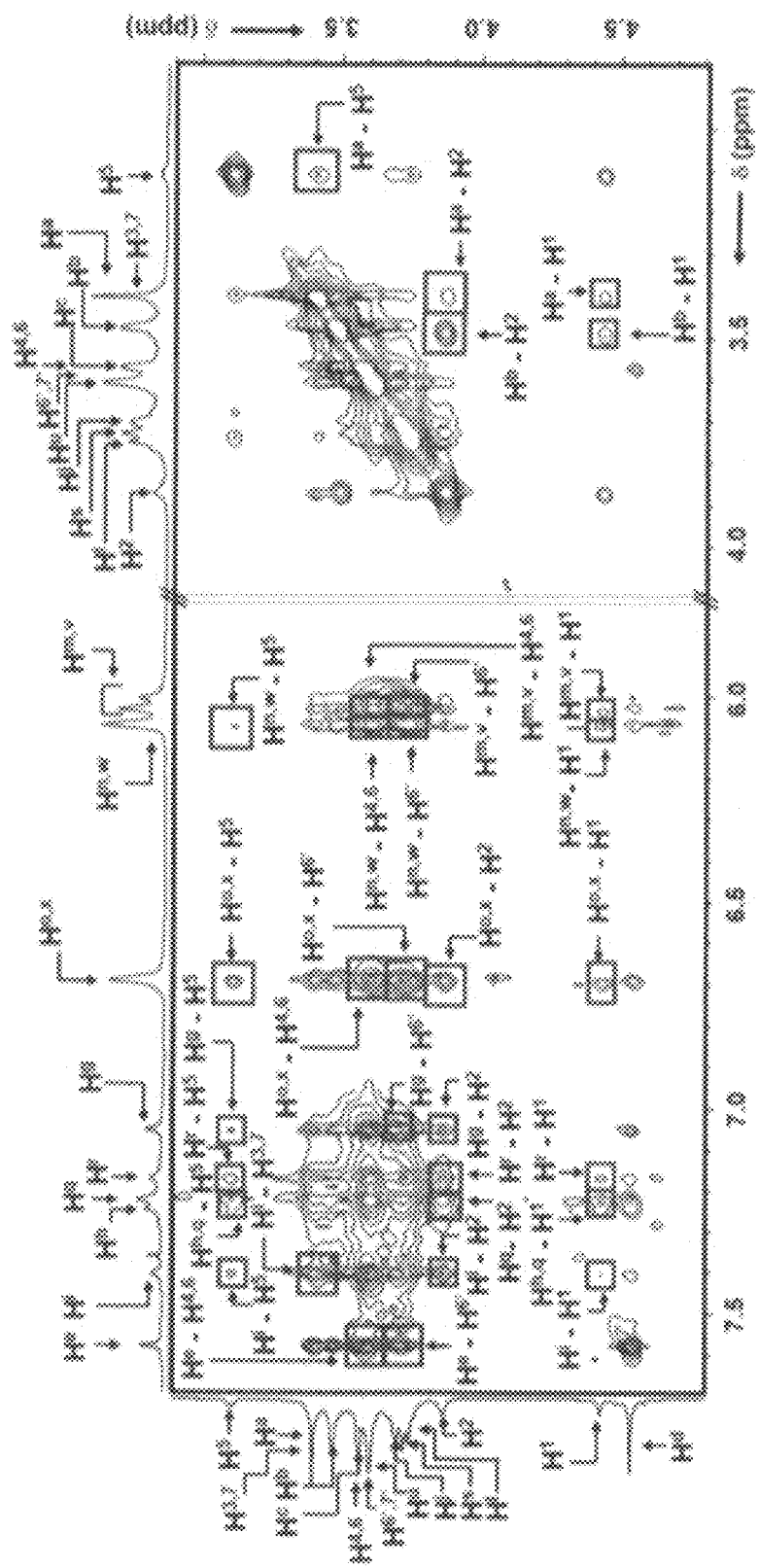

Structure of the SCR012. β-Man complex. The SCR012.β-Man complex was investigated to determine how the flexibility of the receptor enabled "induced-fit" binding, in other words, how the host reorganizes from its lowest energy conformation to form a more stable complex with the glycan. The host:guest structure was determined by $^1$H—$^1$H NOESY measurements in $CD_2Cl_2$ and by computational modelling. $^1$H-$^1$H NOESY spectra provide through-space contacts between the host and guest, and were taken at 700 MHz on a 1:1 mixture of SCR012 and β-Man so that the peaks of host and guest could both be resolved (FIG. 22A and FIG. 22B). Because binding is entropically disfavored, the measurements were performed at 268 K to drive the mixture towards complexation. In addition, the $^1$H—$^1$H NOESY and DQF COSY spectra were also recorded at 268 K and 298 K to assign the peaks of the individual components and to determine if SCR012 rearranges upon complexation.

In the NOESY experiment, the ratio of complexed over uncomplexed host in equilibrium was estimated to be 1:1.2 based on the $K_a$ at 268 K. Several cross-peaks corresponding to host-guest contacts were observed in the NOESY spectrum. As shown in FIG. 22A and FIG. 22B, the intermolecular NOE contours between $H^4$, $H^6$ and the NOESY spectrum, and unconstrained runs which were initiated from different starting structures. The search yielded more than 1500 conformations featuring different host:guest arrangements. Subsequent clustering of these structures, using loose geometric criterion (RMSD ≤0.2 Å), yielded a set of 117 representative structures. The set was further augmented by forty conformations, generated from two additional conformational search runs, which featured H—H contacts closest to those provided by the NOESY experiment. The resulting 157 structures were next optimized using PBE exchange-correlation density functional augmented with long-range dispersion correction (PBE+vdWTS) using the FHI-aims code. Accurate energetics of different complex binding modes derived from density-functional calculations can add extra dimension to the structural analysis to pinpoint and validate the structure of the complex. The geometry-optimizations rendered one exceptionally stable conformation that surpassed the next low-energy structural H6' of β-Man with He of SCR012 show the interaction of receptor with the β-face of β-Man. The NOE contacts between $H^1$, $H^2$ and $H^5$ of β-Man with Hi, Hq and Hr of SCR012 show evidence for the interaction of SCR012 with the α-face of sugar. Observing cross-peaks with SCR012 on both faces of β-Man suggest an inclusion complex where the glycan rests within a pocket formed by the receptor.

Theoretical techniques have been employed to elucidate the structural details of the SCR12.β-Man complex. First, an initial screening of the guest:host conformational space at the force-field level was performed using mixed torsional/low-mode sampling algorithm available in Maestro software. The screening consisted of several constrained, using through-space contacts derived from candidate by 8.6 kcal Although no restraints derived from NOE data were applied to generate this model, all H—H contacts observed in the NOE spectrum are within 10 Å. This structure features the receptor wrapping around the guest molecule in an inclusion-type complex. An aryl ring of one of the two biaryl subunits participates in C—H . . . π interaction with the α-face of the sugar whereas four H-bonds in an equatorial arrangement around the sugar ring are formed by two aminomethylpyrroles and a triazole groups of the same biaryl subunit. Furthermore, the glycol linker wraps the second subunit around the cavity to from four axial H-bonds with the guest. These H-bonding motifs are also consistent with the 2D NOE data. This conformation is further boosted by several additional intramolecular H-bonds, which provides some additional structural stability. While the structure is in satisfactory agreement with the experimental data, this single-molecule model does not fully explain all H—H contacts and for such conformationally flexible receptors other low-energy structures could coexist. Nevertheless, the predicted structure of the complex validates the premise of the design: first, it provides multiple bonding groups that adapt to the guest molecule, which render binding to different monosaccharides promiscuous. Second, the guest binding engages both subunits of the dimeric host molecule, the structural design that was postulated based on study on monomeric receptors.

The conformational search was repeated for the receptor itself, following the same procedure as for the host:guest complex. The density-functional optimization yielded the most stable structure in which importantly, the receptor alone does not bear any cavity suitable for binding the guest. Instead, the binding must proceed by inducing a major conformational change within the receptor to accommodate the guest molecule. As such, the receptor itself maintains a large degree of flexibility which enables desired promiscuous binding of sugars with different hydroxyl group orientations, displaying a behavior similar to many natural glycan binding proteins. Importantly, the pyrroles in this structure are involved in internal H-bonding in the absence of the receptor, which explains why relatively small shifts are observed in the peaks corresponding to the pyrrole N—H protons as their chemical environment does not change substantially upon binding the carbohydrate guests.

An additional nine flexible receptors were designed to understand relationships between receptor structure and $K_a$. These receptors were all synthesized from common intermediate 1 in moderate to excellent yields, demonstrating a modular synthesis that is appropriate for making a broad range of glycan-binding molecules. The binding of these receptors was studied against five octyloxy pyranosides by ESI mass spectrometry in $CH_2Cl_2$ and $^1H$ NMR titrations in $CD_2Cl_2$ at 298 K to quantify $K_a$s. Binding studies were not carried out on SCR007 and SCR008 because the amides rendered these molecules insoluble in $CH_2Cl_2$. ESI-MS spectra of all receptor-sugar complexes showed the presence of the 1:1 receptor-sugar complex in all cases, revealing that, similar to many natural glycan binding proteins, the receptors are promiscuous and bind all glycans in a 1:1 stoichiometry. NMR titrations further confirmed binding was driven by H-bonding and C—H . . . π interactions between the glycan protons and the aromatic groups of the receptors. Curve fitting of the titration data was carried out to quantify association for all forty sugar-receptor combinations, and showed that, with the exception of SCR004 and SCR012, all receptors were selective for mannosides, a compelling biological target. The binding studies also reveal that amine- and imine-based receptors with pyrrole and N-methyl imidazole heterocycles are particularly important. Receptor SCR001 shows the greatest binding with β-Man with $K_1=1.2\times10^3$ $M^{-1}$ and $K_2=3.0\times10^1$ $M^{-1}$, and selectivity of β-Man:β-Gal of 103:1. Moreover, the change of solvent from $CDCl_3$ to $CD_2Cl_2$ does not modify significantly the affinity and specificity of SCR001 other than the increased selectivity towards β-Man. While SCR001,SCR016, SCR004, SCR005 and SCR012 bind all five glycans, SCR002 binds only β-Glc, β-Man, and α-Man, and SCR003 binds only β-Glc and α-Man.

The table of $K_a$s revealed the importance of H-bonding motifs for the strong binding of glycans. By changing the number of H-bonding donors, acceptors, and receptor valency, the selectivity towards the carbohydrates could be altered. Although not yet fully rationalized, the affinities the different receptors display towards the different monosaccharides, which is probably rooted in the subtle interplay of van der Waals and H-bonding interactions, the data provides empirical guidance for designing this class of synthetic carbohydrate receptors. The structure and binding thermodynamics of the SCR012.β-Man complex was explored to determine how the dimerization affected binding, which indicate that SCR012 binds β-Man with larger entropic penalty but forms more intermolecular H-bonds compared to SCR001 with β-Man. The intermolecular NOE contacts of the receptor with both faces of the sugar suggest an inclusion complex where the glycan rests within a pocket formed by the receptor. Formation of the 1:1 receptor-sugar complex and the intermolecular interactions were further supported by molecular-modelling studies. Importantly, the host rearranges to accommodate the guest, confirming that the "induced-fit" model accurately describes this complex. Upon rearrangement, SCR012 forms multiple noncovalent interactions with β-Man, but none of the specific supramolecular contacts were designed, rather, the disclosed approach involved adding sufficient flexibility into the host and retroactively determining the structure.

The majority of synthetic receptors for carbohydrates are specific for all-equatorial monosaccharides, while other monosaccharides are desirable targets for drug delivery or therapeutics because they are over-expressed on the surfaces of many diseased cells. Glycan binding proteins are generally flexible and promiscuous, and achieve selectivity through cooperative and multivalent binding modes. Here, with a series of conformationally-flexible hosts this disclosure demonstrates the value of considering and incorporating biomimetic binding modes into the design of synthetic carbohydrate receptors that bind mannosides.

Binding Study—Experimental

General methods. All solvents, reagents and starting materials were purchased from commercial sources and used without further purification unless otherwise noted. All solvents were dried using a JC Meyer solvent purification system. Aqueous solutions were prepared from nanopure water from a Milli-Q plus system, with a resistivity over 18 MΩ cm$^{-1}$. Chromatography purifications were performed using silica gel (60 Å, 70-230 mesh). Thin-layer chromatography (TLC) was carried out using aluminum sheets precoated with silica gel 60 (EMD 40-60 mm, 230-400 mesh with 254 nm dye). TLC plates were visualized by UV-light and using charring solution (prepared by dropwise addition of conc.$H_2SO_4$ (5 mL) to a solution of $H_3PMo_{12}O_{40}$ (1 g) and $Ce(SO_4)_2$ (2 g) in water (95 mL)), alkaline $KMnO_4$ solution (prepared by dissolving $KMnO_4$ (2 g) and $NaHCO_3$ (4 g) in water (100 mL)), and heat as developing agents. All reactions were carried out under an inert atmosphere of Ar using standard Schlenk techniques unless otherwise noted. Reaction flasks were dried in an oven at 100° C. for 12 h. Compounds SCR001, 1 and SCR016, SCR006, SCR012, 13-tetraoxahexadeca-1,15-diyne were synthesized according to published literature procedures. Deuterated solvents were purchased from Cambridge Isotope Laboratories Inc. and used as received. NMR spectra were obtained on a Bruker AVANCE 300 MHz spectrometer. All chemical shifts are reported in δ units (ppm) using the solvent residual signal as an internal standard. The following abbreviations are used for signal multiplicities: s, singlet; br s, broad singlet, d, doublet; t, triplet; q, quartet; m, multiplet; dd, doublet of doublets. High-resolution electrospray ionization mass spectra were obtained on Agilent Q-TOF system.

Synthesis of 1,1',1'',1'''-([1,1'-biphenyl]-3,3',5,5'-tetrayl) tetrakis(N-(furan-2-ylmethyl)methanamine) SCR002. PPh$_3$ (1.76 g, 6.7 mmol) was added to a stirring solution of 1 (500 mg, 1.34 mmol) in THF (30 mL) at room temperature. The reaction was refluxed under Ar atmosphere for 1 h before the addition of furan-2-carbaldehyde (640 mg, 6.7 mmol) at room temperature. The reaction mixture was refluxed for additional 48 h, cooled to room temperature, and concentrated under reduced pressure. The residue was dissolved in MeOH (30 mL), and NaBH$_4$ (507 mg, 13.4 mmol), was added in portions at room temperature under Ar atmosphere followed by stirring for 16 h. The reaction mixture was concentrated under reduced pressure, extracted with CHCl$_3$ (3×50 mL), and the combined organic layers were dried over anhydrous Na$_2$SO$_4$, filtered and concentrated under reduced pressure. The crude product was treated with H$_2$O (10 mL), acidified with 3M HCl and washed with CHCl$_3$ (3×40 mL). The pH of the aqueous layer was raised with 3M NaOH and extracted with CHCl$_3$ (3×40 mL). The combined organic layers were dried over anhydrous Na$_2$SO$_4$, filtered and concentrated under reduced pressure to provide SCR002 (750 mg, 95%) as a brown gum. $^1$H NMR (300 MHz, CDCl$_3$) δ=7.46 (d, J=1.4 Hz, 4H), 7.37 (dd, J=1.9, 0.8 Hz, 4H), 7.28 (s, 2H), 6.32 (dd, J=3.1, 1.9 Hz, 4H), 6.20 (dd, J=3.1, 0.5 Hz, 4H), 3.84 (s, 8H), 3.83 (s, 8H), 1.88 (br s, 4H); $^{13}$C NMR (75 MHz, CDCl$_3$) δ=153.90, 141.98, 141.47, 140.70, 127.26, 126.03, 110.25, 107.23, 53.00, 45.66; HRMS (ESI): m/z calcd for C$_{36}$H$_{39}$N$_4$O$_4$ [M+H]$^+$: 591.2966, found 591.2958.

Synthesis of 1,1',1'',1'''-([1,1'-biphenyl]-3,3',5,5'-tetrayl) tetrakis(N-(thiophen-2-ylmethyl)methanamine) SCR003. PPh$_3$ (1.76 g, 6.7 mmol) was added to a stirring solution of 1 (500 mg, 1.34 mmol) in THF (30 mL) at room temperature. The reaction was refluxed under Ar atmosphere for 1 h before the addition of thiophene-2-carbaldehyde (751 mg, 6.7 mmol) at room temperature. The reaction mixture was refluxed for an additional 48 h, cooled to room temperature, and concentrated under reduced pressure. The residue was dissolved MeOH (30 mL), and NaBH$_4$ (507 mg, 13.4 mmol) was added in portions at room temperature under Ar atmosphere followed by stirring for 16 h. The reaction mixture was concentrated under reduced pressure, treated with CHCl$_3$ (50 mL) and water (50 mL), and the organic layer was separated. The aqueous layer was extracted with CHCl$_3$ (3×50 mL), and the combined organic layers were dried over anhydrous Na$_2$SO$_4$, filtered and concentrated under reduced pressure. The crude product was treated with H$_2$O (10 mL), acidified with 3M HCl and washed with CHCl$_3$ (3×40 mL). The pH of the aqueous layer was raised with 3M NaOH and extracted with CHCl$_3$ (3×40 mL). The combined organic layers were dried over anhydrous Na$_2$SO$_4$, filtered and concentrated under reduced pressure to provide SCR003 (350 mg, 40%) as a colorless gum. $^1$H NMR (300 MHz, CDCl$_3$) δ=7.48 (d, J=1.2 Hz, 4H), 7.31 (s, 2H), 7.22 (dd, J=4.6, 1.7 Hz, 4H), 7.00-6.87 (m, 8H), 4.04 (s, 8H), 3.91 (s, 8H), 1.82 (br s, 4H); $^{13}$C NMR (75 MHz, CDCl$_3$) δ=144.25, 141.51, 140.84, 127.17, 126.77, 125.97, 125.09, 124.54, 52.94, 47.80; HRMS (ESI): m/z calcd for C$_{36}$H$_{39}$N$_4$S$_4$ [M+H]$^+$: 655.2052, found 655.2048.

Synthesis of 1,1',1'',1'''-([1,1'$^1$-biphenyl]-3,3',5,5'-tetrayl) tetrakis(N-((1-methyl-1H-imidazol-2-yl)methyl)methanamine) SCR016. PPh$_3$ (1.76 g, 6.7 mmol) was added to a stirring solution of 1 (500 mg, 1.34 mmol) in THF (30 mL) at room temperature. The reaction was refluxed under Ar atmosphere for 1 h before the addition of 1-methyl-1H-imidazole-2-carbaldehyde (740 mg, 6.7 mmol) at room temperature. The reaction mixture was refluxed for an additional 48 h, cooled to room temperature, and concentrated under reduced pressure. The residue was dissolved MeOH (30 mL), and NaBH$_4$ (507 mg, 13.4 mmol) was added portion wise at room temperature under Ar atmosphere followed by stirring at the same temperature for 16 h. The reaction mixture was concentrated under reduced pressure, treated with CHCl$_3$ (50 mL) and H$_2$O (50 mL), and the organic layer was separated. The aqueous layer was extracted with CHCl$_3$ (3×50 mL), and the combined organic layers were dried over anhydrous Na$_2$SO$_4$, filtered and concentrated under reduced pressure. The crude product was treated with water (10 mL), acidified with 3M HCl and washed with CHCl$_3$ (3×40 mL). The aqueous layer was basified with 3M NaOH and extracted with CHCl$_3$ (3×40 mL). The combined organic layers were dried over anhydrous Na$_2$SO$_4$, filtered and concentrated under reduced pressure. The resulting residue was purified by column chromatography (SiO$_2$, 9:1:0.5 CHCl$_3$:MeOH:NH$_3$) to provide SCR0016 (400 mg, 46%) as a pale yellow oil. $^1$H NMR (300 MHz, CDCl$_3$) b=7.44 (s, 4H), 7.29 (s, 2H), 6.92 (br s, 4H), 6.80 (br s, 4H), 3.87 (s, 8H), 3.86 (s, 8H), 3.62 (s, 12H), 2.28 (br s, 4H); $^{13}$C NMR (75 MHz, CDCl$_3$) δ=146.40, 141.23, 140.55, 127.10, 127.01, 125.75, 121.19, 53.50, 45.17, 32.70; HRMS (ESI): m/z calcd for C$_{36}$H$_{47}$N$_{12}$ [M+H]$^+$: 647.4041, found 647.4036.

Synthesis of (1E,1'E,1"E,1'"E)-N,N',N",N'"-([1,1'-biphenyl]-3,3',5,5'-tetrayltetrakis(methylene))tetrakis(1-(1H-pyrrol-2-yl)methanimine) SCR004. PPh$_3$ (1.76 g, 6.7 mmol) was added to a stirring solution of 1 (500 mg, 1.34 mmol) in THF (30 mL) at room temperature. The reaction was heated to 90° C. under Ar atmosphere and stirred for 1 h before the addition of 1H-pyrrole-2-carbaldehyde (637 mg, 6.7 mmol) at room temperature. The reaction mixture was stirred for an additional 30 h at 90° C., cooled to room temperature, and concentrated under reduced pressure. The crude product was purified by column chromatography (SiO$_2$, 9:1:0.5 CHCl$_3$:MeOH:NH$_3$) to provide SCR004 (250 mg, 32%) as a yellow solid. $^1$H NMR (300 MHz, DMSO) δ=11.43 (br s, 4H), 8.25 (s, 4H), 7.50 (s, 4H), 7.26 (s, 2H), 6.88 (s, 4H), 6.49 (dd, J=3.3, 1.0 Hz, 4H), 6.12 (t, J=3.0 Hz, 4H), 4.73 (s, 8H); $^{13}$C NMR (75 MHz, DMSO) δ=152.60, 140.90, 140.42, 129.95, 126.94, 124.95, 122.29, 113.92, 108.97, 63.90; HRMS (ESI): m/z calcd for C$_{36}$H$_{35}$N$_8$ [M+H]$^+$: 579.2979, found 579.2973.

Synthesis of (1E,1'E,1"E,1'"E)-N,N',N",N'"-([1,1'-biphenyl]-3,3',5,5'-tetrayltetrakis(methylene))tetrakis(1-(furan-2-yl)methanimine) SCR005. PPh$_3$ (1.76 g, 6.7 mmol) was added to a stirring solution of 1 (500 mg, 1.34 mmol) in THF (30 mL) at room temperature. The reaction was refluxed under Ar atmosphere for 1 h before the addition of furan-2-carbaldehyde (643.8 mg, 6.7 mmol) at room temperature. The reaction mixture was refluxed for an additional 48 h, cooled to room temperature, and concentrated under reduced pressure. The crude product was purified by column chromatography (SiO$_2$, 9:1:0.5 CHCl$_3$:MeOH:NH$_3$) to provide SCR005 (150 mg, 19%) as a light brown solid. $^1$H NMR (300 MHz, CDCl$_3$) δ=8.17 (s, 4H), 7.50 (s, 4H), 7.45 (s, 4H), 7.26 (s, 4H), 6.76 (d, J=3.3 Hz, 4H), 6.46 (dd, J=3.3, 1.7 Hz, 4H), 4.82 (s, 8H); $^{13}$C NMR (75 MHz, CDCl$_3$) δ=151.55, 150.52, 144.79, 141.69, 139.51, 127.36, 126.25, 114.34, 111.64, 65.13; HRMS (ESI): m/z calcd for C$_{36}$H$_{31}$N$_4$O$_4$ [M+H]$^+$: 583.2340, found 583.2335.

Synthesis of (1E,1'E,1"E,1'"E)-N,N',N",N'"-([1,1'-biphenyl]-3,3',5,5'-tetrayltetrakis(methylene))tetrakis(1-(thiophen-2-yl)methanimine) SCR006. PPh$_3$ (1.76 g, 6.7 mmol) was added to a stirring solution of 1 (500 mg, 1.34 mmol) in THF (30 mL) at room temperature. The reaction was refluxed under Ar atmosphere for 1 h before the addition of thiophene-2-carbaldehyde (751 mg, 6.7 mmol) at room temperature. The reaction mixture was refluxed for an additional 48 h, cooled to room temperature, and concentrated under reduced pressure. The crude product was purified by column chromatography (SiO$_2$, 9:1:0.5 CHCl$_3$:MeOH:NH$_3$) to provide SCR006 (150 mg, 17%) as a light brown solid. $^1$H NMR (300 MHz, CDCl$_3$) d=8.49 (s, 4H), 7.47 (s, 4H), 7.40 (br s, 4H), 7.34 (br s, 4H), 7.28 (d, 2H), 7.08 (br s, 4H), 4.85 (s, 8H); $^{13}$C NMR (75 MHz, CDCl$_3$) δ=155.36, 142.53, 141.74, 139.78, 130.78, 129.12, 127.40, 127.04, 126.03, 64.53; HRMS (ESI): m/z calcd for C$_{36}$H$_{31}$N$_4$S$_4$ [M+H]$^+$: 647.1426, found 647.1424.

Synthesis of [1,1'-biphenyl]-3,3',5,5'-tetrayltetramethanamine tetrahydrochloride 2. PPh$_3$ (5.25 g, 20.0 mmol) was added to a stirring solution of 1 (1.00 g, 2.67 mmol) in THF (80 mL) at room temperature. The reaction was heated at 65° C. under Ar atmosphere for 1 h before the addition of H$_2$O (20 mL) at room temperature. The reaction mixture was heated at 65° C. for an additional 18 h, cooled to room temperature, and HCl (37% in H$_2$O, 20 mL) was added dropwise. After stirring the solution for 2 h, the reaction mixture was washed with CH$_2$Cl$_2$ (3×100 mL), and the aqueous layer was filtered and concentrated under reduced pressure to give 2 (1.1 g, 99%) as pale white solid. $^1$H NMR (300 MHz, D$_2$O) d=7.75 (d, J=1.4 Hz, 4H), 7.49 (s, 2H), 4.25 (s, 8H); $^{13}$C NMR (75 MHz, D$_2$O) δ=141.03, 134.40, 128.69, 128.38, 42.75; HRMS (ESI): m/z calcd for C$_{16}$H$_{23}$N$_4$ [M−4HCl+H]$^+$: 271.1917, found 271.1916.

Synthesis of N,N',N",N'"-([1,1'-biphenyl]-3,3',5,5'-tetrayltetrakis(methylene))tetrakis(furan-2-carboxamide) SCR007. N,N-diisopropylethylamine (4.2 mL, 24 mmol) was added dropwise to a suspension of [1,1'-biphenyl]-3,3',5,5'-tetrayltetramethanamine tetrahydrochloride (0.50 g, 1.2 mmol) and furan-2-carboxylic acid (0.65 g, 5.76 mmol) in dry DMF (10 mL) at room temperature under Argon atmosphere followed by stirring for 10 min. HBTU (2.19 g, 5.76 mmol) was added at room temperature and then stirred for 36 h. The reaction mixture was concentrated under reduced pressure to remove DMF, and the resulting residue was dissolved in 10% MeOH/EtOAc (40 mL), washed successively with saturated NaHCO$_3$ (aq) solution (3×20 mL) and water (3×20 mL). The organic layer was dried over anhydrous Na$_2$SO$_4$, filtered and concentrated under reduced pressure to give the crude product which was triturated with diethyl ether and dried in vacuo to afford SCR007 (0.65 g, 84%) as a light brown solid. $^1$H NMR (300 MHz, DMSO) δ=8.96 (t, J=6.0 Hz, 4H), 7.83 (d, J=1.1 Hz, 4H), 7.42 (s, 4H), 7.26 (s, 2H), 7.10 (d, J=3.4 Hz, 4H), 6.62 (dd, J=3.4, 1.8 Hz, 4H), 4.46 (d, J=6.0 Hz, 8H); $^{13}$C NMR (75 MHz, CDCl$_3$) δ=158.21, 148.26, 145.50, 140.83, 140.79, 126.15, 125.13, 113.94, 112.29, 42.48; HRMS (ESI): m/z calcd for C$_{36}$H$_{31}$N$_4$O$_8$ [M+H]$^+$: 647.2136, found 647.2124.

Synthesis of N,N',N",N'"-([1,1'-biphenyl]-3,3',5,5'-tetrayltetrakis(methylene))tetrakis(thiophene-2-carboxamide) SCR008. N,N-diisopropylethylamine (0.42 mL, 2.4 mmol) was added dropwise to a suspension of [1,1'-biphenyl]-3,3', 5,5'-tetrayltetramethanamine tetrahydrochloride (0.05 g, 0.12 mmol) and thiophene-2-carboxylic acid (0.074 g, 0.576 mmol) in dry DMF (3 mL) at room temperature under Argon atmosphere followed by stirring for 10 min. HBTU (0.219 g, 0.576 mmol) was added in one portion at room temperature and then stirred for 36 h. The reaction mixture was concentrated under reduced pressure to remove DMF, and the resulting residue was dissolved in 10% MeOH/EtOAc (10 mL), washed successively with saturated NaHCO$_3$ (aq) solution (3×10 mL) and H$_2$O (3×10 mL). The organic layer was dried over anhydrous Na$_2$SO$_4$, filtered and concentrated under reduced pressure to give the crude product which was triturated with diethyl ether and dried in vacuo to afford SCR008 (0.035 g, 41%) as a light brown solid. $^1$H NMR (500 MHz, CDCl$_3$) δ=9.08 (t, J=5.9 Hz, 4H), 7.81-7.70 (m, 8H), 7.45 (s, 4H), 7.29 (s, 2H), 7.13 (dd, J=5.0, 3.7 Hz, 4H), 4.49 (d, J=5.9 Hz, 8H); $^{13}$C NMR (75 MHz, CDCl$_3$) δ=161.12, 140.43, 140.38, 139.80, 130.81, 128.14, 127.91, 125.69, 124.68, 42.59; HRMS (ESI): m/z calcd for C$_{36}$H$_{31}$N$_4$O$_4$S$_4$ [M+H]$^+$: 711.1223, found 711.1207.

Synthesis of 1,12-bis(1-((3',5,5'-tris(azidomethyl)-[1,1'-biphenyl]-3-yl)methyl)-1H-1,2,3-triazol-4-yl)-2,5,8,11-tetraoxadodecane 13. 4,7,10,13-tetraoxahexadeca-1,15-diyne (240 mg, 1.06 mmol) and 1 (2.0 g, 5.34 mmol) were dissolved in 90 mL anhydrous DMF. 10 mL H$_2$O was added, followed by sodium ascorbate (828 mg, 4.17 mmol), CuSO$_4$ (35.4 mg, 0.21 mmol) and bathocuproinedisulfonic acid disodium salt (145 mg, 0.26 mmol). The mixture was stirred at room temperature under Ar for 24 h. The reaction mixture was concentrated under reduced pressure and purified by column chromatography (SiO$_2$, 100:1.4 CHCl$_3$:MeOH) to provide 13 (400 mg, 39%) as a pale yellow oil. $^1$H NMR (300 MHz, CDCl$_3$) δ=7.58 (s, 2H), 7.51 (s, 2H), 7.47 (s, 2H), 7.46 (s, 4H), 7.29 (s, 2H), 7.23 (s, 2H), 5.58 (s, 4H), 4.65 (s, 4H), 4.44 (s, 8H), 4.42 (s, 4H), 3.70-3.64 (m, 4H), 3.64-3.58 (m, 4H), 3.57 (s, 4H); $^{13}$C NMR (125 MHz, CDCl$_3$) δ=145.83, 141.83, 141.17, 137.44, 137.12, 136.23, 127.28, 127.23, 127.05, 126.89, 126.82, 122.80, 70.62, 70.54, 69.87, 64.71, 54.48, 54.35, 53.86; HRMS (ESI): m/z calcd for C$_{44}$H$_{46}$N$_{24}$O$_4$Na [M+Na]$^+$: 997.4032, found 997.3962.

Synthesis of SCR012. PPh$_3$ (1.535 g, 5.85 mmol) was added to a stirring solution of 13 (830 mg, 0.851 mmol) in PhMe (90 mL) at room temperature and heated at 90° C. under Ar atmosphere for 1 h before the addition of 1H-pyrrole-2-carbaldehyde (556 mg, 5.84 mmol) at room temperature. The reaction mixture was stirred for an additional 48 h at 110° C., cooled to room temperature, and concentrated under reduced pressure. The resulting residue was dissolved in MeOH (90 mL), and NaBH$_4$ (319 mg, 8.44 mmol) was added to the solution over 20 min at room temperature. After stirring for 1 h, the reaction mixture was poured into H$_2$O/brine (70 mL 1:1) and extracted with CH$_2$Cl$_2$ (4×70 mL). The organic fractions were combined, dried over anhydrous Na$_2$SO$_4$, concentrated under reduced pressure, and purified by column chromatography (SiO$_2$, 7:1:1 CHCl$_3$:MeOH:NH$_3$) to provide SCR012 (550 mg, 50%) as a brown solid. $^1$H NMR (700 MHz, CD$_2$Cl$_2$) δ=9.65 (s, 6H), 7.67 (s, 2H), 7.50 (s, 2H), 7.40 (s, 4H), 7.37 (s, 2H), 7.20 (s, 4H), 6.80 (s, 6H), 6.19-6.13 (m, 12H), 5.45 (s, 4H), 4.66 (s, 4H), 3.88 (s, 8H), 3.85 (s, 4H), 3.79 (s, 12H), 3.68 (s, 4H), 3.60 (s, 4H), 3.54 (s, 4H), 3.10-2.23 (br s, 6H); $^{13}$C NMR (175 MHz, CD$_2$Cl$_2$) δ=145.85, 141.06, 140.59, 135.98, 129.46, 129.02, 128.07, 127.61, 127.07, 126.01, 125.85, 123.49, 121.00, 117.86, 117.58, 108.19, 107.07, 106.98, 70.69, 70.14, 64.81, 53.19, 52.97, 46.26; HRMS (ESI): m/z calcd for C$_{74}$H$_{89}$N$_{18}$O$_4$ [M+H]$^+$: 1293.7314, found 1293.7417.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims.

What is claimed is:

1. A method for treating a human for a Zika (ZIKV) virus infection, the method comprising
    administering a synthetic carbohydrate receptor (SCR) to the human, wherein the synthetic carbohydrate receptor (SCR) has a structure of:

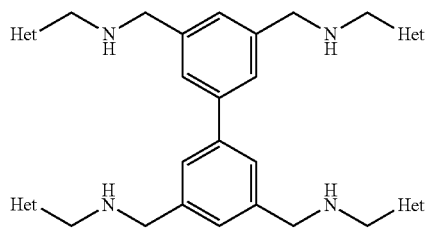

wherein Het is a heteroaromatic group selected from 2-pyrrole, 3-pyrrole, 2-pyridine, 3-pyridine, 2-indol, 3-indole, 2-thiophene, 2-furan, N-methyl-2-imidazole and 2-phenol.

2. The method as recited in claim 1, further comprising diagnosing the human as being infected with the Zika (ZIKV) virus and subsequently performing the step of administering.

3. The method as recited in claim 1, wherein the heteroaromatic group is selected from 2-pyrrole, 3-pyrrole, 2-pyridine and 3-pyridine.

4. The method as recited in claim 1, wherein the heteroaromatic group is selected from 2-pyrrole and 3-pyrrole.

5. The method as recited in claim 1, wherein the heteroaromatic group is selected from 2-pyridine and 3-pyridine.

6. The method as recited in claim 1, wherein the heteroaromatic group is selected from 2-indole and 3-indole.

7. The method as recited in claim 1, wherein the heteroaromatic group is selected from 2-thiophene and 2-furan.

8. The method as recited in claim 1, wherein the heteroaromatic group is N-methyl-2-imidazole.

9. The method as recited in claim 1, wherein the heteroaromatic group is 2-phenol.

10. A composition of matter comprising a synthetic carbohydrate receptor (SCR) with a structure of:

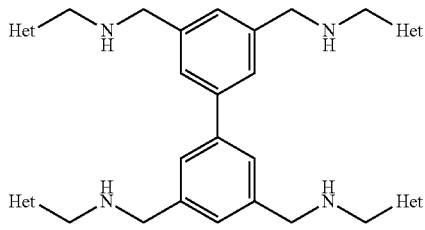

wherein Het is a heteroaromatic group selected from 3-pyrrole, 2-pyridine, 3-pyridine, 2-indol, 3-indole, 2-thiophene, 2-furan, N-methyl-2-imidazole and 2-phenol.

11. A composition of matter comprising a synthetic carbohydrate receptor (SCR) with a structure of:

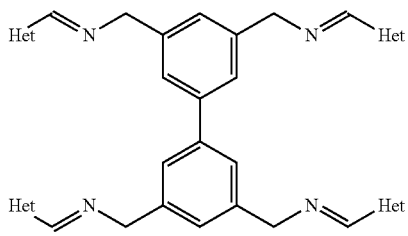

wherein Het is 2-pyrrole.

12. A method for treating a human for a Zika (ZIKV) virus infection, the method comprising
    administering the synthetic carbohydrate receptor (SCR) of claim 11 to the human.

13. A composition of matter comprising a synthetic carbohydrate receptor (SCR) with a structure of:

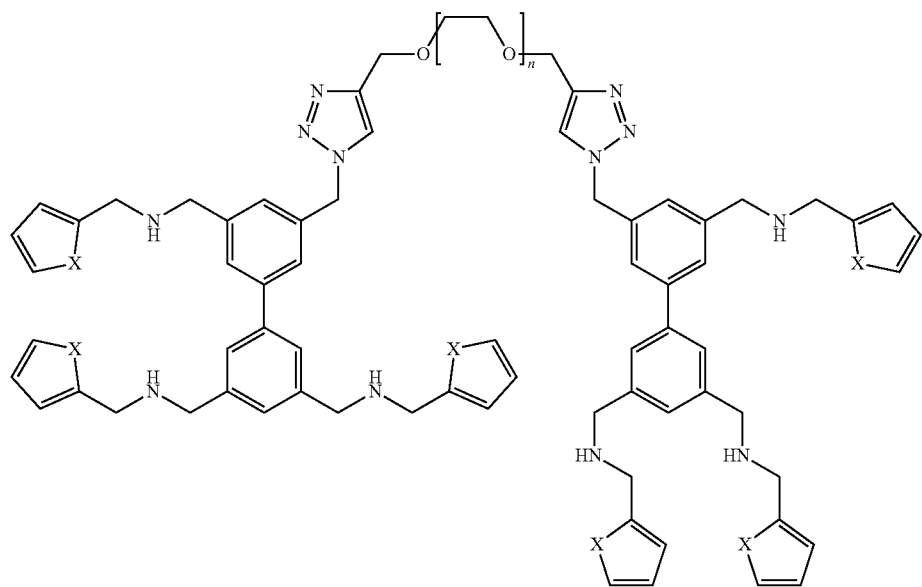

wherein n=1, 2 or 3 and X is NH or O.

14. The composition of matter as recited in claim 10, wherein Het is 2-indole or 3-indole.

15. The composition of matter as recited in claim 10, wherein Het is 3-indole.

16. A method for treating a human for a Zika (ZIKV) virus infection, the method comprising
administering the synthetic carbohydrate receptor (SCR) of claim 15 to the human.

17. A method for treating a human for a virus infection, the method comprising
administering the synthetic carbohydrate receptor (SCR) of claim 14 to the human.

18. A method for treating a human for a Zika (ZIKV) virus infection, the method comprising
administering the synthetic carbohydrate receptor (SCR) of claim 13 to the human.

* * * * *